(12) United States Patent
Mahr et al.

(10) Patent No.: US 10,898,559 B2
(45) Date of Patent: Jan. 26, 2021

(54) PEPTIDES AND COMBINATION OF PEPTIDES FOR USE IN IMMUNOTHERAPY AGAINST LUNG CANCER, INCLUDING NSCLC AND OTHER CANCERS

(71) Applicant: Immatics Biotechnologies GmbH, Tuebingen (DE)

(72) Inventors: Andrea Mahr, Tuebingen (DE); Toni Weinschenk, Aichwald (DE); Oliver Schoor, Tuebingen (DE); Jens Fritsche, Dusslingen (DE); Harpreet Singh, Munich (DE); Claudia Wagner, Tuebingen (DE); Julia Leibold, Langkampfen (AT); Colette Song, Ostfildern (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/915,707

(22) Filed: Jun. 29, 2020

(65) Prior Publication Data

US 2020/0384093 A1 Dec. 10, 2020

Related U.S. Application Data

(63) Continuation of application No. 16/305,686, filed as application No. PCT/EP2016/059053 on Apr. 22, 2016.

(60) Provisional application No. 62/152,258, filed on Apr. 24, 2015.

(30) Foreign Application Priority Data

Apr. 24, 2015 (GB) .................... 1507030.3

(51) Int. Cl.
| | |
|---|---|
| A61K 39/00 | (2006.01) |
| G16B 20/20 | (2019.01) |
| A61K 35/17 | (2015.01) |
| C07K 14/47 | (2006.01) |
| C07K 14/725 | (2006.01) |
| C07K 14/74 | (2006.01) |
| C07K 16/28 | (2006.01) |
| C07K 16/30 | (2006.01) |
| C12N 5/0783 | (2010.01) |
| C12Q 1/6886 | (2018.01) |
| G01N 33/574 | (2006.01) |
| A61P 35/00 | (2006.01) |

(52) U.S. Cl.
CPC .......... *A61K 39/0011* (2013.01); *A61K 35/17* (2013.01); *A61P 35/00* (2018.01); *C07K 14/4748* (2013.01); *C07K 14/7051* (2013.01); *C07K 14/70539* (2013.01); *C07K 16/2833* (2013.01); *C07K 16/30* (2013.01); *C12N 5/0638* (2013.01); *C12Q 1/6886* (2013.01); *G01N 33/57492* (2013.01); *G16B 20/20* (2019.02); *C07K 2319/00* (2013.01); *C07K 2319/30* (2013.01); *C07K 2319/33* (2013.01); *C07K 2319/55* (2013.01); *C07K 2319/74* (2013.01); *C12N 2501/50* (2013.01); *C12Q 2600/106* (2013.01); *C12Q 2600/112* (2013.01); *C12Q 2600/156* (2013.01)

(58) Field of Classification Search
CPC ..... A61P 35/00; C07K 14/4748; C07K 16/30; C07K 14/70539; C07K 16/2833; A61K 35/17; C12N 2501/50
See application file for complete search history.

(56) References Cited

U.S. PATENT DOCUMENTS

| | | |
|---|---|---|
| 6,252,052 B1 | 6/2001 | Stockert et al. |
| 6,703,491 B1 | 3/2004 | Homburger et al. |
| 8,080,634 B2 | 12/2011 | Singh et al. |
| 8,669,230 B2 | 3/2014 | Singh et al. |
| 9,101,585 B2 | 8/2015 | Fritsche et al. |
| 9,511,128 B2 | 12/2016 | Singh et al. |
| 9,717,774 B2 | 8/2017 | Fritsche et al. |
| 9,895,415 B2 | 2/2018 | Fritsche et al. |
| 9,943,579 B2 | 4/2018 | Weinschenk et al. |
| 9,950,048 B2 | 4/2018 | Singh et al. |

(Continued)

FOREIGN PATENT DOCUMENTS

| | | |
|---|---|---|
| CN | 1869064 A | 11/2006 |
| EP | 1332760 A1 | 8/2003 |

(Continued)

OTHER PUBLICATIONS

PCT International Search Report for PCT/EP2016/059053, dated Sep. 30, 2016.

(Continued)

*Primary Examiner* — Lei Yao
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 17 Drawing Sheets
(2 of 17 Drawing Sheet(s) Filed in Color)
Specification includes a Sequence Listing.

(56) References Cited

U.S. PATENT DOCUMENTS

| | | |
|---|---|---|
| 9,993,523 B2 | 6/2018 | Fritsche et al. |
| 10,071,148 B2 | 9/2018 | Weinschenk et al. |
| 10,525,114 B2 | 1/2020 | Mahr et al. |
| 10,568,950 B1 | 2/2020 | Mahr et al. |
| 10,576,132 B2 | 3/2020 | Mahr et al. |
| 10,695,411 B2 | 6/2020 | Mahr et al. |
| 2005/0244823 A1 | 11/2005 | Drijfhout et al. |
| 2010/0239615 A1 | 9/2010 | Wang et al. |
| 2011/0229505 A1 | 9/2011 | Fritsche et al. |
| 2013/0115216 A1 | 5/2013 | Straten et al. |
| 2015/0037820 A1 | 2/2015 | Birse et al. |
| 2016/0168200 A1 | 6/2016 | Weinschenk et al. |
| 2017/0304399 A1 | 10/2017 | Fritsche et al. |
| 2018/0125929 A1 | 5/2018 | Fritsche et al. |

FOREIGN PATENT DOCUMENTS

| | | |
|---|---|---|
| WO | 01/53349 A2 | 7/2001 |
| WO | 2007103770 A2 | 9/2007 |
| WO | 2009/015842 A2 | 2/2009 |
| WO | 2009/075883 A2 | 6/2009 |
| WO | 2009126805 A2 | 10/2009 |
| WO | 2011/025572 A1 | 3/2011 |
| WO | 2011/113819 A2 | 9/2011 |
| WO | 2011/113882 A1 | 9/2011 |
| WO | 2013/034741 A1 | 9/2011 |
| WO | 2011119484 A1 | 9/2011 |
| WO | 2011/143656 A2 | 11/2011 |
| WO | 2012048291 A2 | 4/2012 |
| WO | 2012/100023 A1 | 7/2012 |
| WO | 2014/188721 A1 | 11/2014 |
| WO | 2015/018805 A1 | 2/2015 |
| WO | 2017036936 A1 | 3/2017 |

OTHER PUBLICATIONS

Great Britain Search Report for GB1507030.3, dated Jan. 21, 2016.

Weinschenk et al., "Integrated Functional Genomics Approach for the Design of Patient-Individual Antitumor Vaccines" Cancer Research. (Oct. 15, 2002) 62: 5818-5827.

Sunami et al., "MMP-1 Is a Prognostic Marker for Hematogenous Metastasis of Colorectal Cancer" The Oncologist (2005) 5:108-114.

Bostrom et al., "MMP-1 Expression Has an Independent Prognostic Value in Breast Cancer" BMC Cancer (2011) 11:248: 1-8.

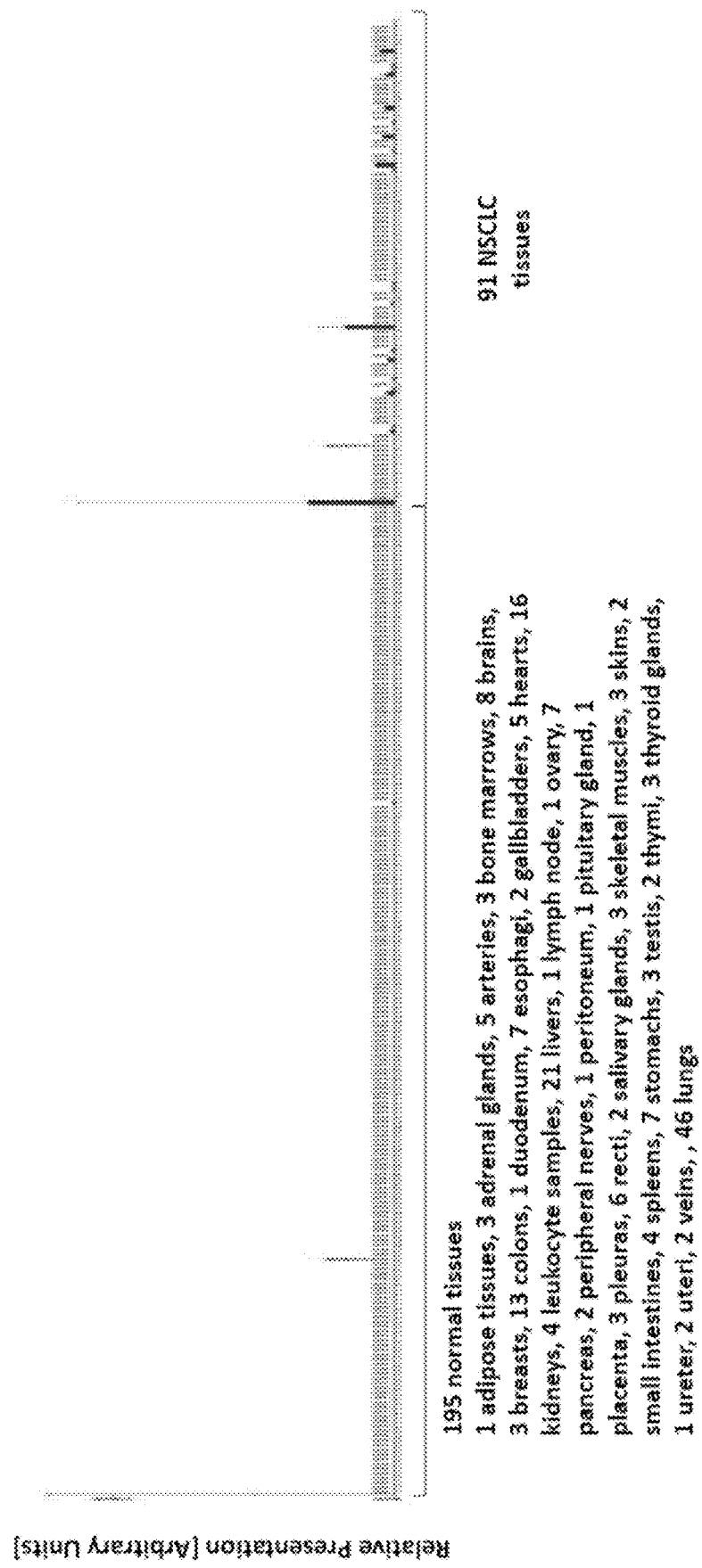

Peptide: FLFDGSANL (A*02) SEQ ID NO: 13

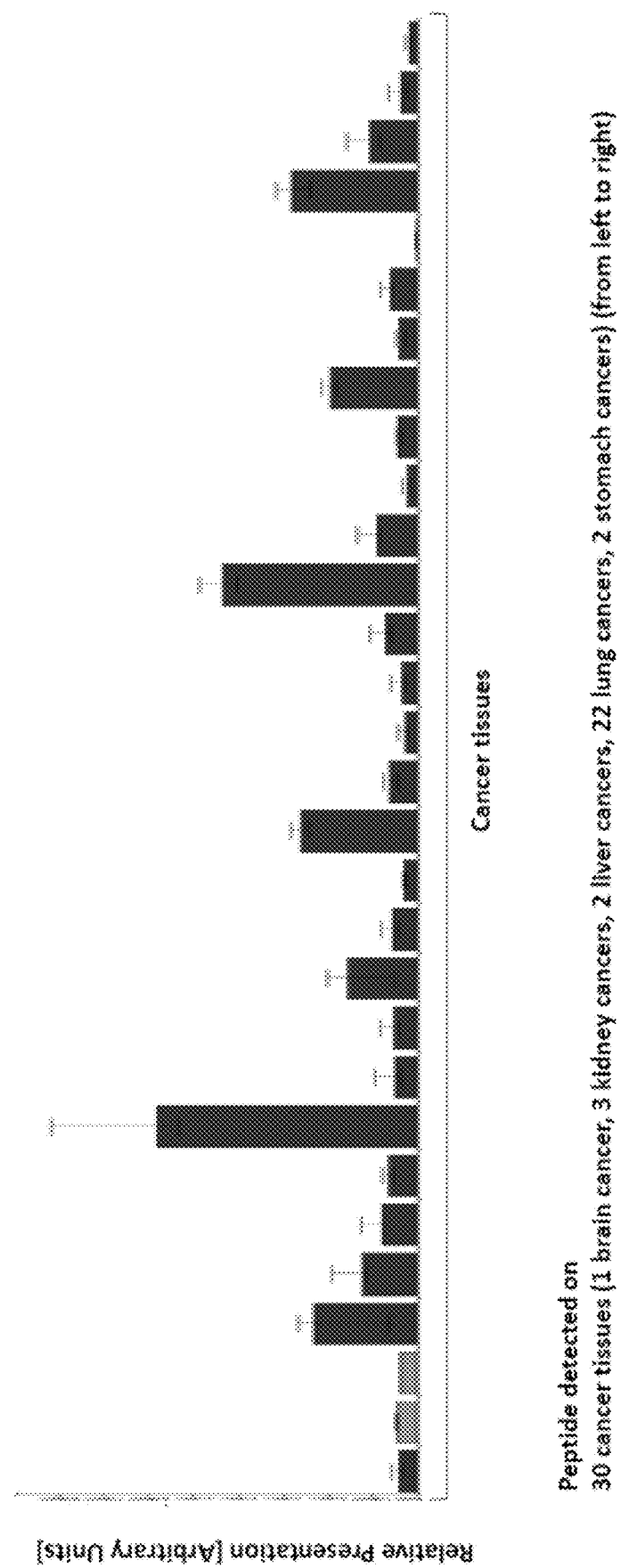

Gene: SMC4

Gene: LAMB3

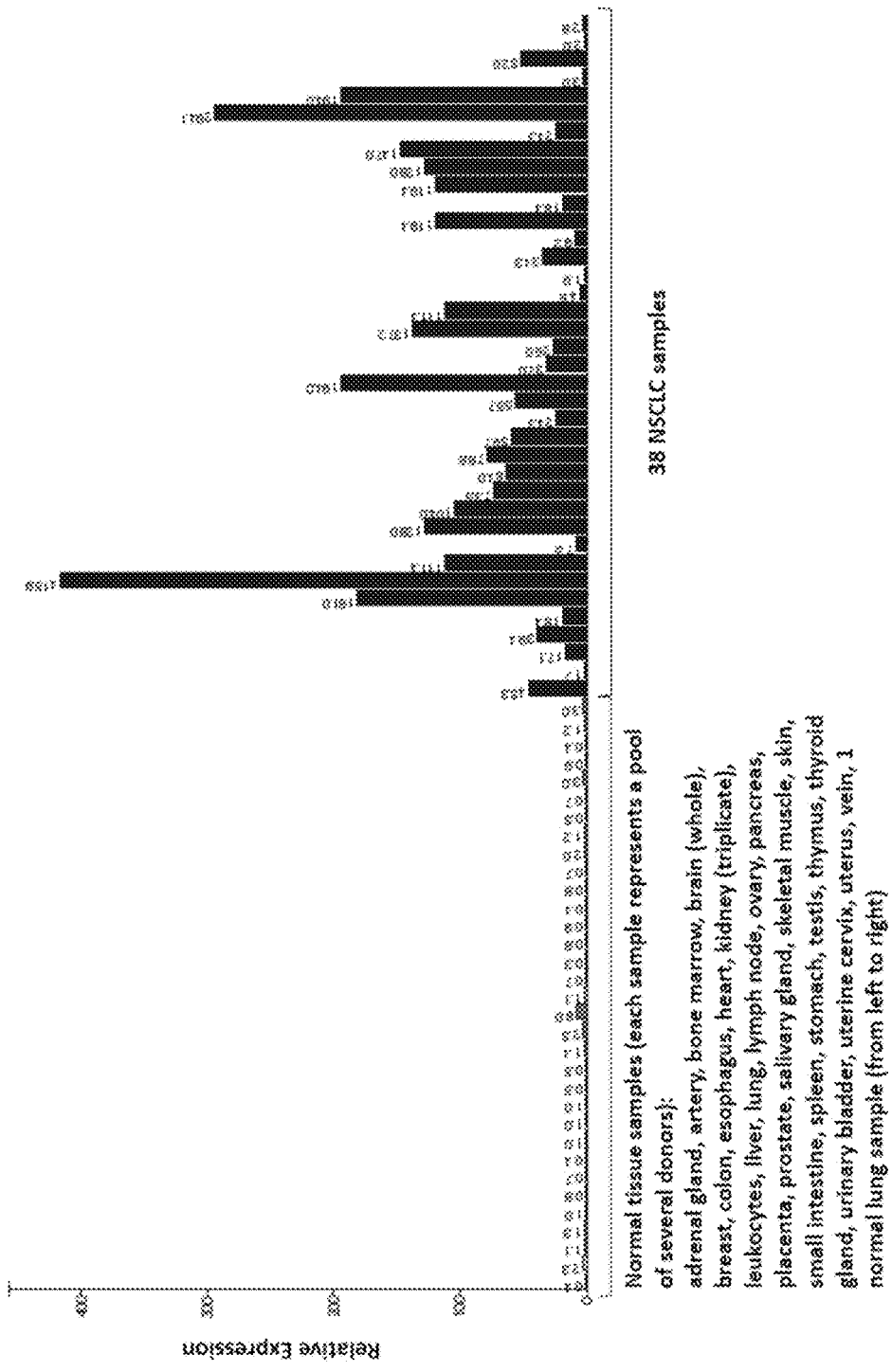

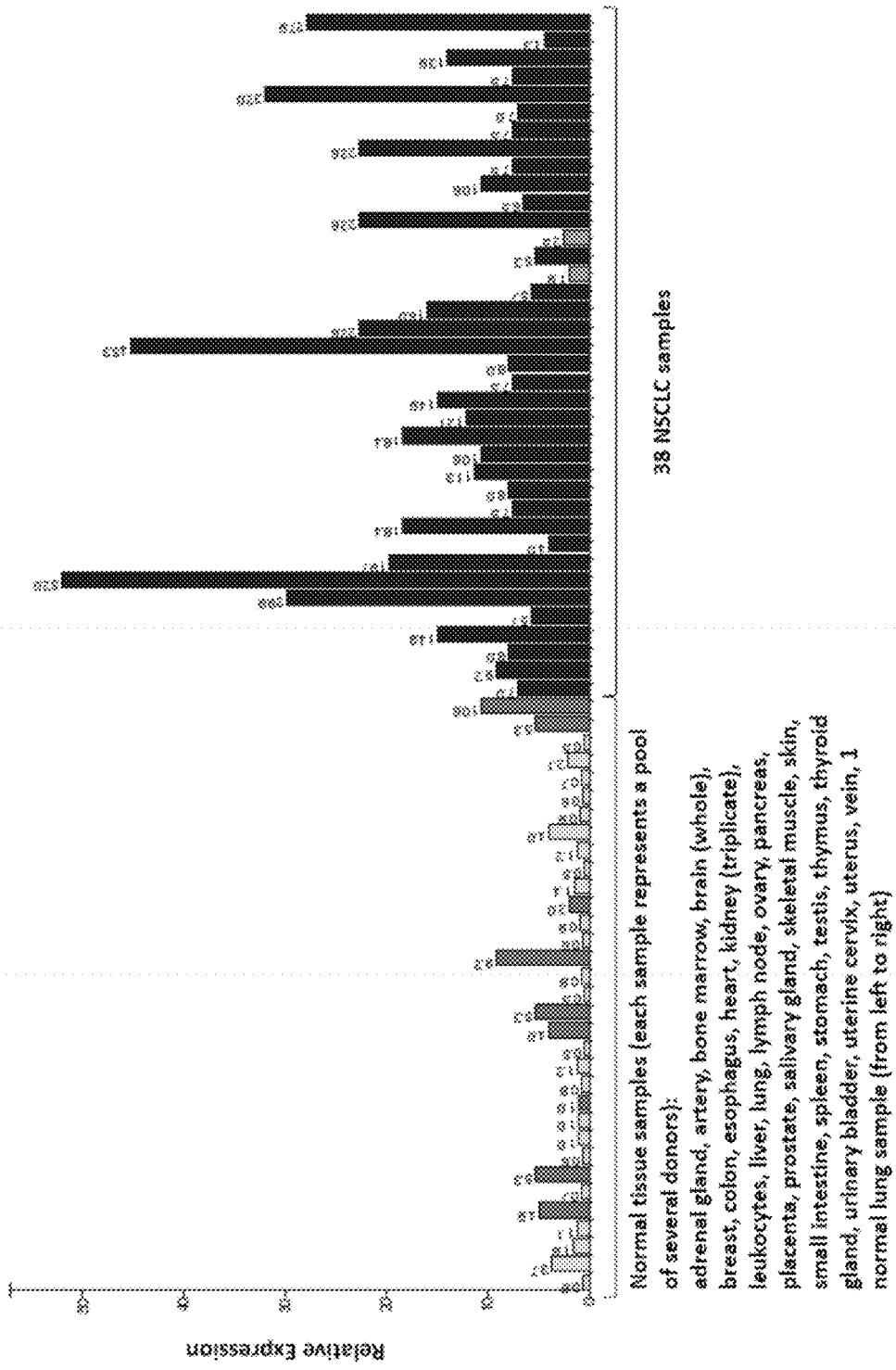
Figure 2D Gene: CENPN

PEPTIDES AND COMBINATION OF PEPTIDES FOR USE IN IMMUNOTHERAPY AGAINST LUNG CANCER, INCLUDING NSCLC AND OTHER CANCERS

CROSS-REFERENCE TO RELATED APPLICATIONS

This application is a Continuation application of U.S. patent application Ser. No. 16/305,686, filed Nov. 29, 2018, which is a National Stage entry of International Application No. PCT/EP2016/059053, filed Apr. 22, 2016, which claims priority to Great Britain Patent Application No. 1507030.3, filed Apr. 24, 2015, and U.S. Provisional Patent Application 62/152,258, filed Apr. 24, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-044006_ST25.txt" created on 29 Jun. 2020, and 29,080 bytes in size) is submitted concurrently with the instant application, and the entire contents of the Sequence Listing are incorporated herein by reference.

BACKGROUND

Field

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I and HLA class II molecules of human tumor cells that can be used in vaccine compositions for eliciting anti-tumor immune responses, or as targets for the development of pharmaceutically/immunologically active compounds and cells.

Description of Related Art

Lung cancer accounts for the most cancer-related deaths in both men and women. Worldwide, lung cancer is the most common cancer in terms of both incidence and mortality. In 2012, there were more than 1.8 million new cases (13% of total cancer incidence), and 1.6 million deaths (20% of total cancer mortality) due to lung cancer. Lung cancer is the leading cause of cancer death in men in 87 countries and in women in 26 countries. More than one third of all newly diagnosed cases occurred in China. The highest rates are in North America, Europe, and East Asia (World Cancer Report, 2014).

Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

An estimated 230,000 new cases of lung cancer and 160,000 deaths due to lung cancer are expected in 2013 in the USA according to the national cancer institute (NCI).

Historically, small cell lung carcinoma has been distinguished from non-small cell lung carcinoma (NSCLC), which includes the histological types of adenocarcinoma, squamous cell carcinoma, and large cell carcinoma. However, in the past decade, the distinction between adenocarcinoma and squamous cell carcinoma has been increasingly recognized because of major differences in genetics and also in responses to specific therapies. Therefore, lung cancers are increasingly classified according to molecular subtypes, predicated on particular genetic alterations that drive and maintain lung tumorigenesis (Travis et al., 2013).

Prognosis is generally poor. Of all people with lung cancer, 10-15% survive for five years after diagnosis. Poor survival of lung cancer patients is due, at least in part, to 80% of patients being diagnosed with metastatic disease and more than half of patients having distant metastases (SEER Stat facts, 2014). At presentation, 30-40% of cases of NSCLC are stage IV, and 60% of SCLC are stage IV.

The 1-year relative survival for lung cancer has slightly increased from 35% in 1975-1979 to 44% in 2010, largely due to improvements in surgical techniques and combined therapies. However, the 5-year survival rate for all stages combined is only 17%. The survival rate is 54% for cases detected when the disease is still localized; however, only 16% of lung cancers are diagnosed at this early stage (SEER Stat facts, 2014).

Treatment options are determined by the type (small cell or non-small cell) and stage of cancer and include surgery, radiation therapy, chemotherapy, and targeted biological therapies such as bevacizumab (AVASTIN®) and erlotinib (TARCEVA®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer; on this regimen, a large percentage of patients experience remission, which is long lasting in some cases surgery (S3-Leitlinie Lungenkarzinom, 2011).

Advanced lung cancer has also been resistant to traditional chemotherapy. However, recent advances have led to exciting progress in therapies that are dependent on histology and genetics. The level of scrutiny is exemplified by trials of adjuvant chemotherapy designed to differentiate not only between mutations in codons 12 and 13 of KRAS, but also between different amino acid substitutions as determined by particular mutations at codon 12 (Shepherd et al., 2013).

To expand the therapeutic options for NSCLC, different immunotherapeutic approaches have been studied or are still under investigation. While vaccination with L-BLP25 or MAGEA3 failed to demonstrate a vaccine-mediated survival advantage in NSCLC patients, an allogeneic cell line-derived vaccine showed promising results in clinical studies. Additionally, further vaccination trials targeting gangliosides, the epidermal growth factor receptor and several other antigens are currently ongoing. An alternative strategy to enhance the patient's anti-tumor T cell response consists of blocking inhibitory T cell receptors or their ligands with specific antibodies. The therapeutic potential of several of these antibodies, including ipilimumab, nivolumab, pembrolizumab, MPDL3280A and MEDI-4736, in NSCLC is currently evaluated in clinical trials (Reinmuth et al., 2015).

Considering the severe side-effects and expense associated with treating cancer, there is a need to identify factors that can be used in the treatment of cancer in general and lung cancer, including NSCLC in particular. There is also a need to identify factors representing biomarkers for cancer in general and lung cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor-associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anti-cancer response by breaking previously established tolerance. Prominent examples for this class of TAAs are Her-2/neu, survivin, telomerase, or WT1.

d) Tumor-specific antigens: These unique TAAs arise from mutations of normal genes (such as beta-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor- (-associated) exon in case of proteins with tumor-specific (-associated) isoforms.

e) TAAs arising from abnormal post-translational modifications: Such TAAs may arise from proteins which are neither specific nor over-expressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T cell-based immunotherapy targets peptide epitopes derived from tumor-associated or tumor-specific proteins, which are presented by molecules of the major histocompatibility complex (MHC). The antigens that are recognized by the tumor-specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRiPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen-presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive helper T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T cell epitopes derived from tumor-associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T helper cells, activated by MHC class II epitopes, play an important role in orchestrating the effector function of CTLs in anti-tumor immunity. T helper cell epitopes that trigger a T helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFN-gamma) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC molecule and specific polymorphisms of the amino acid sequence of the peptide. MHC class I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor-associated antigen, leads to an in vitro or in vivo T cell response.

Basically, any peptide able to bind an MHC molecule may function as a T-cell epitope. A prerequisite for the induction of an in vitro or in vivo T cell response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY

In a first aspect of the present invention, the present invention relates to a peptide comprising an amino acid sequence selected from the group consisting of SEQ ID NO: 1 to SEQ ID NO: 110 or a variant sequence thereof which is at least 77%, preferably at least 88%, homologous (preferably at least 77% or at least 88% identical) to SEQ ID NO: 1 to SEQ ID NO: 110, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 162, preferably of SEQ ID NO: 1 to SEQ ID NO: 110 or a variant thereof, which is at least 77%, preferably at least 88%, homologous (preferably at least 77% or at least 88% identical) to SEQ ID NO: 1 to SEQ ID NO: 110, wherein said peptide or variant thereof has an overall length of between 8 and 100, preferably between 8 and 30, and most preferred of between 8 and 20 amino acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D show the over-presentation of various peptides in normal tissues and NSCLC samples; FIGS. 1E-1G show all cell lines, normal tissues and cancers tissues where the exemplary peptides (FVFSFPVSV, SEQ ID NO: 4 (A*02) and YYTKGFALLNF, SEQ ID NO: 29 (A*24)) has been detected. FIG. 1A—Gene: SLC6A14, Peptide: FLIPYAIML (A*02; SEQ ID NO.:2)—Tissues from left to right: 1 adipose tissues, 3 adrenal glands, 5 arteries, 3 bone marrows, 8 brains, 3 breasts, 13 colons, 1 duodenum, 7 esophagi, 2 gallbladders, 5 hearts, 16 kidneys, 4 leukocyte samples, 21 livers, 1 lymph node, 1 ovary, 7 pancreas, 2 peripheral nerves, 1 peritoneum, 1 pituitary gland, 1 placenta, 3 pleuras, 6 recti, 2 salivary glands, 3 skeletal muscles, 3 skins, 2 small intestines, 4 spleens, 7 stomachs, 3 testis, 2 thymi, 3 thyroid glands, 1 ureter, 2 uteri, 2 veins, 46 lungs, 91 NSCLC. The peptide was also found on pancreatic cancer, gastric cancer, colorectal cancer, esophageal cancer (not shown). FIG. 1B—Gene: COL6A3, Peptide: FLFDGSANL (A*02; SEQ ID NO.:13)—Tissues from left to right: 1 adipose tissues, 3 adrenal glands, 5 arteries, 3 bone marrows, 8 brains, 3 breasts, 13 colons, 1 duodenum, 7 esophagi, 2 gallbladders, 5 hearts, 16 kidneys, 4 leukocyte samples, 21 livers, 1 lymph node, 1 ovary, 7 pancreas, 2 peripheral nerves, 1 peritoneum, 1 pituitary gland, 1 placenta, 3 pleuras, 6 recti, 2 salivary glands, 3 skeletal muscles, 3 skins, 2 small intestines, 4 spleens, 7 stomachs, 3 testis, 2 thymi, 3 thyroid glands, 1 ureter, 2 uteri, 2 veins, 46 lungs, 91 NSCLC. The peptide was also found on prostate cancer, breast cancer, colorectal cancer, hepatic cancer, melanoma, ovarian cancer, esophageal cancer, pancreatic cancer, gastric cancer (not shown). FIG. 1C—Gene: CCL18, Peptide: VYTSWQIPQKF (A*24; SEQ ID NO.:23)—Tissues from left to right: 2 adrenal glands, 1 artery, 4 brains, 1 breast, 5 colons, 1 heart, 13 kidneys, 9 livers, 3 pancreas, 1 pituitary gland, 2 recti, 3 skins, 1 spleen, 12 stomachs, 1 thymus, 2 uteri, 9 lungs, 80 NSCLC. The peptide was also found on prostate cancer, gastric cancer (not shown). FIG. 1D—Gene: CENPN, Peptide: RYLDSLKAIVF (A*24; SEQ ID NO.:28)—Tissues from left to right: 2 adrenal glands, 1 artery, 4 brains, 1 breast, 5 colons, 1 heart, 13 kidneys, 9 livers, 3 pancreas, 1 pituitary gland, 2 recti, 3 skins, 1 spleen, 12 stomachs, 1 thymus, 2 uteri, 9 lungs, 80 NSCLC. The peptide was also found on hepatic cancer, gastric cancer, RCC (not shown). FIG. 1E—Gene: DUSP4, Peptide: FVFSFPVSV (A*02; SEQ ID NO.:4)—Tissues from left to right: 5 pancreatic cell lines, 3 skins, 15 normal tissues (2 esophagi, 7 lungs, 3 spleens, 3 stomachs), 126 cancer tissues (1 brain cancer, 2 breast cancers, 5 colon cancers, 5 esophageal cancers, 2 gallbladder cancers, 8 kidney cancers, 5 liver cancers, 58 lung cancers, 11 ovarian cancers, 9 pancreatic cancers, 2 prostate cancers, 1 rectal cancer, 4 skin cancers, 12 stomach cancers, 1 testis cancer). The set of normal tissues was the same as in A-B, but tissues without detection are not shown. FIG. 1F—Gene: PLOD2, Peptide: YYTKGFALLNF (A*24; SEQ ID NO.:29)—Tissues from left to right: 30 cancer tissues (1 brain cancer, 3 kidney cancers, 2 liver cancers, 22 lung cancers, 2 stomach cancers). The set of normal tissues was the same as in C-D, but tissues without detection are not shown. FIG. 1G show the over-presentation of an A*24 peptide in normal tissues and NSCLC samples. Gene: LAMP3, Peptide: RFMDGHITF (A*24; SEQ ID NO.:25)—Tissues from left to right: 2 adrenal glands, 1 artery, 4 brains, 1 breast, 5 colons, 1 heart, 13 kidneys, 9 livers, 3 pancreas, 1 pituitary gland, 2 recti, 3 skins, 1 spleen, 12 stomachs, 1 thymus, 2 uteri, 9 lungs, 80 NSCLC. The peptide was also found on prostate cancer, gastric cancer (not shown).

FIGS. 2A-2D show exemplary expression profiles (relative expression compared to normal kidney) of source genes of the present invention that are highly over-expressed or exclusively expressed in lung cancer in a panel of normal tissues and 38 lung cancer samples. Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein, 1 normal (healthy) lung sample, 38 NSCLC samples. FIG. 2A: SMC4; FIG. 2B: LAMB3; FIG. 2C: MMP12; and FIG. 2D: LAMP3.

FIG. 3A: SLC1A4-001 (SEQ ID No. 12); FIG. 3B: IGF2BP3-001 (SEQ ID No. 120); FIG. 3C: LAMC2-001 (SEQ ID No. 121); FIG. 3D: COL6A3-008 (SEQ ID No. 13); and FIG. 3E: LAMP3-001 (SEQ ID No. 25).

DETAILED DESCRIPTION OF A PREFERRED EMBODIMENT

Figure 1B:
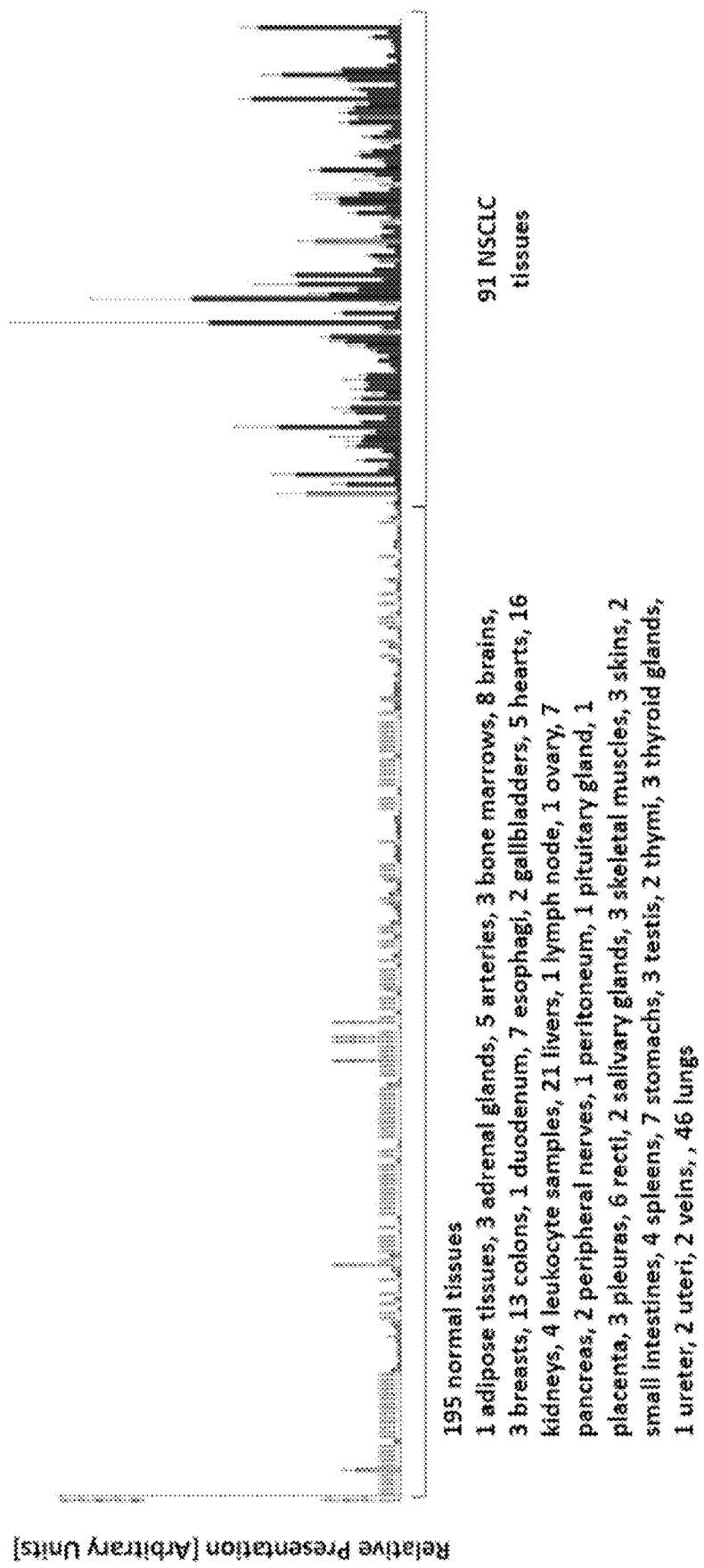
Figure 1C:
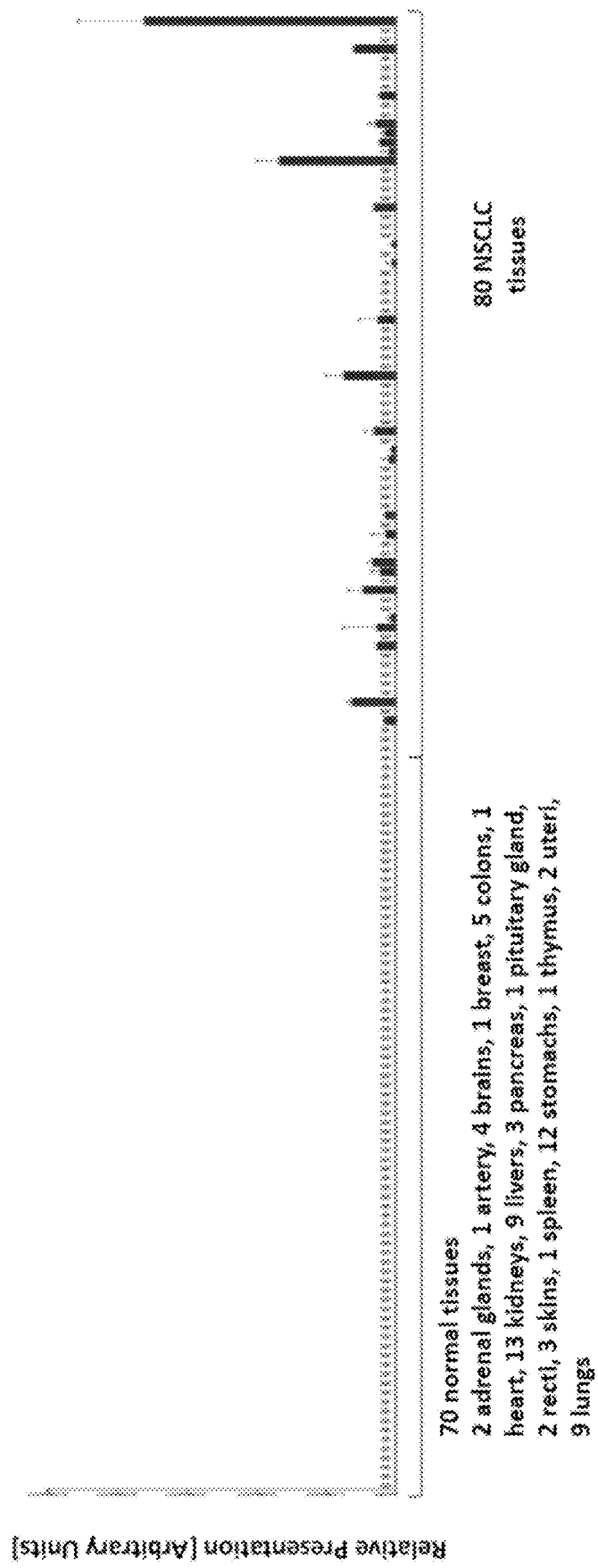
Figure 1D:
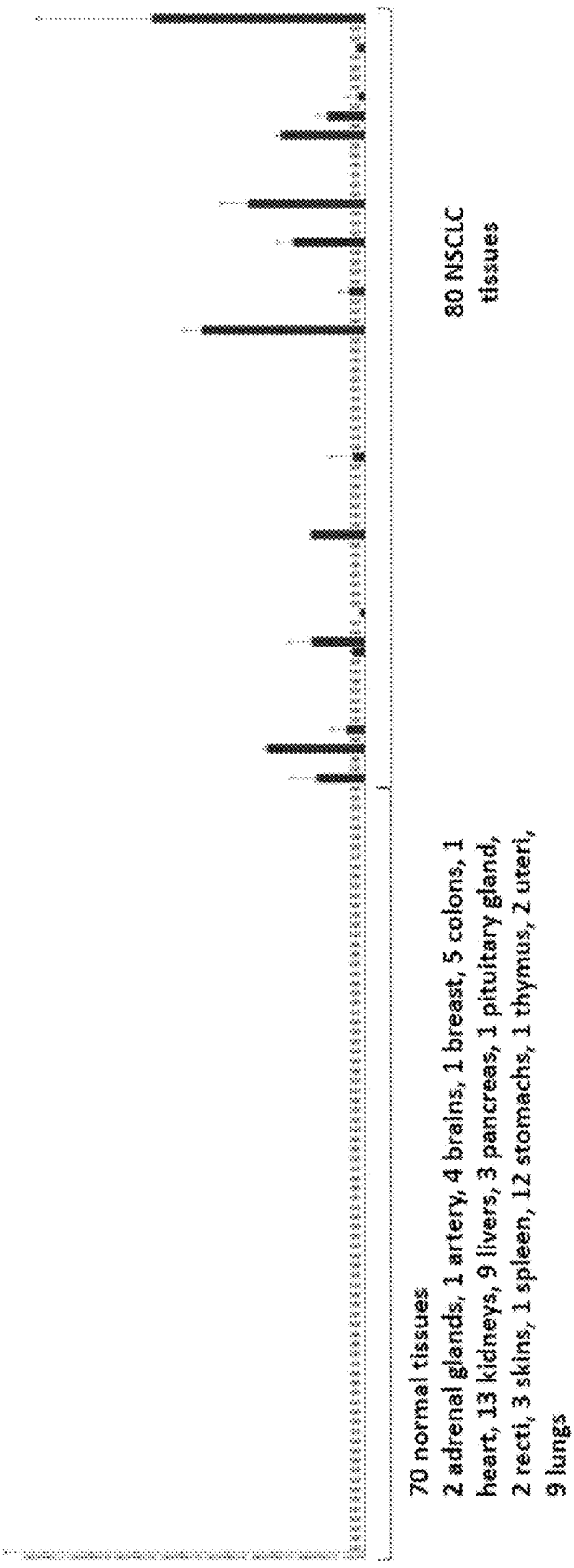
Figure 1E:
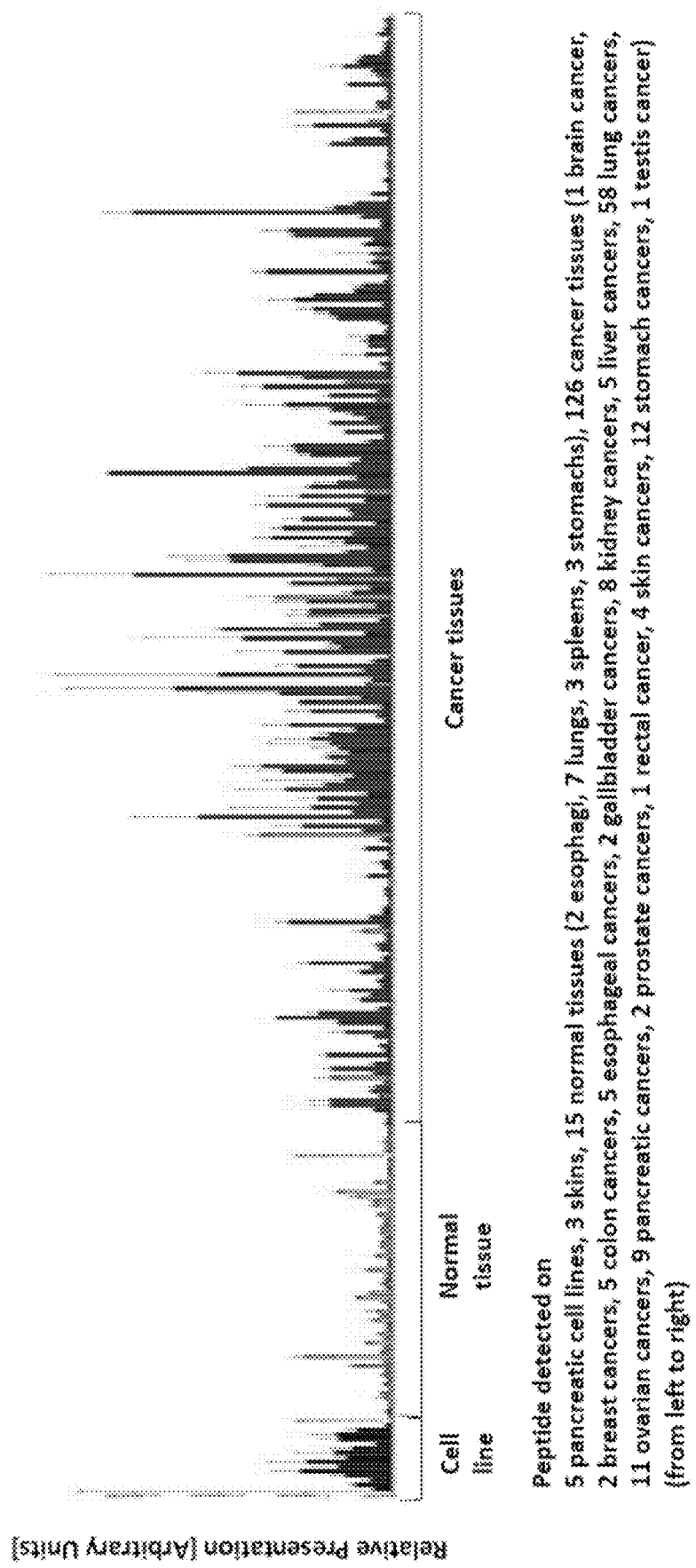
Figure 1G:
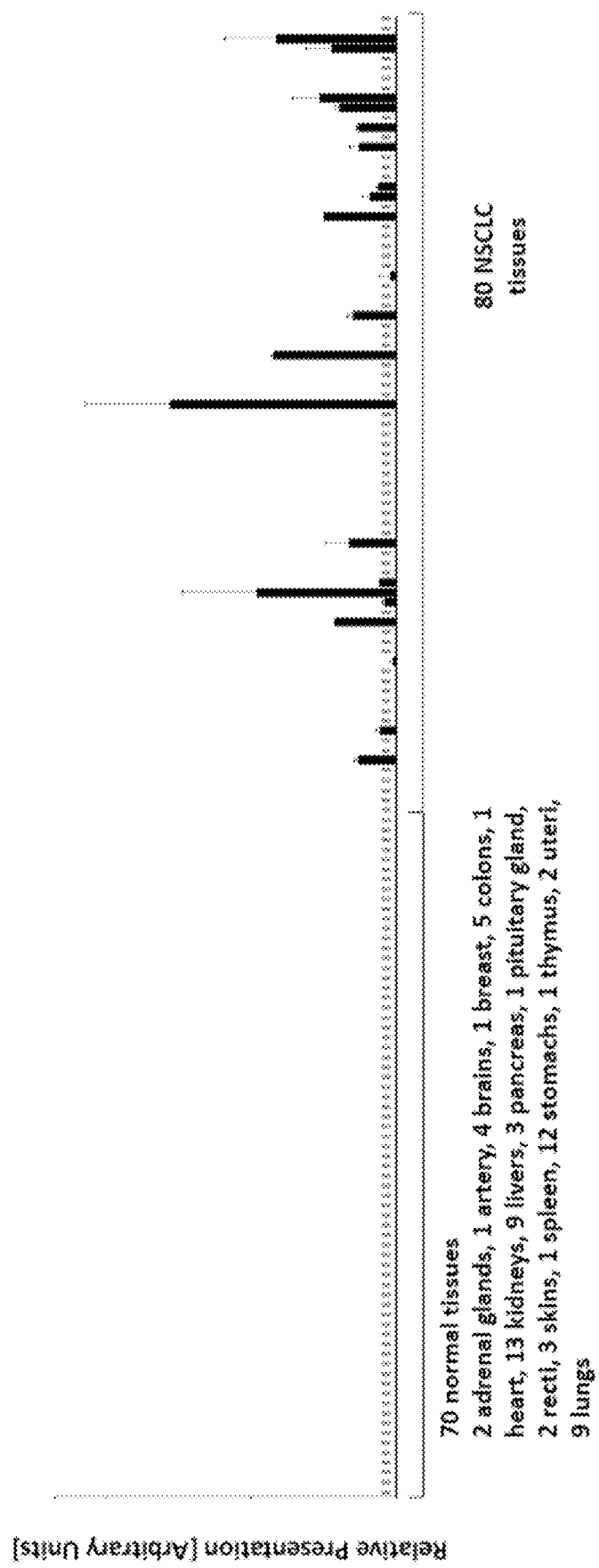

The following tables show the peptides according to the present invention, their respective SEQ ID NOs, and the prospective source (underlying) genes for these peptides. All peptides in Table 1 and Table 4 bind to HLA-A*02. All peptides in Table 2 bind to HLA-A*24. All peptides in Table 3 and Table 5 bind to HLA-DR. The peptides in Table 4 and Table 5 have been disclosed before in large listings as results of high-throughput screenings with high error rates or calculated using algorithms, but have not been associated with cancer at all before. The peptides in Table 6, Table 7, and Table 8 are additional peptides that may be useful in combination with the other peptides of the invention. The peptides in Table 9 and Table 10 are furthermore useful in the diagnosis and/or treatment of various other malignancies that involve an over-expression or over-presentation of the respective underlying polypeptide.

TABLE 1

Peptides according to the present invention

| SEQ ID No | Sequence | Gene ID(s) | Official Gene Symbol(s) |
|---|---|---|---|
| 1 | KLLPYIVGV | 1293 | COL6A3 |
| 2 | FLIPYAIML | 11254 | SLC6A14 |
| 3 | FLYDVVKSL | 1293 | COL6A3 |
| 4 | FVFSFPVSV | 1846 | DUSP4 |
| 5 | ALTSTLISV | 10457 | GPNMB |
| 6 | SLQGSIMTV | 653509, 729238 | SFTPA1, SFTPA2 |
| 7 | NLLQVLEKV | 144501 | KRT80 |
| 8 | ALLNILSEV | 55236 | UBA6 |
| 9 | ALSGTLSGV | 4174 | MCM5 |
| 10 | KMAGIGIREA | 3866 | KRT15 |
| 11 | YLNVQVKEL | 10051 | SMC4 |
| 12 | IVDRTTTVV | 6509 | SLC1A4 |
| 13 | FLFDGSANL | 1293 | COL6A3 |
| 14 | LIQDRVAEV | 3914 | LAMB3 |
| 15 | ELDRTPPEV | 23450 | SF3B3 |
| 16 | LIFDLGGGTFDV | 3303, 3304, 3305, 3306, 3310, 3311, 3312 | HSPA1A, HSPA1B, HSPA1L, HSPA2, HSPA6, HSPA7, HSPA8 |
| 17 | TLLQEQGTKTV | 286887, 3852, 3853, 3854 | KRT6C, KRT5, KRT6A, KRT6B |
| 18 | ILLTEQINL | 10745, 57157 | PHTF1, PHTF2 |
| 19 | VLTSDSPAL | 10457 | GPNMB |
| 20 | LMTKEISSV | 5591 | PRKDC |
| 21 | VLSSGLTAA | 1459 | CSNK2A2 |
| 22 | NLINQEIML | 5783 | PTPN13 |

TABLE 2

Additional Peptides according to the present invention

| SEQ ID No | Sequence | Gene ID(s) | Official Gene Symbol(s) |
|---|---|---|---|
| 23 | VYTSWQIPQKF | 101060271, 6362 | CCL18 |
| 24 | NYPKSIHSF | 4321 | MMP12 |
| 25 | RFMDGHITF | 27074 | LAMP3 |
| 26 | RYLEKFYGL | 4321 | MMP12 |
| 27 | RYPPPVREF | 1293 | COL6A3 |
| 28 | RYLDSLKAIVF | 55839 | CENPN |
| 29 | YYTKGFALLNF | 5352 | PLOD2 |
| 30 | KYLEKYYNL | 4312 | MMP1 |
| 31 | SYLDKVRAL | 3858, 3859, 3860, 3861, 3866, 3868, 3872, 3880 | KRT10, KRT12, KRT13, KRT14, KRT15, KRT16, KRT17, KRT19 |
| 32 | EYQPEMLEKF | 1293 | COL6A3 |
| 33 | TYSEKTTLF | 94025 | MUC16 |
| 34 | VFMKDGFFYF | 4312 | MMP1 |
| 35 | TYNPEIYVI | 3673 | ITGA2 |
| 36 | YYGNTLVEF | 25903 | OLFML2B |
| 37 | RYLEYFEKI | 79573 | TTC13 |
| 38 | VFLNRAKAVFF | 10457 | GPNMB |
| 39 | KFLEHTNFEF | 1794 | DOCK2 |
| 40 | IYNPSMGVSVL | 5818 | PVRL1 |
| 41 | TYIGQGYII | 60681 | FKBP10 |
| 42 | VYVTIDENNIL | 4363 | ABCC1 |
| 43 | RYTLHINTL | 247 | ALOX15B |
| 44 | IYNQIAELW | 27293 | SMPDL3B |
| 45 | KFLESKGYEF | 9945 | GFPT2 |
| 46 | NYTNGSFGSNF | 1655 | DDX5 |
| 47 | RYISPDQLADL | 2023 | ENO1 |
| 48 | YYYGNTLVEF | 25903 | OLFML2B |
| 49 | QYLFPSFETF | 3824 | KLRD1 |
| 50 | LYIGWDKHYGF | 5685 | PSMA4 |
| 51 | NYLLESPHRF | 9842 | PLEKHM1 |
| 52 | SYMEVPTYLNF | 7805 | LAPTM5 |
| 53 | IYAGQWNDF | 81035 | COLEC12 |
| 54 | AYKDKDISFF | 58486 | ZBED5 |
| 55 | IYPVKYTQTF | 64065 | PERP |
| 56 | RYFPTQALNF | 291, 292, 293, 83447 | SLC25A4, SLC25A5, SLC25A6, SLC25A31 |
| 57 | SYSIGIANF | 1303 | COL12A1 |
| 58 | VYFKPSLTPSGEF | 9972 | NUP153 |
| 59 | HYFNTPFQL | 160760 | PPTC7 |
| 60 | SYPAKLSFI | 4029 | L1RE1 |
| 61 | RYGSPINTF | 647024 | C6orf132 |
| 62 | AYKPGALTF | 84883 | AIFM2 |
| 63 | LYINKANIW | 55632 | G2E3 |
| 64 | VYPLALYGF | 9213 | XPR1 |
| 65 | IYQRWKDLL | 219285 | SAMD9L |
| 66 | DYIPQLAKF | 2744 | GLS |
| 67 | IFLDYEAGHLSF | 81559 | TRIM11 |
| 68 | RYLFVVDRL | 55686 | MREG |
| 69 | TYAALNSKATF | 8826 | IQGAP1 |
| 70 | VYHSYLTIF | 7226 | TRPM2 |
| 71 | TYLTNHLRL | 90874 | ZNF697 |
| 72 | YYVDKLFNTI | 5922 | RASA2 |
| 73 | RYLHVEGGNF | 3516 | RBPJ |
| 74 | EYLPEFLHTF | 154664 | ABCA13 |
| 75 | AYPDLNEIYRSF | 11262 | SP140 |
| 76 | VYTZIQSRF | 8445, 8798 | DYRK2, DYRK4 |
| 77 | RYLEAGAAGLRW | 23640 | HSPBP1 |
| 78 | IYTRVTYYL | 64499, 7177 | TPSB2, TPSAB1 |
| 79 | RYGGSFAEL | 23135 | KDM6B |
| 80 | AYLKEVEQL | 8087 | FXR1 |
| 81 | KYIEAIQWI | 81501 | DCSTAMP |
| 82 | FYQGIVQQF | 10426 | TUBGCP3 |
| 83 | EYSDVLAKLAF | 27245 | AHDC1 |
| 84 | TFDVAPSRLDF | 23420, 283820, 408050 | NOMO1, NOMO2, NOMO3 |
| 85 | PFLQASPHF | 84985 | FAM83A |

TABLE 3

HLA-DR peptides according to the present invention

| SEQ ID No | Sequence | Gene ID(s) | Official Gene Symbol(s) |
|---|---|---|---|
| 86 | LSADDIRGIQSLYGDPK | 4321 | MMP12 |
| 87 | EGDIQQFLITGDPKAAYDY | 1301 | COL11A1 |
| 88 | NPVSQVEILKNKPLSVG | 3694 | ITGB6 |
| 89 | KLYIGNLSENAAPS | 10643 | IGF2BP3 |
| 90 | DAVQMVITEAQKVDTR | 3918 | LAMC2 |
| 91 | VARLPIIDLAPVDVGGTD | 1290 | COL5A2 |
| 92 | NKPSRLPFLDIAPLDIGGAD | 1278 | COL1A2 |
| 93 | SRPQAPITGYRIVYSPSV | 2335 | FN1 |

TABLE 4

Additional peptides according to the present invention with no prior known cancer association

| SEQ ID No | Sequence | Gene ID(s) | Official Gene Symbol(s) |
|---|---|---|---|
| 94 | ILVDWLVQV | 9133 | CCNB2 |
| 95 | KIIGIMEEV | 2956 | MSH6 |
| 96 | AMGIAPPKV | 9129 | PRPF3 |
| 97 | TLFPVRLLV | 79888 | LPCAT1 |
| 98 | VLYPHEPTAV | 29980, 5523 | DONSON, PPP2R3A |
| 99 | ALFQRPPLI | 1736 | DKC1 |
| 100 | KIVDFSYSV | 701 | BUB1B |
| 101 | LLLEILHEI | 30001 | ERO1L |
| 102 | SLLSELQHA | 115362 | GBP5 |
| 103 | KLLSDPNYGV | 79188 | TMEM43 |
| 104 | SLVAVELEKV | 25839 | COG4 |

TABLE 4-continued

Additional peptides according to the present invention with no prior known cancer association

| SEQ ID No | Sequence | Gene ID(s) | Official Gene Symbol(s) |
|---|---|---|---|
| 105 | IVAESLQQV | 6772 | STAT1 |
| 106 | SILEHQIQV | 4173 | MCM4 |
| 107 | ALSERAVAV | 10213 | PSMD14 |
| 108 | TLLDFINAV | 55236 | UBA6 |
| 109 | NLIEVNEEV | 221960, 51622 | CCZ1B, CCZ1 |

TABLE 5

Additional HLA-DR peptides according to the present invention with no prior known cancer association

| SEQ ID No | Sequence | Gene ID(s) | Official Gene Symbol(s) |
|---|---|---|---|
| 110 | IQLIVQDKESVFSPR | 27074 | LAMP3 |

TABLE 6

Other peptides useful for e.g. personalized cancer therapies

| SEQ ID No | Sequence | Gene ID(s) | Official Gene Symbol(s) |
|---|---|---|---|
| 111 | SLYKGLLSV | 25788 | RAD54B |
| 112 | VLAPLFVYL | 2535, 8321, 8324 | FZD2, FZD1, FZD7 |
| 113 | FLLDGSANV | 1293 | COL6A3 |
| 114 | AMSSKFFLV | 7474 | WNT5A |
| 115 | YVYQNNIYL | 2191 | FAP |
| 116 | KIQEMQHFL | 4321 | MMP12 |
| 117 | ILIDWLVQV | 891 | CCNB1 |
| 118 | SLHFLILYV | 487,488 | ATP2A1, ATP2A2 |
| 119 | IVDDITYNV | 2335 | FN1 |
| 120 | KIQEILTQV | 10643 | IGF2BP3 |
| 121 | RLLDSVSRL | 3918 | LAMC2 |
| 122 | KLSWDLIYL | 51148 | CERCAM |
| 123 | GLTDNIHLV | 25878 | MXRA5 |
| 124 | NLLDLDYEL | 1293 | COL6A3 |
| 125 | RLDDLKMTV | 3918 | LAMC2 |
| 126 | KLLTEVHAA | 101 | ADAM8 |
| 127 | ILFPDIIARA | 64110 | MAGEF1 |
| 128 | TLSSIKVEV | 25878 | MXRA5 |
| 129 | GLIEIISNA | 23020 | SNRNP200 |
| 130 | KILEDVVGV | 22974 | TPX2 |
| 131 | ALVQDLAKA | 891 | CCNB1 |
| 132 | ALFVRLLALA | 7045 | TGFBI |
| 133 | RLASYLDKV | 3857, 3858, 3859, 3860, 3861, 3866, 3868, 3872, 3880 | KRT9, KRT10, KRT12, KRT13, KRT14, KRT15, KRT16, KRT17, KRT19 |
| 134 | TLWYRAPEV | 1019,1021 | CDK4,CDK6 |
| 135 | AIDGNNHEV | 9945 | GFPT2 |
| 136 | ALVDHTPYL | 1462 | VCAN |
| 137 | FLVDGSWSV | 1303 | COL12A1 |
| 138 | ALNEEAGRLLL | 27338 | UBE2S |
| 139 | SLIEDLILL | 64754 | SMYD3 |
| 140 | TLYPHTSQV | 1462 | VCAN |
| 141 | NLIEKSIYL | 667 | DST |
| 142 | VLLPVEVATHYL | 10568 | SLC34A2 |
| 143 | AIVDKVPSV | 22820 | COPG1 |
| 144 | KIFDEILVNA | 7153, 7155 | TOP2A, TOP2B |
| 145 | AMTQLLAGV | 3371 | TNC |
| 146 | FQYDHEAFL | 57333, 5954 | RCN3, RCN1 |
| 147 | VLFPNLKTV | 646 | BNC1 |
| 148 | ALFGALFLA | 5360 | PLTP |
| 149 | KLVEFDFLGA | 10460 | TACC3 |
| 150 | GVLENIFGV | 399909 | PCNXL3 |
| 151 | AVVEFLTSV | 29102 | DROSHA |

TABLE 6-continued

Other peptides useful for e.g. personalized cancer therapies

| SEQ ID No | Sequence | Gene ID(s) | Official Gene Symbol(s) |
|---|---|---|---|
| 152 | ILQDRLNQV | 990 | CDC6 |
| 153 | ALYDSVILL | 1734 | DIO2 |
| 154 | ILFEINPKL | 154664 | ABCA13 |
| 155 | ALDENLHQL | 154664 | ABCA13 |
| 156 | TVAEVIQSV | 55083 | KIF26B |
| 157 | KLFGEKTYL | 6317 | SERPINB3 |
| 158 | KLDETNNTL | 667 | DST |

TABLE 7

Other peptides useful for e.g. personalized cancer therapies

| SEQ ID No | Sequence | Gene ID(s) | Official Gene Symbol(s) |
|---|---|---|---|
| 159 | TYKYVDINTF | 4321 | MMP12 |
| 160 | SYLQAANAL | 1293 | COL6A3 |
| 161 | LYQILQGIVF | 983 | CDK1 |

TABLE 8

HLA-DR peptides useful for e.g. personalized cancer therapies

| SEQ ID No | Sequence | Gene ID(s) | Official Gene Symbol(s) |
|---|---|---|---|
| 162 | TNGVIHVVDKLLYPADT | 10631 | POSTN |

The present invention furthermore generally relates to the peptides according to the present invention for use in the treatment of proliferative diseases, such as, for example, brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), esophageal cancer including cancer of the gastric-esophageal junction (OSCAR), gallbladder cancer and cholangiocarcinoma (GBC_CCC), urinary bladder cancer (UBC), uterine cancer (UEC).

Particularly preferred are the peptides—alone or in combination—according to the present invention selected from the group consisting of SEQ ID NO: 1 to SEQ ID NO: 110. More preferred are the peptides—alone or in combination—selected from the group consisting of SEQ ID NO: 1 to SEQ ID NO: 14 (see Table 1) and SEQ ID NO: 23 to SEQ ID NO: 47 (see Table 2), and their uses in the immunotherapy of lung cancer (including NSCLC), brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), esophageal cancer including cancer of the gastric-esophageal junction (OSCAR), gallbladder cancer and cholangiocarcinoma (GBC_CCC), urinary bladder cancer (UBC), uterine cancer (UEC), and preferably lung cancer, including NSCLC.

As shown in the following Table 9, 9-2, and Table 10 and 10-2, many of the peptides according to the present invention are also found on other tumor types and can, thus, also be used in the immunotherapy of other indications. Also refer to FIG. 1 and Example 1.

TABLE 9

HLA-A*02 peptides according to the present invention and their specific uses in other proliferative diseases, especially in other cancerous diseases. The table shows for selected peptides on which additional tumour types they were found and either over-presented on more than 5% of the measured tumour samples, or presented on more than 5% of the measured tumour samples with a ratio of geometric means tumour vs normal tissues being larger than 3.

| SEQ ID No. | Sequence | Other relevant organs/diseases |
|---|---|---|
| 1 | KLLPYIVGV | Pancreas, Breast |
| 2 | FLIPYAIML | Stomach, Colon, Rectum, Pancreas |
| 3 | FLYDVVKSL | Pancreas, Breast |
| 4 | FVFSFPVSV | Stomach, Pancreas, Breast, Melanoma, Ovary |
| 5 | ALTSTLISV | Breast, Melanoma, Esophagus |
| 7 | NLLQVLEKV | Kidney, Colon, Rectum, Liver, Breast |
| 8 | ALLNILSEV | Brain, Liver, Prostate, Ovary |
| 9 | ALSGTLSGV | Brain, Liver, Leukocytes, Melanoma, Ovary, Esophagus |
| 10 | KMAGIGIREA | Prostate, Ovary |
| 11 | YLNVQVKEL | Colon, Rectum, Liver |
| 13 | FLFDGSANL | Colon, Rectum, Pancreas, Breast, Esophagus |
| 14 | LIQDRVAEV | Kidney |
| 15 | ELDRTPPEV | Kidney, Brain, Liver, Leukocytes |
| 16 | LIFDLGGGTFDV | Brain, Liver, Prostate, Breast, Melanoma, Ovary |
| 18 | ILLTEQINL | Kidney, Stomach, Liver, Pancreas, Prostate, Breast, Ovary, Esophagus |
| 19 | VLTSDSPAL | Liver, Melanoma, Esophagus |
| 20 | LMTKEISSV | Brain, Liver, Melanoma |
| 21 | VLSSGLTAA | Liver, Esophagus |
| 94 | ILVDWLVQV | Kidney, Brain, Stomach, Colon, Rectum, Liver, Melanoma, Ovary |
| 95 | KIIGIMEEV | Kidney, MCC, Esophagus |
| 96 | AMGIAPPKV | Colon, Rectum, Liver, Pancreas, Leukocytes |
| 97 | TLFPVRLLV | Kidney, Leukocytes |
| 98 | VLYPHEPTAV | Kidney, Brain, Colon, Rectum, Liver, MCC, Melanoma, Ovary |
| 99 | ALFQRPPLI | Colon, Rectum, Liver, Ovary |
| 100 | KIVDFSYSV | Brain, Colon, Rectum, MCC, Ovary |
| 101 | LLLEILHEI | Kidney, Liver, Pancreas, Breast, Ovary |
| 102 | SLLSELQHA | Kidney, Breast, Ovary, Esophagus |
| 103 | KLLSDPNYGV | Brain, Pancreas |
| 104 | SLVAVELEKV | Brain, Liver, Pancreas, MCC, Ovary, Esophagus |
| 105 | IVAESLQQV | Kidney, Stomach, Pancreas, Breast, Ovary, Esophagus |
| 106 | SILEHQIQV | Kidney |
| 111 | SLYKGLLSV | Kidney, Brain, Colon, Rectum, Liver, Ovary |
| 112 | VLAPLFVYL | Kidney, Pancreas, Breast, Melanoma |
| 113 | FLLDGSANV | Stomach, Colon, Rectum, Liver, Pancreas, Breast, Ovary, Esophagus |
| 114 | AMSSKFFLV | Brain, Stomach, Colon, Rectum, Liver, Pancreas, Prostate, Ovary, Esophagus |
| 115 | YVYQNNIYL | Stomach, Colon, Rectum, Liver, Pancreas, Breast, Melanoma, Ovary, Esophagus |
| 116 | KIQEMQHFL | Colon, Rectum |
| 117 | ILIDWLVQV | Kidney, Brain, Stomach, Colon, Rectum, Liver, Pancreas, Melanoma, Ovary |
| 118 | SLHFLILYV | Kidney, Brain, Colon, Rectum, Liver, Melanoma, Ovary |
| 119 | IVDDITYNV | Liver, Pancreas, Breast, Esophagus |
| 120 | KIQEILTQV | Kidney, Brain, Stomach, Colon, Rectum, Liver, Pancreas, Leukocytes, Ovary, Esophagus |
| 121 | RLLDSVSRL | Kidney, Colon, Rectum, Liver, Pancreas, Ovary |
| 122 | KLSWDLIYL | Kidney, Colon, Rectum |
| 123 | GLTDNIHLV | Kidney, Colon, Rectum, Pancreas, Ovary, Esophagus |
| 124 | NLLDLDYEL | Stomach, Colon, Rectum, Pancreas, Breast, Ovary, Esophagus |
| 125 | RLDDLKMTV | Colon, Rectum, Pancreas, Ovary, Esophagus |
| 126 | KLLTEVHAA | Kidney, Stomach, Colon, Rectum, Liver, Pancreas, Breast, Ovary |
| 127 | ILFPDIIARA | Kidney, Brain, Leukocytes, Esophagus |
| 128 | TLSSIKVEV | Kidney, Stomach, Colon, Rectum, Pancreas, Prostate, Breast, Melanoma, Ovary |
| 129 | GLIEIISNA | Brain, Colon, Rectum, Liver, Ovary, Esophagus |
| 130 | KILEDVVGV | Kidney, Stomach, Colon, Rectum, Melanoma, Ovary, Esophagus |
| 131 | ALVQDLAKA | Kidney, Stomach, Colon, Rectum, Liver, Pancreas, Ovary |
| 132 | ALFVRLLALA | Kidney, Brain, Stomach, Colon, Rectum, Liver, Pancreas, Melanoma, Ovary, Esophagus |
| 133 | RLASYLDKV | Pancreas, Breast, Esophagus |
| 134 | TLWYRAPEV | Stomach, Melanoma, Ovary |
| 135 | AIDGNNHEV | Brain, Liver, Pancreas |
| 136 | ALVDHTPYL | Kidney, Liver, Pancreas |
| 137 | FLVDGSWSV | Stomach, Colon, Rectum, Pancreas, Ovary, Esophagus |
| 138 | ALNEEAGRLLL | Kidney, Brain, Stomach, Colon, Rectum, Liver, Pancreas, MCC, Melanoma, Ovary, Esophagus |
| 139 | SLIEDLILL | Kidney, Brain, Colon, Rectum, Liver, Pancreas, Prostate, Melanoma, Ovary, Esophagus |
| 141 | NLIEKSIYL | Esophagus |
| 142 | VLLPVEVATHYL | Ovary |
| 143 | AIVDKVPSV | Kidney, Liver, Pancreas, Prostate, Ovary, Esophagus |
| 144 | KIFDEILVNA | Stomach, Colon, Rectum, Melanoma, Ovary, Esophagus |
| 145 | AMTQLLAGV | Brain, Colon, Rectum, Breast, Esophagus |
| 146 | FQYDHEAFL | Kidney, Stomach, Colon, Rectum, Pancreas, Melanoma, Esophagus |
| 147 | VLFPNLKTV | Kidney |
| 148 | ALFGALFLA | Melanoma, Ovary |
| 149 | KLVEFDFLGA | Brain, Stomach, Colon, Rectum, Liver, MCC, Ovary, Esophagus |
| 150 | GVLENIFGV | Kidney, Brain, Liver, Ovary, Esophagus |
| 151 | AVVEFLTSV | Brain, MCC, Esophagus |
| 152 | ILQDRLNQV | Colon, Rectum, Liver, Ovary |
| 153 | ALYDSVILL | Stomach, Prostate, Esophagus |
| 155 | ALDENLHQL | Esophagus |
| 156 | TVAEVIQSV | Pancreas, Breast, Esophagus |
| 157 | KLFGEKTYL | Esophagus |

TABLE 9-2

HLA-A*02 peptides according to the present invention and their specific uses in other proliferative diseases, especially in other cancerous diseases (amendment of Table 9). The table shows, like Table 9, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, and urinary bladder.

| SEQ ID No. | Sequence | Additional Entities |
|---|---|---|
| 1 | KLLPYIVGV | SCLC, CRC, Melanoma, Esophageal Cancer, Gallbladder Cancer, Bile Duct Cancer |
| 2 | FLIPYAIML | SCLC, PC, Urinary bladder cancer, Gallbladder Cancer, Bile Duct Cancer |
| 3 | FLYDWKSL | SCLC, CRC, Gallbladder Cancer, Bile Duct Cancer |
| 4 | FVFSFPVSV | SCLC, Esophageal Cancer, Urinary bladder cancer, Gallbladder Cancer, Bile Duct Cancer, NHL |
| 7 | NLLQVLEKV | SCLC, OC, Urinary bladder cancer, Uterine Cancer, Gallbladder Cancer, Bile Duct Cancer |
| 8 | ALLNILSEV | SCLC, BRCA, Esophageal Cancer, Urinary bladder cancer, Uterine Cancer |
| 9 | ALSGTLSGV | CLL, BRCA, Urinary bladder cancer, Uterine Cancer, AML, NHL |
| 10 | KMAGIGIREA | Urinary bladder cancer |
| 11 | YLNVQVKEL | SCLC, Melanoma, Esophageal Cancer, Urinary bladder cancer, Uterine Cancer, Gallbladder Cancer, Bile Duct Cancer, AML |
| 13 | FLFDGSANL | SCLC, GC, Melanoma, OC, Urinary bladder cancer, Gallbladder Cancer, Bile Duct Cancer |
| 14 | LIQDRVAEV | Esophageal Cancer, Urinary bladder cancer |
| 15 | ELDRTPPEV | SCLC, PC, CLL, Esophageal Cancer, Urinary bladder cancer, Uterine Cancer, Gallbladder Cancer, Bile Duct Cancer, AML, NHL |
| 17 | TLLQEQGTKTV | SCLC, Esophageal Cancer, Urinary bladder cancer |
| 18 | ILLTEQINL | SCLC, Melanoma, Gallbladder Cancer, Bile Duct Cancer |
| 20 | LMTKEISSV | OC, Esophageal Cancer, Urinary bladder cancer, Gallbladder Cancer, Bile Duct Cancer |
| 21 | VLSSGLTAA | CRC, BRCA, Urinary bladder cancer, Uterine Cancer |
| 22 | NLINQEIML | BRCA, Melanoma, Urinary bladder cancer |
| 94 | ILVDWLVQV | SCLC, BRCA, Esophageal Cancer, Urinary bladder cancer, Uterine Cancer, Gallbladder Cancer, Bile Duct Cancer, AML, NHL |
| 95 | KIIGIMEEV | SCLC, Brain Cancer, GC, CRC, Melanoma, AML, NHL |
| 96 | AMGIAPPKV | SCLC, BRCA, Melanoma, NHL |
| 98 | VLYPHEPTAV | SCLC, BRCA, Esophageal Cancer, Urinary bladder cancer, NHL |
| 99 | ALFQRPPLI | SCLC, CLL, Esophageal Cancer, Urinary bladder cancer, Gallbladder Cancer, Bile Duct Cancer, NHL |
| 100 | KIVDFSYSV | SCLC, BRCA, Melanoma, Urinary bladder cancer, Uterine Cancer |
| 101 | LLLEILHEI | SCLC, CLL, Urinary bladder cancer |
| 102 | SLLSELQHA | SCLC, Melanoma, Uterine Cancer, Gallbladder Cancer, Bile Duct Cancer, NHL |
| 103 | KLLSDPNYGV | BRCA, Melanoma, Urinary bladder cancer, Gallbladder Cancer, Bile Duct Cancer |
| 105 | IVAESLQQV | SCLC, Melanoma, NHL |
| 106 | SILEHQIQV | CRC, BRCA, Esophageal Cancer, Urinary bladder cancer, Uterine Cancer, AML, NHL |
| 107 | ALSERAVAV | Esophageal Cancer, Uterine Cancer |
| 108 | TLLDFINAV | NHL |
| 109 | NLIEVNEEV | CLL, AML |

SCLC = small cell lung cancer, RCC = kidney cancer, CRC = colon or rectum cancer, GC = stomach cancer, HCC = liver cancer, PC = pancreatic cancer, PrC = prostate cancer, BRCA = breast cancer, MCC = Merkel cell carcinoma, OC = ovarian cancer, NHL = non-Hodgkin lymphoma, AML = acute myeloid leukemia, CLL = chronic lymphocytic leukemia.

TABLE 10

HLA-A*24 peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3.

| SEQ ID No. | Sequence | Other relevant organs / diseases |
|---|---|---|
| 26 | RYLEKFYGL | Stomach, Liver |
| 27 | RYPPPVREF | Liver, Prostate |
| 28 | RYLDSLKAIVF | Kidney, Liver |
| 29 | YYTKGFALLNF | Kidney, Brain, Liver |
| 31 | SYLDKVRAL | Stomach |
| 33 | TYSEKTTLF | Stomach |
| 36 | YYGNTLVEF | Brain, Stomach |
| 37 | RYLEYFEKI | Brain, Liver, Prostate |
| 38 | VFLNRAKAVFF | Liver |
| 39 | KFLEHTNFEF | Liver |
| 41 | TYIGQGYII | Brain, Stomach, Liver, Prostate |
| 42 | VYVTIDENNIL | Kidney, Stomach |
| 43 | RYTLHINTL | Prostate |
| 44 | IYNQIAELW | Stomach, Liver |
| 45 | KFLESKGYEF | Brain |
| 46 | NYTNGSFGSNF | Liver |
| 47 | RYISPDQLADL | Kidney |
| 49 | QYLFPSFETF | Stomach |
| 50 | LYIGWDKHYGF | Kidney, Stomach, Liver |
| 51 | NYLLESPHRF | Liver |
| 52 | SYMEVPTYLNF | Liver |
| 53 | IYAGQWNDF | Prostate |
| 54 | AYKDKDISFF | Kidney, Brain |
| 56 | RYFPTQALNF | Kidney, Stomach, Liver |
| 58 | VYFKPSLTPSGEF | Stomach, Liver |
| 59 | HYFNTPFQL | Kidney, Brain, Liver, Prostate |
| 60 | SYPAKLSFI | Liver |
| 61 | RYGSPINTF | Liver, Prostate |
| 62 | AYKPGALTF | Liver |
| 63 | LYINKANIW | Stomach, Liver |
| 66 | DYIPQLAKF | Kidney, Liver |
| 67 | IFLDYEAGHLSF | Kidney, Stomach, Liver, Prostate |
| 69 | TYAALNSKATF | Liver |
| 70 | VYHSYLTIF | Brain, Liver |
| 71 | TYLTNHLRL | Liver |
| 72 | YYVDKLFNTI | Liver, Prostate |

TABLE 10-continued

HLA-A*24 peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3.

| SEQ ID No. | Sequence | Other relevant organs / diseases |
|---|---|---|
| 73 | RYLHVEGGNF | Brain, Liver |
| 75 | AYPDLNEIYRSF | Liver |
| 76 | VYTZIQSRF | Liver, Prostate |
| 77 | RYLEAGAAGLRW | Stomach, Liver |
| 78 | IYTRVTYYL | Stomach, Prostate |
| 79 | RYGGSFAEL | Brain, Liver |
| 80 | AYLKEVEQL | Brain, Prostate |
| 81 | KYIEAIQWI | Liver |
| 82 | FYQGIVQQF | Brain, Liver, Prostate |
| 84 | TFDVAPSRLDF | Liver, Prostate |
| 85 | PFLQASPHF | Stomach |
| 159 | TYKYVDINTF | Stomach |
| 160 | SYLQAANAL | Stomach |
| 161 | LYQILQGIVF | Kidney, Stomach, Liver |

TABLE 10-2

HLA-A*24 peptides according to the present invention and their specific uses in other proliferative diseases, especially in other cancerous diseases (amendment of Table 10). The table shows, like Table 10, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adrenal gland, artery, brain, heart, kidney, large intestine, liver, lung, pancreas, pituitary, skin, spleen, stomach, thymus.

| SEQ ID No. | Sequence | Additional Entities |
|---|---|---|
| 27 | RYPPPVREF | Brain Cancer |
| 32 | EYQPEMLEKF | Brain Cancer |
| 40 | IYNPSMGVSVL | Brain Cancer |
| 46 | NYTNGSFGSNF | Brain Cancer |
| 47 | RYISPDQLADL | HCC |
| 48 | YYYGNTLVEF | Brain Cancer |
| 57 | SYSIGIANF | Brain Cancer |
| 61 | RYGSPINTF | GC |
| 67 | IFLDYEAGHLSF | Brain Cancer |
| 72 | YYVDKLFNTI | Brain Cancer |
| 76 | VYTZIQSRF | Brain Cancer |

GC = stomach cancer, HCC = liver cancer.

Thus, another aspect of the present invention relates to the use of at least one peptide according to the present invention according to any one of SEQ ID No. 7, 14, 15, 18, 94, 95, 97, 98, 101, 102, 105, 106, 111, 112, 117, 118, 120, 121, 122, 123, 126, 127, 128, 130, 131, 132, 136, 138, 139, 143, 146, 147, 150, 28, 29, 42, 47, 50, 54, 56, 59, 66, 67 and 161 for the—in one preferred embodiment combined—treatment of kidney cancer.

Thus, another aspect of the present invention relates to the use of at least one peptide according to the present invention according to any one of SEQ ID No. 8, 9, 15, 16, 20, 94, 98, 100, 103, 104, 111, 114, 117, 118, 120, 127, 129, 132, 135, 138, 139, 145, 149, 150, 151, 29, 36, 37, 41, 45, 54, 59, 70, 73, 79, 80 and 82 for the—in one preferred embodiment combined—treatment of brain cancer.

Thus, another aspect of the present invention relates to the use of at least one peptide according to the present invention according to any one of SEQ ID No. 2, 4, 18, 94, 105, 113, 114, 115, 117, 120, 124, 126, 128, 130, 131, 132, 134, 137, 138, 144, 146, 149, 153, 26, 31, 33, 36, 41, 42, 44, 49, 50, 56, 58, 63, 67, 77, 78, 85, 159, 160 and 161 for the—in one preferred embodiment combined—treatment of gastric cancer.

Thus, another aspect of the present invention relates to the use of at least one peptide according to the present invention according to any one of SEQ ID No. 2, 7, 11, 13, 94, 96, 98, 99, 100, 111, 113, 114, 115, 116, 117, 118, 120, 121, 122, 123, 124, 125, 126, 128, 129, 130, 131, 132, 137, 138, 139, 144, 145, 146, 149 and 152 for the—in one preferred embodiment combined—treatment of colorectal cancer.

Thus, another aspect of the present invention relates to the use of at least one peptide according to the present invention according to any one of SEQ ID No. 7, 8, 9, 11, 15, 16, 18, 19, 20, 21, 94, 96, 98, 99, 101, 104, 111, 113, 114, 115, 117, 118, 119, 120, 121, 126, 129, 131, 132, 135, 136, 138, 139, 143, 149, 150, 152, 26, 27, 28, 29, 37, 38, 39, 41, 44, 46, 50, 51, 52, 56, 58, 59, 60, 61, 62, 63, 66, 67, 69, 70, 71, 72, 73, 75, 76, 77, 79, 81, 82, 84 and 161 for the—in one preferred embodiment combined—treatment of liver cancer.

Thus, another aspect of the present invention relates to the use of at least one peptide according to the present invention according to any one of SEQ ID No. 1, 2, 3, 4, 13, 18, 96, 101, 103, 104, 105, 112, 113, 114, 115, 117, 119, 120, 121, 123, 124, 125, 126, 128, 131, 132, 133, 135, 136, 137, 138, 139, 143, 146 and 156 for the—in one preferred embodiment combined—treatment of pancreatic cancer.

Thus, another aspect of the present invention relates to the use of at least one peptide according to the present invention according to any one of SEQ ID No. 8, 10, 16, 18, 114, 128, 139, 143, 153, 27, 37, 41, 43, 53, 59, 61, 67, 72, 76, 78, 80, 82 and 84 for the—in one preferred embodiment combined—treatment of prostate cancer.

Thus, another aspect of the present invention relates to the use of at least one peptide according to the present invention according to any one of SEQ ID No. 9, 15, 96, 97, 120 and 127 for the—in one preferred embodiment combined—treatment of leukemia (AML, CLL).

Thus, another aspect of the present invention relates to the use of at least one peptide according to the present invention according to any one of SEQ ID No. 1, 3, 4, 5, 7, 13, 16, 18, 101, 102, 105, 112, 113, 115, 119, 124, 126, 128, 133, 145 and 156 for the—in one preferred embodiment combined—treatment of breast cancer.

Thus, another aspect of the present invention relates to the use of at least one peptide according to the present invention according to any one of SEQ ID No. 95, 98, 100, 104, 138, 149 and 151 for the—in one preferred embodiment combined—treatment of merkel cell carcinoma.

Thus, another aspect of the present invention relates to the use of at least one peptide according to the present invention according to any one of SEQ ID No. 4, 5, 9, 16, 19, 20, 94, 98, 112, 115, 117, 118, 128, 130, 132, 134, 138, 139, 144, 146 and 148 for the—in one preferred embodiment combined—treatment of melanoma.

Thus, another aspect of the present invention relates to the use of at least one peptide according to the present invention according to any one of SEQ ID No. 4, 8, 9, 10, 16, 18, 94, 98, 99, 100, 101, 102, 104, 105, 111, 113, 114, 115, 117, 118, 120, 121, 123, 124, 125, 126, 128, 129, 130, 131, 132, 134, 137, 138, 139, 142, 143, 144, 148, 149, 150 and 152 for the—in one preferred embodiment combined—treatment of ovarian cancer.

Thus, another aspect of the present invention relates to the use of at least one peptide according to the present invention according to any one of SEQ ID No. 5, 9, 13, 18, 19, 21, 95, 102, 104, 105, 113, 114, 115, 119, 120, 123, 124, 125, 127, 129, 130, 132, 133, 137, 138, 139, 141, 143, 144, 145, 146, 149, 150, 151, 153, 155, 156 and 157 for the—in one preferred embodiment combined—treatment of esophageal cancer.

Thus, another particularly preferred aspect of the present invention relates to the use of at least one peptide according to the present invention according to any one of SEQ ID No. 13, 25, 113, 114, 115, 120, 121, 128, 159, and 161 for the—preferably combined—treatment of lung cancer (including NSCLC), Thus, another aspect of the present invention relates to the use of the peptides according to the present invention for the—preferably combined—treatment of a proliferative disease selected from the group of lung cancer (including NSCLC), brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL).

The present invention furthermore relates to peptides according to the present invention that have the ability to bind to a molecule of the human major histocompatibility complex (MHC) class I or—in an elongated form, such as a length-variant—MHC class II.

The present invention further relates to the peptides according to the present invention wherein said peptides (each) consist or consist essentially of an amino acid sequence according to SEQ ID NO: 1 to SEQ ID NO: 162, preferably of SEQ ID NO: 1 to SEQ ID NO: 110.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 110, preferably containing SEQ ID No. 1 to SEQ ID No. 14 and SEQ ID No. 23 to SEQ ID No. 47 or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody. Preferably, said medicament is a cellular therapy, a vaccine or a protein derived from a soluble TCR or antibody, e.g. a sTCR comprising an anti-CD3 antibody or part thereof.

The present invention further relates to a use according to the present invention, wherein said cancer cells are lung cancer (including NSCLC), brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), esophageal cancer including cancer of the gastric-esophageal junction (OSCAR), gallbladder cancer and cholangiocarcinoma (GBC, CCC), urinary bladder cancer (UBC), uterine cancer (UEC), and preferably lung cancer cells.

The present invention further relates to biomarkers based on the peptides according to the present invention, herein called "targets", that can be used in the diagnosis of cancer, preferably lung cancer (including NSCLC). The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Collagen alpha-3(VI) chain protein (COL6A3)—COL6A3 encodes the alpha-3 chain, one of the three alpha chains of type VI collagen. The protein domains have been shown to bind extracellular matrix proteins, an interaction that explains the importance of this collagen in organizing matrix components. Remodeling of the extracellular matrix through over-expression of collagen VI contributes to cisplatin resistance in ovarian cancer cells. The presence of collagen VI correlated with tumor grade, an ovarian cancer prognostic factor (Sherman-Baust et al., 2003). COL6A3 is over-expressed in colorectal tumor (Smith et al., 2009a), salivary gland carcinoma (Leivo et al., 2005) and differentially expressed in gastric cancer (Yang et al., 2007). COL6A3 was identified as one of seven genes with tumor-specific splice variants. The validated tumor-specific splicing alterations were highly consistent, enabling clear separation of normal and cancer samples and in some cases even of different tumor stages (Thorsen et al., 2008).

Solute carrier family 6 (amino acid transporter), member 14 (SLC6A14)—SLC6A14 encodes the solute carrier family 6, member 14 (SLC6A14). SLC6A14 is an amino acid transporter and a member of the solute carrier family 6. Members of this family are sodium and chloride dependent amino acid/neurotransmitter transporters. SLC6A14 transports neutral and cationic amino acids. The transporter is expressed at low levels in normal tissues (Sloan and Mager, 1999). SLC6A14 was shown to be up-regulated in cervical (Gupta et al., 2006), colorectal (Gupta et al., 2005) and estrogen receptor (ER)-positive breast cancer (Karunakaran et al., 2011) tissues and cell lines as well as hepatoma cells (Fuchs et al., 2004). While SLC6A14 is minimally expressed in the corresponding normal tissues/cells, cancer cells up-regulate SLC6A14 to meet their increased demand for these amino acids. Alpha-methyl-DL-tryptophan (alpha-MT), a selective blocker of SLC6A14, induced amino acid deprivation and caused apoptosis in ER-positive breast cancer cell lines (Karunakaran et al., 2011).

Dual specificity phosphatase 4 (DUSP4)—The protein encoded by the DUSP4 gene is a member of the dual specificity protein phosphatase subfamily. DUSP4 inactivates ERK1, ERK2 and JNK, is expressed in a variety of tissues, and is localized in the nucleus. DUSP4 (alias MKP2) has been reported to be over-expressed in malignant as compared to non-malignant breast cancer samples (Wang et al., 2003). In colorectal cancer patient microarray datasets, DUSP4 expression was found to be differentially expressed, with the highest expression in BRAF mutated tumors. Moreover, high DUSP4 was associated with a worse overall survival (De, V et al., 2013).

Glycoprotein (transmembrane) nmb (GPNMB)—The gene GPNMB encodes a type I transmembrane glycoprotein. GPNMB has been shown to be expressed on a large panel of different cancer types and to mainly increase tumor aggressiveness by promoting tumor cell migration, invasion and metastasis formation. On the molecular level it was shown that GPNMB increases the expression of MMP-2, 3 and 9 and is itself regulated by p53 (Metz et al., 2005; Metz et al., 2007; Rose et al., 2007; Fiorentini et al., 2014). High levels of GPNMB further correlate with reduced overall survival in SCLC, GBM and ccRCC (Qin et al., 2014; Li et al., 2014; Kuan et al., 2006).

Keratin, type II cytoskeletal 80 (KRT80)—KRT80 encodes the keratin 80 (KRT80). KRT80 has been found in virtually all types of epithelia and is related to advanced tissue or cell differentiation. KRT80 containing intermediate filaments are located at the cell margins close to the desmosomal plaques, and only in cells entering terminal differentiation, KRT80 adopts a cytoplasmic distribution (Langbein et al., 2010).

Structural maintenance of chromosomes 4 (SMC4)—The SMC4 protein is a core component of the condensin complex that plays a role in chromatin condensation and has also been associated with nucleolar segregation, DNA repair, and maintenance of the chromatin scaffold (Cervantes et al., 2006).

Solute carrier family 1 (glutamate/neutral amino acid transporter), member 4 (SLC1A4)—SLC1A4 is an amino acid transporter which mediates sodium-dependent exchange of small neutral amino acids (reviewed in (Kanai et al., 2013)). SLC1A4 was described to be expressed by significantly more esophageal adenocarcinomas as compared to squamous cell carcinomas (Younes et al., 2000). Expression of SLC1A4 in prostate cancer cells was shown to be increased in response to androgen treatment (Wang et al., 2013a).

Keratin 5 (KRT5), Keratin 6A (KRT6A), Keratin 6B (KRT6B), Keratin 6C (KRT6C)—KRT5, KRT6A, KRT6B and KRT6C are homologous keratin proteins, which are intermediate filament proteins. Keratins are extensively used as marker proteins in tumor diagnostics, since their expression pattern relates to the tissue of origin of the malignancy (reviewed in (Karantza, 2011)). Under normal circumstances, KRT6A and KRT6B appear to inhibit cell migration by sequestering and thus inhibiting activity of the pro-migratory Src kinase. Whether this mechanism also works in cancer cells has not been investigated (Rotty and Coulombe, 2012). KRT5/6 staining has been proposed as one of several markers to distinguish poorly differentiated adenocarcinoma from squamous cell carcinoma in NSCLC (Zhao et al., 2014b; Xu et al., 2014). Pulmonary neuroendocrine tumors are also negative for KRT5/6 (Zhang et al., 2014).

Chemokine (C-C motif) ligand 18 (pulmonary and activation-regulated (CCL18)—This antimicrobial gene is one of several Cys-Cys (CC) cytokine genes clustered on the q arm of chromosome 17. The cytokine encoded by this gene displays chemotactic activity for naive T cells, CD4+ and CD8+ T cells and nonactivated lymphocytes, but not for monocytes or granulocytes. Up-regulation of CCL18 levels in both tumor tissue and blood has been described in cancer, and CCL18 serum levels have been proposed as biomarker for several tumor types. In multiple cases, a correlation with advanced tumor stages and poor prognosis has been shown (e.g. gastric cancer (Wu et al., 2013a), breast cancer (Chen et al., 2011; Narita et al., 2011), prostate cancer (Chen et al., 2014), bladder cancer (Urquidi et al., 2012)). Serum levels of CCL18 were increased in NSCLC patients as compared to healthy controls. In addition, increased serum levels predicted a diminished survival time in patients with adenocarcinoma (Plones et al., 2012). CCL18 is part of a 12-protein serum biomarker panel proposed for identification of NSCLC (Ostroff et al., 2010).

Matrix metallopeptidase 12 (macrophage elastase) (MMP12)—MMP12, also known as human metalloelastase (HME) or macrophage metalloelastase (MME) is a zinc endopeptidase recognized for its ability to degrade elastin.

Apart from that, it has a broad substrate range, extending to other matrix proteins such as collagens, fibronectin, laminin, proteoglycans, and non-matrix proteins such as alpha-1-antitrypsin. In asthma, emphysema and chronic obstructive pulmonary disease (COPD), MMP12 may contribute to alveolar destruction and airway remodeling (Cataldo et al., 2003; Wallace et al., 2008). MMP12 has been implicated in macrophage migration, and as it can generate angiostatin from plasminogen, it contributes to inhibition of angiogenesis (Chakraborti et al., 2003; Chandler et al., 1996; Sang, 1998). Like other metalloproteinases, MMP12 is involved in physiological processes like embryogenesis, wound healing and the menstrual cycle (Chakraborti et al., 2003; Labied et al., 2009), but also in pathological processes of tissue destruction. Although data are based on low numbers of patients in several cases, there is ample evidence in literature that MMP12 is frequently over-expressed in cancer (Denys et al., 2004; Hagemann et al., 2001; Ma et al., 2009; Vazquez-Ortiz et al., 2005; Ye et al., 2008). However, data are controversial with respect to the impact of MMP12 over-expression on clinical parameters and prognosis. While it may be involved in matrix dissolution and, thus, metastasis, it can also inhibit tumor growth through production of angiostatin, which negatively impacts angiogenesis (Gorrin-Rivas et al., 2000; Gorrin Rivas et al., 1998; Kim et al., 2004). For lung cancer, consequences of MMP12 expression are controversial. MMP12 over-expression in epithelial cells has been reported in inflammation-triggered lung remodeling. MMP12 up-regulation may play a role in emphysema-to-lung cancer transition (Qu et al., 2009). Animal studies suggest that MMP12 expression by stroma or macrophages suppresses growth of lung tumors (Acuff et al., 2006; Houghton et al., 2006). However, there are also reports that MMP12 over-expression in lung tumors correlates with recurrence, metastatic disease and shorter relapse-free survival after resection (Cho et al., 2004; Hofmann et al., 2005).

Lysosomal-associated membrane protein 3 (LAMP3)—LAMP3 is a type I transmembrane protein found in the lysosomal compartment, with a small cytoplasmic domain and a heavily glycosylated luminal domain (Wilke et al., 2012). Up-regulation of LAMP3 has been reported in several cancers, however, expression of LAMP3 by tumor cells themselves has not been demonstrated. LAMP3(+) DCs have been detected specifically at the invasive tumor margin forming clusters with proliferating T-lymphocytes and have thus been proposed to reflect a local anti-tumor immune response, for example in renal cell carcinoma (Middel et al., 2010), esophageal squamous cell carcinoma (Liu et al., 2010), colorectal carcinoma (Yuan et al., 2008; Sandel et al., 2005), as well as in melanoma (Ladanyi et al., 2007). A meta-analysis of transcriptomics data suggested that low levels of LAMP3 expression in lung cancer might be associated with shorter overall survival (Lindskog et al., 2014).

Centromere protein N (CENPN)—The protein encoded by the CENPN gene forms part of the nucleosome-associated complex and is important for kinetochore assembly. CENPN recognizes a centromere-specific histone variant (CENP-A), and is thus required to define the recruitment site for many other centromeric proteins (Carroll et al., 2009). Depletion of CENPN and other proteins of the nucleosome-associated complex (NAC) does not impair bipolar spindle formation but leads to defects in chromosome congression (McClelland et al., 2007). CENPN, together with other NAC proteins, is recruited to DNA double-strand breaks, and thus the complex has been proposed to play a role in DNA repair (Zeitlin et al., 2009).

Procollagen-lysine, 2-oxoglutarate 5-dioxygenase 2 (PLOD2)—The protein encoded by this gene is a membrane-bound homodimeric enzyme that is localized to the cisternae of the rough endoplasmic reticulum. Mutations in the coding region of this gene are associated with Bruck syndrome. PLOD2 up-regulation has been described in colorectal cancer (Nicastri et al., 2014), multiple myeloma (Slany et al., 2014) and cervical cancer (Rajkumar et al., 2011), and has been associated with bone metastasis formation (Blanco et al., 2012). A correlation of elevated PLOD2 expression with poor prognosis has been shown for glioblastoma (Dong et al., 2005) as well as for breast cancer (Gilkes et al., 2013) and hepatocellular carcinoma, where it was also associated with increased tumor size and formation of intrahepatic metastasis (Noda et al., 2012).

Matrix metallopeptidase 1 (MMP1)—MMP1 is part of the matrix metalloproteinase (MMP) family. In general, MMPs play an essential role in regulation of vascular function, remodeling and angiogenesis. Through degradation of ECM and other extracellular molecules, they facilitate migration and invasion of endothelial cells and vascular smooth muscle cells, and influence vascular cell proliferation and apoptosis (Chen et al., 2013). MMP1 over-expression has been described for several cancer types and has been associated with angiogenesis, invasion, and poor survival. For example, elevated MMP1 levels have been described as an independent factor for survival in colon cancer (Langenskiold et al., 2013), and MMP1 expression in tumor and stroma is associated with tumor progression and poor prognosis in breast cancer (Bostrom et al., 2011). MMP1 levels have been shown to be elevated in both plasma and tumor tissue of lung cancer patients and associated with advanced stage and decreased survival (Li et al., 2010b). A meta-analysis has confirmed an association of MMP1-1607 1G/2G polymorphism with increased risk of developing lung cancer (Xiao et al., 2012).

Keratin 10 (KRT10), Keratin 12 (KRT12), Keratin 13 (KRT13), Keratin 14 (KRT14), Keratin 15 (KRT15), Keratin 16 (KRT16), Keratin 17 (KRT17), Keratin 19 (KRT19)—The homologous keratin proteins KRT10, KRT12, KRT13, KRT14, KRT15, KRT16, KRT17 and KRT19 are intermediate filament proteins. Some of the keratins have been associated with stem cell properties, such as KRT14 which is considered a cancer stem cell marker (Hatina and Schulz, 2012; Schalken and van, 2003). KRT15 is used as a marker for identification and targeting of epidermal stem cells (Adhikary et al., 2013; Troy et al., 2011), and KRT17 is expressed in stem cells in the basal layer of the hair bulge (Bragulla and Homberger, 2009). Expression patterns of the different keratins have been analyzed in various cancer types, and both up- and down-regulation have been reported. For example, high levels of KRT17 have been associated with poor prognosis (Wang et al., 2013b; Escobar-Hoyos et al., 2014) and advanced stage (Kim et al., 2012). For KRT13, the majority of studies suggest down-regulation in cancerous tissue (Hourihan et al., 2003; Ida-Yonemochi et al., 2012), and expression of KRT13 appears to be replaced with that of KRT17 during squamous cell transformation (Mikami et al., 2011). For KRT10 and KRT15, both up- and down-regulation in cancer have been demonstrated by different studies. KRT19 is consistently reported to be over-expressed in many cancer types, and has been associated with metastasis and poor survival (Zong et al., 2012; Lee et al., 2012). KRT12 is expressed in corneal epithelia. The corneas display down-regulation of keratin 12 which is considered a differentiation marker (Zhang et al., 2010b).

Mucin 16, cell surface associated (MUC16)—MUC16 is the largest of several membrane-bound mucins. MUC16 is a single-pass transmembrane protein with a heavily glycosylated extracellular domain. MUC16 is a tumor-associated antigen that is cleaved from the surface of ovarian cancer cells and shed into blood and used as a well-established biomarker for monitoring the growth of ovarian cancer (Bafna et al., 2010). Increased MUC16 expression levels have been demonstrated in lung squamous cell carcinoma (Wang et al., 2014). In addition, high MUC16 serum levels have been correlated with shortened survival of NSCLC patients (Yu et al., 2013; Cedres et al., 2011). Combined with other biomarkers, MUC16 may be part of a gene expression signature for subtypes of lung cancer (Li et al., 2012).

Integrin, alpha 2 (CD49B, alpha 2 subunit of VLA-2 receptor) (ITGA2)—ITGA2 encodes the alpha subunit of a transmembrane receptor for collagens and related proteins. A limited number of studies have reported dysregulation of ITGA2 in cancer, with evidence for both elevated as well as decreased levels: In pancreatic ductal adenocarcinoma, ITGA2 was hypomethylated and over-expressed, and elevated expression was associated with poor survival (Nones et al., 2014). In contrast, down-regulation of ITGA2 has been shown for prostate carcinoma (Shaikhibrahim et al., 2011). Decreased expression of ITGA2 was associated with metastasis formation and poor survival in breast and prostate cancer (Ramirez et al., 2011).

Olfactomedin-like 2B (OLFML2B)—OLFML2B belongs to the family of olfactomedin proteins, which are extracellular glycoproteins, mainly involved in the differentiation of chemosensory cilia, early neurogenesis, dorsalization of neural tubes, neuromuscular signaling, exocytosis of synaptic vesicles ant the pathogenesis of glaucoma. OLFM2B transcripts can be detected in a variety of different tissues in the mouse, including lung, stomach and prostate, but are absent in liver (Furutani et al., 2005). The OLFML2B gene maps to chromosome 1q23.3, which was demonstrated to be a susceptibility locus for schizophrenia in linkage studies (Puri et al., 2007).

Tetratricopeptide repeat domain 13 (TTC13)—TTC13 belongs to the family of tetratricopeptide repeat (TPR) domain containing proteins. TPR domains appear to be important for chaperone function, cell cycle, transcription an protein transport and TPR motif containing proteins are often associated with multiprotein complexes (Blatch and Lassie, 1999). The TCC13 gene maps to chromosome 1q42.2. Chromosome 1q42.2-43 was described as locus of a putative predisposing gene for prostate cancer in one linkage analysis study (Berthon et al., 1998), but this could not be confirmed for larger patient populations in further studies (Singh, 2000; Gibbs et al., 1999).

Dedicator of cytokinesis 2 (DOCK2)—The protein encoded by the DOCK2 gene belongs to the CDM protein family. DOCK2 is known as important factor for lymphocyte migration and chemotaxis. Exome and whole genome sequencing studies identified mutations within the DOCK2 gene in colorectal cancer, esophageal adenocarcinoma and intraductal papillary mucinous neoplasms of the pancreas (Yu et al., 2014; Dulak et al., 2013; Furukawa et al., 2011). Furthermore, DOCK2 was shown to be differentially expressed in pediatric astrocytoma samples and might therefore represent an interesting therapeutic target for this disease (Zhao et al., 2014a).

Poliovirus receptor-related 1 (herpesvirus entry mediator C) (PVRL1)—PVRL1 encodes an adhesion protein that plays a role in the organization of adherent junctions and tight junctions in epithelial and endothelial cells. The PVRL1 gene maps to chromosome 11q23, a region that has been found to be amplified in adenoid cystic carcinoma (Zhang et al., 2013). With an important function in cell adhesion, PVRL1 has been associated with regulation of cell invasive and migratory properties as well as with epithelial-mesenchymal transition, both crucial processes in tumor development. PVRL1 was identified as part of a signature profile of the squamous cell carcinoma subtype of cervical cancer (Imadome et al., 2010). PVRL1 expression was found to be increased in thyroid tumors compared to normal thyroid tissue and further increased in papillary thyroid cancer (Jensen et al., 2010). PVRL1/2 expression is associated with a more favorable prognosis in acute myeloid leukemia (Graf et al., 2005).

FK506 binding protein 10, 65 kDa (FKBP10)—FK506-binding protein 10 (FKBP10) belongs to the FKBP-type peptidyl-prolyl cis/trans isomerase family. It is located in endoplasmic reticulum and acts as molecular chaperones (Ishikawa et al., 2008; Patterson et al., 2000). It is highly expressed in lung development and can be reactivated in a coordinated manner with extracellular matrix proteins after lung injury (Patterson et al., 2005).

ATP-binding cassette, sub-family C (CFTR/MRP), member 1 (ABCC1)—The protein encoded by the ABCC1 gene is a member of the superfamily of ATP-binding cassette (ABC) transporters. ABC proteins transport various molecules across extra- and intracellular membranes. ABCC1 plays an important role as drug efflux pump, in both normal and tumor cells (Chen and Tiwari, 2011). Several studies have described over-expression of ABCC1 in different tumor types, and in many cases, an association of ABCC1 expression levels with tumor stage, metastasis, and poor prognosis has been found (e. g. in breast, prostate, and lung cancer) (Deeley et al., 2006). A study in Chinese patients identified a SNP in the ABCC1 gene to increase the susceptibility for NSCLC (Yin et al., 2011). Another study has reported an association between ABCC1 SNPs and progression-free survival of NSCLC patients (Lamba et al., 2014).

Arachidonate 15-lipoxygenase, type B (ALOX15B)—ALOX15B encodes a member of the lipoxygenase family of structurally related nonheme iron dioxygenases involved in the production of fatty acid hydroperoxides. The role that ALOX15B, more well-known as 15-LOX-2, and its enzymatic product, 15-S-hydroxyeicosatetraenoic acid (15S-HETE), play in tumor development, has been most intensively studied in prostate cancer. Several studies have demonstrated that ALOX15B expression levels, as well as levels of 15S-HETE production, are significantly decreased in prostate cancer as compared to normal tissue or cell lines (Hu et al., 2013; Shappell et al., 2001). In normal lung, ALOX15B expression is restricted to type II pneumocytes. Expression is elevated in NSCLC, and an inverse correlation has been described between ALOX15B levels and tumor grade as well as tumor cell proliferation index (Gonzalez et al., 2004).

Sphingomyelin phosphodiesterase, acid-like 3B (SMPDL3B)—SMPDL3B is a sphingomyelin phosphodiesterase expressed in podocytes, whose expression has been associated with diabetic kidney disease and focal segmental glomerulosclerosis. Decreased expression of SMPDL3B in kidney disease has been associated with actin cytoskeleton remodeling and apoptosis (Merscher and Fornoni, 2014). The SMPDL3B gene maps to chromosome 1p35.3.

Glutamine-fructose-6-phosphate transaminase 2 (GFPT2)—GFPT2 is involved in neurite outgrowth, early neuronal cell development, neuropeptide signaling/synthesis and neuronal receptor (Tondreau et al., 2008). Genetic variants in GFPT2 are associated with type 2 diabetes and diabetic nephropathy (Zhang et al., 2004). Furthermore, association of SNPs in GFPT2 suggests that the gene involved in modulation of oxidative pathway could be major contributor to diabetic chronic renal insufficiency (Prasad et al., 2010). DNA methylation of the GFPT2 gene was validated in primary acute lymphoblastic leukemia (ALL) samples. Patients with methylation of multiple CpG islands had a worse overall survival (Kuang et al., 2008). GFPT2 plays a role in glutamine metabolism and was observed to be more highly expressed in mesenchymal cell lines. Glutamine metabolism may play an important role in tumor progression and inhibitors of cellular metabolic pathways may be a form of epigenetic therapy (Simpson et al., 2012).

DEAD (Asp-Glu-Ala-Asp) box helicase 5 (DDX5)—DDX5 (p68) is an ATP-dependent RNA helicase which plays a role in splicing, rRNA processing and ribosome biogenesis, miRNA processing, as well as in transcriptional regulation. DDX5 is a transcriptional coactivator of several factors which play a role in cancer development, such as androgen receptor, p53, and Runx2. Over-expression of DDX5 has been demonstrated for a number of different cancer types, as for example colorectal cancer, breast cancer, prostate cancer, glioma, hepatocellular carcinoma, and leukemia (Dai et al., 2014; Fuller-Pace, 2013).

Enolase 1, (alpha) (ENO1)—The ENO1 gene encodes enolase-alpha (ENOA), one of three enolase proteins, the others being enolase-beta and -gamma, respectively. ENO1/ENOA over-expression has been demonstrated in many cancer types (Capello et al., 2011). ENOA is a metalloenzyme that functions in glycolysis in the synthesis of phosphoenolpyruvate. Elevated ENOA levels have been correlated with poor survival in NSCLC patients (Chang et al., 2006). Similarly, another study demonstrated up-regulation of ENO1 expression in a poor prognosis group of lung adenocarcinoma patients (Pernemalm et al., 2013). ENOA has been demonstrated as a tumor-associated antigen, and anti-ENOA antibodies as well as ENOA-specific T cells have been detected in pancreatic adenocarcinoma patients (Cappello et al., 2009). Autoantibodies to ENOA have also been detected in NSCLC patients, and ENOA expression has been shown to be increased in NSCLC tissue (He et al., 2007; Li et al., 2006).

Killer cell lectin-like receptor subfamily D, member 1 (KLRD1)—KLRD1, more well-known as CD94, associates with NKG2 molecules to form a heterodimer that is expressed on natural killer (NK) cells and cytotoxic T lymphocytes (CTLs). The inhibitory receptor KLRD1 (CD94):NKG2A was shown to be over-expressed in tumor-infiltrating lymphocytes for example in renal cell carcinoma and cervical cancer, which might contribute to an impaired anti-tumor immune response (Schleypen et al., 2003; Sheu et al., 2005). Similarly, over-expression of HLA-E, the KLRD1 (CD94):NKG2A ligand, on tumor cells might additionally contribute to tumor immune escape (Bossard et al., 2012; Gooden et al., 2011).

Collagen, type XII, alpha 1 (COL12A1)—The COL12A1 gene encodes the alpha chain of type XII collagen, a member of the FACIT (fibril-associated collagens with interrupted triple helices) collagen family. Type XII collagen is a homotrimer found in association with type I collagen, an association that is thought to modify the interactions between collagen I fibrils and the surrounding matrix (Oh et al., 1992). COL12A1 may be involved in basement membrane regulation providing specific molecular bridges between fibrils and other matrix components (Thierry et al., 2004). COL12A1 is expressed in heart, placenta, lung, skeletal muscle and pancreas (Dharmavaram et al., 1998), in a variety of connective tissues including articular and epiphyseal cartilage (Gregory et al., 2001; Walchli et al., 1994; Watt et al., 1992). COL12A1 was down-regulated in tumors with high microsatellite instability when compared to the stable group with low or null microsatellite instability (Ortega et al., 2010).

ATP-binding cassette, sub-family A (ABC1), member 13 (ABCA13)—In human, the ATP-binding cassette (ABC) family of transmembrane transporters has at least 48 genes and 7 gene subfamilies. The predicted ABCA13 protein consists of 5,058 amino acid residues making it the largest ABC protein described to date (Prades et al., 2002). Knight et al. determined that ABCA13 protein is expressed in mouse and human hippocampus and cortex, both regions relevant to schizophrenia and bipolar disorder (Knight et al., 2009). The ABCA13 gene maps to chromosome 7p12.3, a region that contains an inherited disorder affecting the pancreas (Shwachman-Diamond syndrome) as well as a locus involved in T-cell tumor invasion and metastasis (INM7), and therefore is a positional candidate for these pathologies (Prades et al., 2002).

Cyclin B2 (CCNB2)—CCNB2 is one of several cyclins that associate with the major cell cycle-regulatory kinase CDK1 (CDC2). Cyclin levels are transcriptionally regulated over the cell cycle, providing different levels of activity and specificity to CDK1, thus controlling cell cycle progression. Expression of cyclin B2 is regulated by the tumor suppressor genes p53 and BRCA1 which act by repressing cyclin B2 transcription (Quaas et al., 2012; De et al., 2011). CCNB2 up-regulation has been described in several tumor types, such as cervical cancer (Espinosa et al., 2013; Rajkumar et al., 2011), bladder cancer (Lu et al., 2010), colorectal carcinoma (Park et al., 2007), astrocytoma (Liu et al., 2013), and glioblastoma (Hodgson et al., 2009). CCNB2 expression levels were associated with poor prognosis in breast cancer and identified as an independent prognostic maker for survival (Shubbar et al., 2013). CCNB2 is over-expressed in NSCLC (Hofmann et al., 2004), and was identified an independent predictor of poor prognosis in patients with lung adenocarcinoma, but not squamous cell carcinoma (Takashima et al., 2014).

MutS homolog 6 (MSH6)—MSH6 encodes a member of the DNA mismatch repair MutS family. MSH proteins, including MSH6, recognize errors in the genome sequence during replication, preventing the duplication of the damaged strand and repairing single strand breaks (Conde-Perezprina et al., 2012). In several kinds of cancer, mutations in MSH6 and an erroneous DNA mismatch repair machinery (MMR) were described (e.g. colorectal cancers (Sameer et al., 2014; Vilar and Gruber, 2010; Silva et al., 2009; Kastrinos and Syngal, 2007; Davidson, 2007), pancreatic cancer (Solomon et al., 2012), ovarian cancer (Xiao et al., 2014), breast cancer (Mandi et al., 2013)).

PRP3 pre-mRNA processing factor 3 homolog (S. cerevisiae) (PRPF3)—PRPF3 encodes the pre-mRNA processing factor 3. PRPF3 mediates recruitment of the nuclear RNA decay machinery to the spliceosome (Nag and Steitz, 2012). PRPF3 is up-regulated in hepatocellular carcinoma through a fetal/cancer-specific splice variant of the transcription factor HNF4alpha (Niehof and Borlak, 2008).

Lysophosphatidylcholine acyltransferase 1 (LPCAT1)—LPCAT1 catalyzes the conversion of lysophosphatidylcholine (LPC) to phosphatidylcholine. In addition, LPCAT1 is able to convert lyso-PAF (alkylated LPC) into platelet-activating factor (PAF). LPCAT1 over-expression has been described in colorectal cancer (Mansilla et al., 2009), hepatocellular carcinoma (Morita et al., 2013), breast cancer (Abdelzaher and Mostafa, 2015), prostate cancer (Xu et al., 2013; Grupp et al., 2013; Zhou et al., 2012), and lung cancer (Wu et al., 2013b). LPCAT1 over-expression promoted cell proliferation, migration, and invasion in vitro (Morita et al., 2013).

Downstream neighbor of SON (DONSON)—DONSON encodes the downstream neighbor of SON (DONSON). DONSON is a centrosomal protein whose levels are regulated over the cell cycle, peaking during S-phase. DONSON is required for formation of a proper mitotic spindle, and appears to play a role in the DNA damage response (Fuchs et al., 2010). No cancer related literature is available.

Budding uninhibited by benzimidazoles 1 homolog beta (yeast) (BUB1B)—BUB1B encodes BUB1 mitotic checkpoint serine/threonine kinase B, a serine/threonine-protein kinase. It functions as a mitotic regulator that ensures accurate segregation of chromosomes through its role in the mitotic checkpoint and the establishment of proper microtubule-kinetochore attachments. Both up- and down-regulation of BUB1B expression has been reported in various tumors. In general, more literature reports on over-expression of BUB1B in cancer, and an association with tumor progression and poor prognosis has also been described, as for example in nasopharyngeal carcinoma (Huang et al., 2012a), tonsillar carcinoma (Hannisdal et al., 2010), breast cancer (Maciejczyk et al., 2013), epithelial ovarian cancer (Lee et al., 2009), and pancreatobiliary-type adenocarcinoma (Gladhaug et al., 2010). Similarly, reduced BUB1B protein was associated with longer survival in prostate cancer (Cirak et al., 2013).

Component of oligomeric Golgi complex 4 (COG4)—COG4 a component of an oligomeric protein complex involved in the structure and function of the Golgi apparatus. Interaction studies suggest that COG4 serves as a core component of the complex and holds a crucial role in the assembly/function of the complex (Loh and Hong, 2004). The COG subunits COG4, 6, and 8, are capable of interacting with defined Golgi SNAREs and are involved in defining the specificity of vesicular sorting within the Golgi (Willett et al., 2013). Furthermore, the COG complex has been shown to regulate the maintenance of Golgi glycosylation machinery (Pokrovskaya et al., 2011).

Proteasome (prosome, macropain) 26S subunit, non-ATPase, 14 (PSMD14)—PSMD14 is a component of the 26S proteasome, a multiprotein complex that degrades proteins targeted for destruction by the ubiquitin pathway. The PSMD14 protein within the 19S complex (19S cap; PA700) is responsible for substrate deubiquitination during proteasomal degradation (Spataro et al., 1997). Aberrant expression and dysfunction of proteasome subunits have been involved in malignant transformation and in cell resistance to various cytotoxic drugs. Over-expression of PSMD14 in mammalian cells affects cell proliferation and the response to cytotoxic drugs like vinblastine, cisplatin and doxorubicin (Spataro et al., 2002). Down-regulation of PSMD14 by siRNA transfection had a considerable impact on cell viability causing cell arrest in the G0-G1 phase, ultimately leading to senescence (Byrne et al., 2010).

RAD54 homolog B (S. cerevisiae) (RAD54B)—DNA repair and recombination protein RAD54B is a protein that in humans is encoded by the RAD54B gene. RAD54 binds to double-stranded DNA, and displays ATPase activity in the presence of DNA. The human RAD54B protein is a paralog of the RAD54 protein, which plays important roles in homologous recombination. Homologous recombination (HR) is essential for the accurate repair of DNA double-strand breaks (DSBs) (Sarai et al., 2008). Knockdown of RAD54B, a gene known to be somatically mutated in cancer, causes chromosome instability (CIN) in mammalian cells (McManus et al., 2009). RAD54B elevated gene expression is significantly associated with shorter time-to-progression and poor OS in GBM patients (Grunda et al., 2010).

Frizzled family receptor 1 (FZD1), frizzled family receptor 2 (FZD2), frizzled family receptor 7 (FZD7)—The genes FZD2, FZD1 and FZD7 are all from the 'frizzled' gene family; members of this gene family encode 7-transmembrane domain proteins that are receptors for Wnt signaling proteins. The expression of the FZD2 gene appears to be developmentally regulated, with high levels of expression in fetal kidney and lung and in adult colon and ovary (Sagara et al., 1998; Zhao et al., 1995). The FZD1 protein contains a signal peptide, a cysteine-rich domain in the N-terminal extracellular region, 7 transmembrane domains, and a C-terminal PDZ domain-binding motif. The FZD1 transcript is expressed in various tissues, including lung as well as heart, kidney, pancreas, prostate, and ovary (Sagara et al., 1998). The expression of frizzled 1 and 2 receptors was found to be up-regulated in breast cancer (Milovanovic et al., 2004). The FZD7 protein contains an N-terminal signal sequence, 10 cysteine residues typical of the cysteine-rich extracellular domain of Fz family members, 7 putative transmembrane domains, and an intracellular C-terminal tail with a PDZ domain-binding motif. FZD7 gene expressions may down-regulate APC function and enhance beta-catenin-mediated signals in poorly differentiated human esophageal carcinomas (Sagara et al., 1998; Tanaka et al., 1998).

Wingless-type MMTV integration site family, member 5A (WNT5A)—In general, Wnt5a regulates a variety of cellular functions, such as proliferation, differentiation, migration, adhesion and polarity (Kikuchi et al., 2012). It is expressed in undifferentiated human embryonic stem cells (Katoh, 2008). WNT5A is classified as a non-transforming WNT family member whose role in carcinogenesis is still ambiguous. It exhibits tumor suppressor activities in some cancers (thyroid, brain, breast and colorectum), but is aberrantly up-regulated in cancers of lung, stomach and prostate (Li et al., 2010a). Oncogenic WNT5A activates canonical WNT signaling in cancer stem cells for self-renewal, and non-canonical WNT signaling at the tumor-stromal interface for invasion and metastasis (Katoh and Katoh, 2007). Expression of WNT5A has been described for a variety of tumor entities. For example, abnormal protein expression of Wnt5a was observed in 28% of prostate cancer where it promotes aggressiveness (Yamamoto et al., 2010). Furthermore, WNT5A over-expression is described to be associated with poor prognosis and/or increasing tumor grade in ovarian cancer (Badiglian et al., 2009), melanoma (Da Forno et al., 2008; Weeraratna et al., 2002), GBM (Yu et al., 2007), lung cancer (Huang et al., 2005) and pancreatic cancer (Ripka et al., 2007). In HCC, it seems that the canonical Wnt signaling pathway contributes to tumor initiation and the noncanonical signaling to tumor progression (Yuzugullu et al., 2009).

Fibroblast activation protein, alpha (FAP)—Fibroblast activation protein (FAP) is a type II integral membrane glycoprotein belonging to the serine protease family. The putative serine protease activity of FAP alpha and its in vivo induction pattern may indicate a role for this molecule in the control of fibroblast growth or epithelial-mesenchymal interactions during development, tissue repair, and epithelial carcinogenesis (Scanlan et al., 1994). Most normal adult tissues and benign epithelial tumors show little or no detectable FAP expression. However, FAP expression is detected in the stroma of over 90% of malignant breast, colorectal, lung, skin and pancreatic tumors, fibroblasts of healing wounds, soft tissue sarcomas, and some fetal mesenchymal cells. FAP has a potential role in cancer growth and metastasis through cell adhesion and migration processes, as well as rapid degradation of ECM components. Thus, it is present on tumor cells invading the ECM and an endothelial cell involved in angiogenesis, but is not expressed in inactive cells of the same type (Dolznig et al., 2005; Kennedy et al., 2009; Rettig et al., 1993; Rettig et al., 1994; Scanlan et al., 1994; Zhang et al., 2010a).

Cyclin B1 (CCNB1)—CCNB1 encodes cyclin B1, one of several mitotic cyclins that associates with CDK1/CDC2 to promote mitotic progression. CNB1 over-expression has been described in numerous cancer types and was associated with tumor progression and poor prognosis, as for example in colorectal carcinoma (Li et al., 2003), breast cancer (Aaltonen et al., 2009; Agarwal et al., 2009), NSCLC (Cooper et al., 2009), and esophageal squamous cell carcinoma (Huang et al., 2014). Also in gastric cancer, CCNB1 expression was associated with regional lymph node metastasis and poor clinical prognosis (Begnami et al., 2010; Fujita et al., 2012). Antibodies directed against CCNB1 have been detected in patients with lung or prostate cancer and have been proposed as a biomarker for early detection of lung cancer (Egloff et al., 2005; Zhang et al., 2003).

ATPase, Ca++ transporting, cardiac muscle, fast twitch 1 (ATP2A1), ATPase, Ca++ transporting, cardiac muscle, fast twitch 2 (ATP2A2)—Both genes (ATP2A1 and ATP2A2) encode SERCA Ca(2+)-ATPases. Sarcoplasmic reticulum (SR)1/ER calcium ATPases (SERCAs) are calcium pumps that couple ATP hydrolysis with calcium transport across the SR/ER membrane (MacLennan et al., 1997). SERCAs are encoded by three homologous genes: SERCA1 (ATP2A1), SERCA2 (ATP2A2), and SERCA3 (Wu et al., 1995). Some evidence has emerged to show that SERCA may also have a direct impact on the processes of apoptosis, differentiation, and cell proliferation (Chami et al., 2000; Ma et al., 1999; Sakuntabhai et al., 1999). Mutations in ATP2A1, encoding SERCA1, cause some autosomal recessive forms of Brody disease, characterized by increasing impairment of muscular relaxation during exercise (Odermatt et al., 1996). ATP2A2 is an ATPase associated with Darier's disease, a rare, autosomal dominant hereditary skin disorder characterized by abnormal keratinization and acantholysis (Huo et al., 2010). Germline alterations of ATP2A2 may predispose to lung and colon cancer and an impaired ATP2A2 gene might be involved in carcinogenesis (Korosec et al., 2006). In a Small Cell Lung Cancer (H1339) and an Adeno Carcinoma Lung Cancer (HCC) cell line the ER Ca2+-content was reduced compared to normal human bronchial epithelial. The reduced Ca2+-content correlated with a reduced expression of SERCA 2 pumping calcium into the ER (Bergner et al., 2009). ATP2A2 could be potential prognostic markers for colorectal cancer CRC patients. It was detected in circulating tumor cells (CTCs), and the postoperative relapse was significantly correlated with gene over-expression (Huang et al., 2012b).

Fibronectin 1 (FN1)—FN1 encodes fibronectin, a glycoprotein present in a soluble dimeric form in plasma, and in a dimeric or multimeric form at the cell surface and in extracellular matrix. It has been reported that in most tumors, FN1 is predominantly expressed by cancer-associated fibroblasts (CAFs) and endothelial cells, but not tumor cells (Berndt et al., 2010). Elevated levels of FN1 have been reported for some cancer types and associated with poor prognosis or cancer progression, as for example in gallbladder cancer (Cao et al., 2015), prostate cancer (von et al., 2013), and renal cell carcinoma (Steffens et al., 2012; Waalkes et al., 2010). FN1 has also been implicated in the stimulation of lung cancer pathogenesis, including cell growth, chemoresistance and inhibition of apoptosis (reviewed in (Ritzenthaler et al., 2008)).

Insulin-like growth factor 2 mRNA binding protein 3 (IGF2BP3)—IGF2BP3 is a member of the insulin-like growth factor-II mRNA-binding protein family, implicated in mRNA localization, turnover and translational control. The protein contains several KH (K-homologous) domains, which are important in RNA binding and are known to be involved in RNA synthesis and metabolism. Expression occurs mainly during embryonic development and has been described for some tumors. Thus, IGF2BP3 is considered to be an oncofetal protein (Liao et al., 2005). IGF2BP3 may promote tumor cell proliferation by enhancing IGF-II protein synthesis and by inducing cell adhesion and invasion through stabilization of CD44 mRNA (Findeis-Hosey and Xu, 2012). Moreover, IGF2BP3 expression has been studied in many human neoplasms with growing evidence that it mediates migration, invasion, cell survival and tumor metastasis (Jeng et al., 2009; Kabbarah et al., 2010; Li et al., 2011; Liao et al., 2011; Lu et al., 2011; Hwang et al., 2012; Samanta et al., 2012) and it might also be implicated in angiogenesis (Suvasini et al., 2011; Chen et al., 2012). In lung adenocarcinomas, a higher frequency of IGF2BP3 expression can be detected in moderately or poorly differentiated adenocarcinomas, which may be associated with an aggressive biological behavior (Findeis-Hosey et al., 2010; Beljan et al., 2012; Findeis-Hosey and Xu, 2012).

Laminin, Gamma 2 (LAMC2)—

Laminins, a family of extracellular matrix glycoproteins, are the major noncollagenous constituent of basement membranes. They have been implicated in a wide variety of biological processes including cell adhesion, differentiation, migration, signaling, neurite outgrowth and metastasis. The LAMC2 gene encodes the laminin-5 gamma2 chain, which is part of laminin-5, one of the major components of the basement membrane zone. LAMC2 was frequently up-regulation by promoter demethylation in gastric cancer (Kwon et al., 2011). LAMC2 was found to be over-expressed in angiotropic melanoma areas vs. avascular melanoma areas (Lugassy et al., 2009). LAMC2 is a biomarker of bladder cancer metastasis, and its expression level was associated with tumor grade (Smith et al., 2009b). LAMB3 and LAMC2 genes were co-expressed in 21 of 32 non-SCLC cell lines (66%) but only in one of 13 SCLC cell lines (8%). Co-expression of the LAMB3 and LAMC2 genes was also observed in all 4 cases of primary non-SCLC cells examined but not in the corresponding non-cancerous lung cells (Manda et al., 2000).

Cerebral endothelial cell adhesion molecule (CERCAM)—CERCAM is localized at the surface of endothelial cells (Starzyk et al., 2000) and mapped on chromosome 9q34.11, a candidate region on 9q, identified as linked to familial idiopathic scoliosis (Miller et al., 2012). The CEE-CAM1 gene is widely transcribed in the nervous system and in several secretory tissues such as salivary glands, pancreas, liver and placenta (Schegg et al., 2009). The CERCAM protein is structurally similar to the ColGalT enzymes GLT25D1 and GLT25D2. But although its function is still not known, it seems to be is functionally different from the related GLT25D1 protein, and the protein does not function as a glycosyltransferase like GLT25D1 and GLT25D2 proteins (Perrin-Tricaud et al., 2011).

Matrix-remodeling associated 5 (MXRA5)—MXRA5, also known as adlican, encodes an adhesion proteoglycan and belongs to a group of genes involved in ECM remodeling and cell-cell adhesion (Rodningen et al., 2008). Although the function of MXRA5 in cancer is unknown, somatic mutations in MXRA5 have been identified in tumors obtained from a variety of tissues such as skin, brain, lung, and ovary. RT-PCR was performed on adlican (MXRA5) confirmed microarray findings of over-expression in colon cancers compared to normal colon tissue (13 colorectal tumors and 13 normal tissues) (Zou et al., 2002). In a recent study, matrix-remodeling associated 5 was the second most frequently mutated gene in NSCLC (first is TP53) (Xiong et al., 2012).

ADAM metallopeptidase domain 8 (ADAM8)—ADAM8 is a member of the ADAM (a disintegrin and metalloprotease domain) family. Many ADAM species, including ADAM8, are expressed in human malignant tumors, where they are involved in the regulation of growth factor activities and integrin functions, leading to promotion of cell growth and invasion (Mochizuki and Okada, 2007). The expression of ADAM8 was positively correlated to EGFR. Both were mainly expressed in the cytoplasm and on the cell membrane (Wu et al., 2008). ADAM8 was abundantly expressed in the great majority of lung cancers examined. Exogenous expression of ADAM8 increased the migratory activity of mammalian cells, an indication that ADAM8 may play a significant role in progression of lung cancer (Ishikawa et al., 2004). ADAM8 has been associated with poor prognosis of lung cancer (Hernandez et al., 2010). ADAM8 over-expression was associated with shorter patient survival and it was a good predictor of distant metastases in RCC (Roemer et al., 2004b; Roemer et al., 2004a). In addition, expression levels and the protease activities of ADAM8 correlated with invasive activity of glioma cells, indicating that ADAM8 may play a significant role in tumor invasion in brain cancer (Wildeboer et al., 2006).

Melanoma antigen family F, 1 (MAGEF1)—Most known members of the MAGE (melanoma-associated antigen) superfamily are expressed in tumors, testis and fetal tissues, which has been described as a cancer/testis expression, pattern (MAGE subgroup I). Peptides of MAGE subgroup I have been successfully used in peptide and DC vaccination (Nestle et al., 1998; Marchand et al., 1999; Marchand et al., 1999; Marchand et al., 1995; Thurner et al., 1999). In contrast, some MAGE genes (MAGE subgroup II), such as MAGEF1, are expressed ubiquitously in all adult and fetal tissues tested and also in many tumor types including ovarian, breast, cervical, melanoma and leukemia (Nestle et al., 1998; Marchand et al., 1999; Marchand et al., 1999; Marchand et al., 1995; Thurner et al., 1999). Nevertheless, over-expression of MAGEF1 could be detected in NSCLC (Tsai et al., 2007) and in 79% of a cohort of Taiwanese colorectal cancer patients (Chung et al., 2010).

Small nuclear ribonucleoprotein 200 kDa (U5) (SNRNP200)—Pre-mRNA splicing is catalyzed by the spliceosome, a complex of specialized RNA and protein subunits that removes introns from a transcribed pre-mRNA segment. The spliceosome consists of small nuclear RNA proteins (snRNPs) U1, U2, U4, U5 and U6, together with approximately 80 conserved proteins. SNRNP200 is a gene required for unwinding of the U4/U6 duplex, a step essential for catalytic activation of the spliceosome (Maeder et al., 2009). SNRNP200 expression was detected in heart, brain, placenta, lung, liver, skeletal muscle, kidney, and pancreas (Zhao et al., 2009a). Mutations in SNRNP200 have recently been discovered to be associated with autosomal dominant retinitis pigmentosa (adRP) (Benaglio et al., 2011; Liu et al., 2012).

TPX2, microtubule-associated, homolog (*Xenopus laevis*) (TPX2)—TPX2 is a spindle assembly factor. It is required for normal assembly of mitotic spindles and of microtubules during apoptosis. TPX2 is required for chromatin and/or kinetochore dependent microtubule nucleation (Bird and Hyman, 2008; Moss et al., 2009). Newly synthesized TPX2 is required for nearly all Aurora A activation and for full p53 synthesis and phosphorylation in vivo during oocyte maturation (Pascreau et al., 2009). TPX2 is a cell cycle-associated protein which is over-expressed in many tumor types, such as meningiomas (Stuart et al., 2010), squamous cell carcinoma of the larynx (SCCL) (Cordes et al., 2010), oral squamous cell carcinomas (SCC) (Shigeishi et al., 2009), hepatocellular carcinomas (HCC) (Satow et al., 2010), pancreatic tumor (Warner et al., 2009), ovarian cancer (Ramakrishna et al., 2010), squamous cell carcinoma of the lung (Lin et al., 2006; Ma et al., 2006). It is frequently co-overexpressed with Aurora-A giving rise to a novel functional unit with oncogenic properties (Asteriti et al., 2010). TPX2 expression is a prognostic indicator in lung cancer (Kadara et al., 2009).

Transforming growth factor, beta-induced, 68 kDa (TGFBI)—TGFBI was first identified as a TGF-beta-inducible gene in a human lung adenocarcinoma cell line. It encodes for a secreted extracellular matrix protein, which is thought to act on cell attachment and extracellular matrix composition. Normally, the expression of TGFBI is mainly found in fibroblasts, keratinocytes, and muscle cells (Bae et al., 2002). TGFBI is over-expressed in several solid tumors such as colon (Kitahara et al., 2001), pancreas (Schneider et al., 2002) and kidney (Ivanov et al., 2008). TGFBI is down-regulated in lung cancer (Zhao et al., 2004; Shao et al., 2006), reduces the metastatic potential of lung tumor cells (Wen et al., 2011) and when over-expressed, contributes to apoptotic cell death (Zhao et al., 2006). In NSCLC samples a strong association between elevated TGFBI expression and the response to chemotherapy was observed (Irigoyen et al., 2010).

Cyclin-dependent kinase 4 (CDK4), cyclin-dependent kinase 6 (CDK6)—CDK4 is a member of the Ser/Thr protein kinase family. It is a catalytic subunit of the protein kinase complex that is important for cell cycle G1 phase progression. The activity of this kinase is restricted to the G1-to S phase transition during the cell cycle and its expression is primarily controlled at the transcriptional level (Xiao et al., 2007). CDK4 and CDK6 enzymes and their regulators, e.g., cyclins, play critical roles in embryogenesis, homeostasis, and cancerogenesis (Graf et al., 2010). In lung cancer tissues the expression level of CDK4 protein was significantly increased compared to normal tissues ($P<0.001$). Patients with higher CDK4 expression had a markedly shorter overall survival time than patients with low CDK4 expression. Multivariate analysis suggested the level of CDK4 expression was an independent prognostic indicator ($P<0.001$) for the survival of patients with lung cancer. Furthermore, suppressing CDK4 expression also significantly elevated the expression of cell cycle regulator p21 (Wu et al., 2011). In lung cells that express an endogenous K-Ras oncogene, ablation of Cdk4, but not Cdk2 or Cdk6, induces an immediate senescence response. No such response occurs in lungs expressing a single Cdk4 allele or in other K-Ras-expressing tissues. Targeting Cdk4 alleles in advanced tumors detectable by computed tomography scanning also induces senescence and prevents tumor progression (Puyol et al., 2010).

Versican (VCAN)—VCAN is a member of the aggrecan/versican proteoglycan family. VCAN is known to associate with a number of molecules in the extracellular matrix including hyaluronan, tenascin, fibulin-1, fibronectin, CD44 and L-selectin, fibrillin, integrin, and link protein (Zheng et al., 2004). VCAN is expressed in a variety of tissues. It is highly expressed in the early stages of tissue development, and its expression decreases after tissue maturation. Its expression is also elevated during wound repair and tumor growth (Ghosh et al., 2010). Knockdown in human lung adenocarcinoma (A549) cells of VCAN by RNA interference significantly inhibited tumor growth in vivo but not in vitro (Creighton et al., 2005). VCAN is a direct target of p53. High expression of VCAN has also been found in the peritumoral stromal tissue of early stage prostate cancers, and of breast cancers, and it is associated with an aggressive tumor behavior (Yoon et al., 2002).

Ubiquitin-conjugating enzyme E2S (UBE2S)—UBE2S is an APC auxiliary factor that promotes mitotic exit. Its depletion prolongs drug-induced mitotic arrest and suppresses mitotic slippage (Garnett et al., 2009). UBE2S is over-expressed in common human cancers. In esophageal cancer, UBE2S is significantly associated with the extent of tumor burden. Its positivity was linked to poor response to neoadjuvant therapy and worse survival (Chen et al., 2009). In the UBE2S promoter, binding sites for early growth response-1 (Egr-1) and serum response factor (SRF) were identified. Over-expression of these factors increased UBE2S expression which was required for cancer cell proliferation (Lim et al., 2008).

SET and MYND domain containing 3 (SMYD3)—It was previously reported that up-regulation of SMYD3, a histone H3 lysine-4-specific methyltransferase, plays a key role in the proliferation of colorectal carcinoma (CRC) and hepatocellular carcinoma (HCC). In another study, they reveal that SMYD3 expression is also elevated in the great majority of breast cancer tissues. Similarly to CRC and HCC, silencing of SMYD3 by small interfering RNA to this gene resulted in the inhibited growth of breast cancer cells, suggesting that increased SMYD3 expression is also essential for the proliferation of breast cancer cells (Hamamoto et al., 2006). Knockdown of SMYD3 by RNA interference down-regulates c-Met expression and inhibits cells migration and invasion induced by HGF (Zou et al., 2009). SMYD3 plays crucial roles in HeLa cell proliferation and migration/invasion, and it may be a useful therapeutic target in human cervical carcinomas (Wang et al., 2008).

Dystonin (DST)—

DST (BPAG1-e) encodes a member of the plakin protein family of adhesion junction plaque proteins. BPAG1-e is expressed in epithelial tissue, anchoring keratin-containing intermediate filaments to hemidesmosomes (HDs). HDs are multiprotein adhesion complexes that promote epithelial stromal attachment in stratified and complex epithelia. Modulation of their function is of crucial importance in a variety of biological processes, such as differentiation and migration of keratinocytes during wound healing and carcinoma invasion, in which cells become detached from the substrate and acquire a motile phenotype (Litjens et al., 2006). Malignant melanoma is one of the most aggressive types of tumor. BPAG1 is expressed in human melanoma cell lines (A375 and G361) and normal human melanocytes. The levels of anti-BPAG1 auto-antibodies in the sera of melanoma patients were significantly higher than in the sera of healthy volunteers ($p<0.01$). Anti-BPAG1 auto-antibodies may be a promising marker for the diagnosis of melanoma (Shimbo et al., 2010). DST was associated with breast cancer invasion (Schuetz et al., 2006). The BPAG1 gene is likely to be involved in the proliferation, apoptosis, invasion and metastasis of nasopharyngeal carcinoma NPC (Fang et al., 2005).

Solute carrier family 34 (sodium phosphate), member 2 (SLC34A2)—SLC34A2 is a pH-sensitive sodium-dependent phosphate transporter. Up-regulation of SLC34A2 gene expression in well-differentiated tumors may reflect cell differentiation processes during ovarian cancerogenesis and could serve as potential marker for ovarian cancer diagnosis and prognosis (Shyian et al., 2011). RT-PCR confirmed increased expression of SLC34A2 in papillary thyroid cancer (Kim et al., 2010b). There was also a significantly increased gene expression of SLC34A2 among breast cancer tissues compared with normal tissues (Chen et al., 2010).

Tenascin C (hexabrachion) (TNC)—Tenascin-C (TNC) is an extracellular matrix protein that is highly up-regulated in processes that are closely associated with elevated migratory activity such as embryonic development (Bartsch et al., 1992), wound healing (Mackie et al., 1988) and neoplastic processes (Chiquet-Ehrismann, 1993; Chiquet-Ehrismann and Chiquet, 2003). Furthermore, TNC is over-expressed in tumor vessels that have a high proliferative index, which indicates that TNC is involved in neoplastic angiogenesis (Kim et al., 2000). Over-expression of TNC has further been reported from colon cancer (De et al., 2013), adenoid cystic carcinoma, where it has been associated with worst prognosis (Siu et al., 2012), juvenile nasopharyngeal angiofibroma, where it possibly promotes angiogenesis (Renkonen et al., 2012), advanced melanoma (Fukunaga-Kalabis et al., 2010), pancreatic cancer, where it plays a role in proliferation, migration and metastasis (Paron et al., 2011).

Reticulocalbin 1, EF-hand calcium binding domain (RCN1), reticulocalbin 3, EF-hand calcium binding domain (RCN3)—Reticulocalbin 1 is a calcium-binding protein located in the lumen of the ER. Immunohistochemical examination demonstrated a broad distribution of RCN in various organs of fetuses and adults, predominantly in the endocrine and exocrine organs. Over-expression of RCN may play a role in tumorigenesis, tumor invasion, and drug resistance (Fukuda et al., 2007). Reticulocalbin 1 (RCN1) is a cell surface-associated protein on both endothelial (EC) and prostate cancer (PCa) cell lines. RCN1 expression on the cell surface was up-regulated by tumor necrosis factor alpha treatment of bone-marrow endothelial cells (Cooper et al., 2008). RCN1 is up-regulated in colorectal carcinoma (CRC) and was localized in cancer cells or in stromal cells near the cancer cells. It could be a novel candidate for CRC marker (Watanabe et al., 2008). RCN3 is a member of the CREC (Cab45/reticulocalbin/ERC45/calumenin) family of multiple EF-hand $Ca2+$-binding proteins localized to the secretory pathway (Tsuji et al., 2006). In oligodendrogliomas RCN3 is suggested as a potentially important candidate gene. Though little is known about the function of RCN3 (Drucker et al., 2009).

Basonuclin 1 (BNC1)—Basonuclin is a zinc-finger protein with a highly restricted tissue distribution (Tseng, 1998). Thus far, basonuclin has been detected mainly in the basal keratinocytes of stratified squamous epithelia (skin, oral epithelium, esophagus, vagina, and cornea) and in the gametogenic cells of the testis and ovary (Tseng and Green, 1994; Weiner and Green, 1998). There is now considerable evidence that basonuclin is a cell-type-specific transcription factor for rRNA genes (rDNA). The zinc fingers of basonuclin interact with three evolutionarily conserved sites within the rDNA promoter (Iuchi and Green, 1999; Tseng et al., 1999). Epigenetic regulation by CpG methylation has an important role in tumorigenesis as well as in the response to cancer therapy. BNC1 was hypomethylated in radioresistant H1299 human non-small cell lung cancer (NSCLC) cell lines. Suppression of BNC1 mRNA expression in H1299 cells also reduced the resistance of these cells to ionizing radiation (Kim et al., 2010a). Aberrant DNA methylation of BNC1 was also detected in chronic lymphocytic leukemia (CLL) samples (Tong et al., 2010). In Renal Cell Carcinoma (RCC), methylation of BNC1 was associated with a poorer prognosis independent of tumor size, stage or grade (Morris et al., 2010).

Transforming, acidic coiled-coil containing protein 3 (TACC3)—TACC3 exists in a complex with ch-TOG (colonic and hepatic tumor over-expressed gene) and clathrin that cross-links microtubules in kinetochore fibers. TACC3 is expressed in certain proliferative tissues including testis, lung, spleen, bone marrow, thymus and peripheral blood leukocytes. TACC3 expression is altered in some human tumor types. In cells, TACC3 is localized to both centrosomes and spindle microtubules but not at astral microtubules (Hood and Royle, 2011). TACC3 expression was correlated with p53 expression, and patient whose tumors highly expressed TACC3 and p53 had a significantly poorer prognosis than patients whose tumors had low-level expression for both immunostainings (P=0.006). It is suggested that increase in TACC3 may impart a proliferative advantage to NSCLC and contribute to tumor progression, and that TACC3 expression is a strong prognostic indicator of clinical outcome in NSCLC (Jung et al., 2006). Tacc3 may be a negative regulator of the Notch signaling pathway (Bargo et al., 2010).

Pecanex-like 3 (*Drosophila*) (PCNXL3)—Pecanex-like protein 3 (PCNXL3) is a multipass membrane protein; it belongs to the pecanex family. The PCNXL3 gene was mapped to the chromosomal region 11q12.1-q13. Three novel human tumor-associated translocation breakpoints were located in the chromosome 11q13 region between the markers D1154933 and D115546. Thus PCNXL3 might be an 11q13-associated disease gene (van et al., 2000).

Drosha, ribonuclease type III (DROSHA)—Drosha is a Class 2 RNase III enzyme responsible for initiating the processing of microRNA (miRNA), or short RNA molecules naturally expressed by the cell that regulate a wide variety of other genes by interacting with the RNA-induced silencing complex (RISC) to induce cleavage of complementary messenger RNA (mRNA) as part of the RNAi pathway. A microRNA molecule is synthesized as a long RNA primary transcript known as a pri-miRNA, which is cleaved by Drosha to produce a characteristic stem-loop structure of about 70 base pairs long, known as a pre-miRNA (Lee et al., 2003). Drosha exists as part of a protein complex called the Microprocessor complex, which also contains the double-stranded RNA binding protein Pasha (also called DGCR8) (Denli et al., 2004), which is essential for Drosha activity and is capable of binding single-stranded fragments of the pri-miRNA that are required for proper processing (Han et al., 2006). Human Drosha was cloned in 2000, when it was identified as a nuclear dsRNA ribonuclease involved in the processing of ribosomal RNA precursors (Wu et al., 2000). Drosha was the first human RNase III enzyme identified and cloned. The other two human enzymes that participate in the processing and activity of miRNA are the Dicer and Argonaute proteins. Both Drosha and Pasha are localized to the cell nucleus, where processing of pri-miRNA to pre-miRNA occurs. This latter molecule is then further processed by the RNase Dicer into mature miRNAs in the cell cytoplasm (Lee et al., 2003). Drosha and other miRNA processing enzymes may be important in cancer prognosis (Slack and Weidhaas, 2008)

Cell division cycle 6 homolog (*S. cerevisiae*) (CDC6)—CDC6 protein functions as a regulator at the early steps of DNA replication. It localizes in cell nucleus during cell cycle G1, but translocates to the cytoplasm at the start of S phase. Further, CDC6 is supposed to regulate replication-checkpoint activation through the interaction with ATR in higher eukaryotic cells (Yoshida et al., 2010). CDC6 is essential for DNA replication and its de-regulation is involved in carcinogenesis. It was found that CDC6 down-regulation by RNA interference (RNAi) prevented cell proliferation and promoted apoptosis (Lau et al., 2006). Over-expression of CDC6 was found in several cancers. Among the cancer types over-expressing CDC6 are gastric cancer (Tsukamoto et al., 2008), brain tumors (Ohta et al., 2001), oral squamous cell carcinoma (Feng et al., 2008), cervical carcinoma (Wang et al., 2009) and malignant mesothelioma (Romagnoli et al., 2009).

Deiodinase, iodothyronine, type II (DIO2)—The protein encoded by the DIO2 gene belongs to the iodothyronine deiodinase family. It is highly expressed in the thyroid, and may contribute significantly to the relative increase in thyroidal T3 production in patients with Graves disease and thyroid adenomas (Meyer et al., 2008); (de Souza Meyer et al., 2005)). The gene expression patterns are significantly different between upward, and downward progressing types of nasopharygeal carcinoma (NPC). The expression of DIO2 gene is higher in the downward progressing type (downward=distant metastasis) than in upward progressing type (local growth and invasion of the base of skull), which may be closely related to the metastasis potential of NPC (Liang et al., 2008a). DIO2 mRNA as well as DIO2 activity are expressed in brain tumors (Murakami et al., 2000). D2 activity in lung is present and similar in peripheral lung and lung cancer tissue (Wawrzynska et al., 2003).

Kinesin family member 26B (KIF26B)—A kinesin is a protein belonging to a class of motor proteins found in eukaryotic cells. Kinesins move along microtubule filaments, and are powered by the hydrolysis of ATP (thus kinesins are ATPases). Kif26b, a kinesin family gene, is a downstream target of Sall1 (Nishinakamura et al., 2011). Kif26b is essential for kidney development because it regulates the adhesion of mesenchymal cells in contact with ureteric buds. Over-expression of Kif26b in vitro caused increased cell adhesion through interactions with non-muscle myosin (Terabayashi et al., 2012; Uchiyama et al., 2010).

Serpin peptidase inhibitor, clade B (ovalbumin), member 3 (SERPINB3)—Squamous cellular carcinoma antigen (SCCA), also called SERPINB3, is a member of the high molecular weight family of serine protease inhibitors (serpins) (Suminami et al., 1991). High levels have been reported in cancer of the head and neck tissue and other epithelial cancers (Torre, 1998). SCCA has been reported to be over-expressed in tumoral compared to peritumoral tissue, suggesting a role as a potential marker for histological detection of HCC (Pontisso et al., 2004). Serpin B3/B4, particularly Serpin B4, appears to play an important role in aberrant epithelial proliferation. Evaluation of Serpin B3/B4 could have prognostic value in predicting disease progression, especially in patients with increased susceptibility to lung cancer (Calabrese et al., 2012). On one hand, SCCA1 (SERPINB3) inhibits cell death induced by lysosomal injury while, on the other hand, it sensitizes cells to ER stress by activating caspase-8 independently of the death receptor apoptotic pathway (Ullman et al., 2011). Some findings indicate that SERPINB3 plays an important role in the induction of epidermal barrier disruption. SERPINB3 may be a critical determinant of barrier function in the epidermis (Katagiri et al., 2010).

Cyclin-dependent kinase 1 (CDK1)—CDC2 (cell division cycle 2), also known as $p34^{cdc2}$ or CDK1 (Cyclin-dependent kinase 1), belongs to the CDKs, a family of serine/threonine protein kinases, and plays a key role in cell cycle control (Vermeulen et al., 2003). Over-expression of CDC2 was found in several cancers, although according to (Vermeulen et al., 2003) the expression of other cell cycle proteins such as cyclins is dysregulated even more frequently. Over-expression of CDC2 has been described for NSCLC (Xu et al., 2011; Zhang et al., 2011). Perumal et al. (2012) reported that over-expression of CDC2 correlated with poor prognosis (Perumal et al., 2012). Furthermore, a study suggested the possible clinical use of CDC2 as a predictor of recurrence in early-stage non-small cell lung cancer (Kubo et al., 2014).

Collagen, type XI, alpha 1 (COL11A1)—COL11A1 encodes one of the two alpha chains of type XI collagen, a minor fibrillar collagen. COL11A1 was reported to be up-regulated several cancers, e.g. in colorectal cancer (Freire et al., 2014), in breast cancer (Ellsworth et al., 2009), in gastric cancer (Zhao et al., 2009b), bladder tumors (Ewald et al., 2013). COL11A1 expression in ovarian cancer was linked to cancer recurrence and poor survival. Knockdown of COL11A1 decreased in vitro cell migration, invasion, and tumor progression in mice (Cheon et al., 2014; Wu et al., 2014b). COL11A1 was found to be differentially expressed lung tissue of nonsmoking female lung cancer patients as compared to healthy controls, based on microarray analysis (Lv and Wang, 2015).

Collagen, type I, alpha 2 (COL1A2)—COL1A2 encodes the pro-alpha2 chain of type I collagen whose triple helix comprises two alpha1 chains and one alpha2 chain. In gastric cancer samples COL1A2 was found to be up-regulated as compared to normal tissue (Yan et al., 2014; Yang et al., 2007) and associated with advanced stage (Yasui et al., 2004). COL1A2 was reported to be up-regulated in osteosarcoma (Wu et al., 2014a), in advanced stage bladder cancer (Fang et al., 2013), In head and neck/oral squamous cell carcinoma (HNOSCC) (Ye et al., 2008), and in medulloblastoma, the most common malignant brain tumor of children (Liang et al., 2008b).

Periostin, osteoblast specific factor (POSTN)—POSTN, a gene encoding a protein with similarity to the fasciclin family and involved in cell survival and angiogenesis, has emerged as a promising marker for tumor progression in various types of human cancers (Ruan et al., 2009). High expression of periostin protein or mRNA was detected in most solid tumors including breast (Zhang et al., 2010c), colon (Kikuchi et al., 2008), head and neck (Kudo et al., 2006), pancreatic (Kanno et al., 2008), papillary thyroid (Puppin et al., 2008), prostate (Tischler et al., 2010), ovarian (Choi et al., 2010), lung (Takanami et al., 2008) and liver (Utispan et al., 2010) carcinoma, as well as esophageal squamous cell carcinoma (Kwon et al., 2009). Periostin is abnormally highly expressed in lung cancer and is correlated with angiogenesis, invasion and metastasis (Takanami et al., 2008). Silencing of periostin in A549 non-small cell lung cancer (NSCLC) cells inhibits tumor cell growth and decrease cell invasion (Wu et al., 2013c).

AT hook, DNA binding motif, containing 1 (AHDC1)—This gene encodes a protein containing two AT-hooks, which likely function in DNA binding. Mutations in this gene were associated with cerebral visual impairment (Bosch et al., 2015). Using whole-exome sequencing, AHDC1 de novo truncating mutations were identified in individuals with syndromic expressive language delay, hypotonia, and sleep apnea. The mutations most likely cause this genetic syndrome (Xia et al., 2014).

Apoptosis-inducing factor, mitochondrion-associated, 2 (AIFM2)—This gene encodes a flavoprotein oxidoreductase that binds single stranded DNA and is thought to contribute to apoptosis in the presence of bacterial and viral DNA. AIFM2 is not well characterized, but limited evidence suggests that it may function as a tumor suppressor. AIFM2 expression is activated by the tumor suppressor p53, and ectopic expression of p53 has been demonstrated to induce apoptosis. Morever, AIFM2 expression was shown to be downregulated in a panel of human tumors including kidney, stomach, colorectal, and other cancer samples (Ohiro et al., 2002; Wu et al., 2004). In a knockout mouse model, however, AIFM2 was not required for p53-dependent tumor suppression (Mei et al., 2006). In cell culture, AIFM2 is involved in mediating adenosine-induced apoptosis (Yang et al., 2011).

Chromosome 6 open reading frame 132 (C6orf132)—C6orf132 encodes the chromosome 6 open reading frame 132. The gene C6orf132 is located on chromosome 6p21.1 (Mungall et al., 2003). The function of this gene is still unknown.

CCZ1 vacuolar protein trafficking and biogenesis associated homolog (S. cerevisiae) (CCZ1), CCZ1 vacuolar protein trafficking and biogenesis associated homolog B (S. cerevisiae) (CCZ1B)—CCZ1 encode CCZ1 vacuolar protein trafficking and biogenesis associated homolog (S. cerevisiae). CCZ1B encode CCZ1 vacuolar protein trafficking and biogenesis associated homolog B (S. cerevisiae). CCZ1 and CCZ1B were identified as human genes evolutionarily conserved in Caenorhabditis elegans by comparative proteomics (Lai et al., 2000). The genes CCZ1 and CCZ1 B are located on chromosome 7p22.1 (Hillier et al., 2003). CCZ1 seems to act in lysosome biogenesis and phagosome maturation by recruiting the GTPase RAB7A7 over the phagosome (Nieto et al., 2010). The CCZ1 B gene is an uncharacterized gene.

Collagen, type V, alpha 2 (COL5A2)—This gene encodes an alpha chain for one of the low abundance fibrillar collagens. COL5A2 was reported to be up-regulated in colorectal cancer tissue samples as compared to adjacent noncancerous tissues (Fischer et al., 2001). Matched samples of ductal carcinoma in situ (DCIS), invasive ductal carcinoma (IDC) and stroma of breast cancer patients revealed elevated expression of COL5A2 in IDC (Vargas et al., 2012). In osteosarcoma, COL5A2 was reported to be up-regulated and to be important in tumorigenesis (Wu et al., 2014).

Collectin sub-family member 12 (COLEC12)—This gene encodes a member of the C-lectin family, proteins that possess collagen-like sequences and carbohydrate recognition domains. The COLEC12 protein is a scavenger receptor, a cell surface glycoprotein that displays several functions associated with host defense. The COLEC12 gene was suggested to be a possible biomarker candidate for anaplastic thyroid cancer (Espinal-Enriquez et al., 2015). COLEC12 was differentially expressed in HER2-positive breast cancer cell lines BT474 and might contribute to trastuzumab efficiency (von der Heyde et al., 2015).

Coatomer protein complex, subunit gamma 1 (COPG1)—COPG1 encodes a protein subunit of the coatomer complex 1 (COPI). COPI-coated vesicles mediate retrograde transport from the Golgi back to the ER and intra-Golgi transport. The cytosolic precursor of the COPI coat, the heptameric coatomer complex, can be thought of as composed of two subcomplexes. The first consists of the beta-, gamma-, delta- and zeta-COP subunits which are distantly homologous to AP clathrin adaptor subunits (Watson et al., 2004). EGF-dependent nuclear transport of EGFR is regulated by retrograde trafficking from the Golgi to the ER involving an association of EGFR with gamma-COP, one of the subunits of the COPI coatomer (Wang et al., 2010b). By immunohistochemisty, COPG1 was confirmed to be abundantly expressed in lung cancer-derived endothelial cells and in cancerous lung cells (Park et al., 2008).

CSNK2A2—Casein kinase II subunit alpha-prime is an enzyme that in humans is encoded by the CSNK2A2 gene. A retrospective study showed that CSNK2A1 may be a useful prognosis marker in NSCLC patients after complete resection, independent of lymph node metastasis status (Wang et al., 2010c). CSNK2A2 has been associated with tumor progression in late stage human colorectal cancer (Nibbe et al., 2009).

Dendrocyte expressed seven transmembrane protein (DC-STAMP)—This gene encodes a seven-pass transmembrane protein that is primarily expressed in dendritic cells. The encoded protein is involved in a range of immunological functions carried out by dendritic cells. DCSTAMP has been identified as a differentially expressed gene in papillary thyroid carcinoma (Lee et al., 2009), and was subsequently confirmed to be expressed at elevated levels in these samples (Kim et al., 2010).

Dyskeratosis congenita 1, dyskerin (DKC1)—The DKC1 gene functions in two distinct complexes. Dyskerin mediates both the modification of uridine on ribosomal and small nuclear RNAs and the stabilization of the telomerase RNA component (TERC). In human tumors dyskerin expression was found to be associated with both rRNA modification and TERC levels (Penzo et al., 2015). Moreover, dyskerin overexpression has been linked to unfavorable prognosis in a variety of tumor types, e.g. in HCC (Liu et al., 2012).

Dual-specificity tyrosine-(Y)-phosphorylation regulated kinase 2 (DYRK2)/dual-specificity tyrosine-(Y)-phosphorylation regulated kinase 4 (DYRK4)—DYRK2 and DYRK4 belong to the family of Dyrk protein kinases (mammalian family with 5 members), which are involved in the regulation of cell differentiation, proliferation, and survival (Papadopoulos et al., 2011). DYRK2 controls the epithelial-mesenchymal transition in breast cancer by degrading Snail (Mimoto et al., 2013). DYRK2 regulates p53 to induce apoptosis and enhances the response to DNA damage: upon exposure to genotoxic stress, DYRK2 translocates into the nucleus and activates p53 by phosphorylation (Meulmeester and Jochemsen, 2008; Taira et al., 2007). The DYRK4 gene maps to chromosome 12p13.32, which was described as a susceptibility locus for CRC as the CCND2 gene is affected (Jia et al., 2013; Peters et al., 2013). Some studies have highlighted a role of DYRK4 in neuronal differentiation (Leypoldt et al., 2001; Slepak et al., 2012).

ERO1-like (S. cerevisiae) ERO1 L—ERO1-like protein alpha is a protein that in humans is encoded by the ERO1L gene. ERO1-α is an oxidizing enzyme that exists in the endoplasmic reticulum and is induced under hypoxia. ERO1-α is overexpressed in a variety of tumor types. Moreover, the cancer-associated ERO1-α regulates the expression of the MHC class I molecule via oxidative folding (Kukita et al., 2015). It has been suggested that the expression of hERO1-α in cancer cells is associated with poorer prognosis and thus can be a prognostic factor for patients with breast cancer (Kutomi et al., 2013). In natural human tumors, ERO1 L mRNA was specifically induced in hypoxic microenvironments coinciding with that of upregulated VEGF expression. It has been shown, that reduction in ERO1 L production via siRNA leads to significant inhibition of VEGF secretion, a compromised proliferation capacity and enhanced apoptosis (May et al., 2005).

Family with sequence similarity 83, member A (FAM83A)—FAM83A was determined to be elevated in several diverse cancer tissue types (Cipriano et al., 2014). However, the function of FAM83A remains unclear (Boyer et al., 2013). FAM83A was predicted a tumor-specific gene in lung cancer and its expression in lung cancer samples has been confirmed experimentally. Expression was especially high in adenocarcinoma (Li et al., 2005). Others reported a correlation with lung cancer disease progression (Liu et al., 2008).

Fragile X mental retardation, autosomal homolog 1 (FXR1)—The protein encoded by the FXR1 gene is an RNA binding protein that interacts with the functionally-similar proteins FMR1 and FXR2. FXR1 is deregulated in a variety of human disorders including cancer. FXR1 acted as an oncogene which could increase the proliferation, migration, and invasion of cancer cells (Jin et al., 2015). FXR1 is a novel cancer gene in NSCLC and FXR1 executes its regulatory function by forming a novel complex with two other oncogenes, protein kinase C, iota (PRKCI) and epithelial cell transforming 2 (ECT2) within the same amplicon in lung cancer cell (Qian et al., 2015b). It has been reported, that increased FXR1 expression in NSCLC is a candidate biomarker predictive of poor survival and might represent a novel therapeutic target. In addition, FXR1 expression correlates with poor clinical outcome in multiple human cancers, suggesting broader implications of this RNA binding protein in cancer progression (Qian et al., 2015a).

G2/M-phase specific E3 ubiquitin protein ligase (G2E3)—G2/M phase-specific E3 ubiquitin-protein ligase is an enzyme that in humans is encoded by the G2E3 gene. G2E3 shuttles between the cytoplasm and nucleus, concentrating in nucleoli and relocalizing to the nucleoplasm in response to DNA damage. G2E3 is a dual function ubiquitin ligase essential for prevention of apoptosis in early embryogenesis (Brooks et al., 2008). Some results suggest that G2E3 is a molecular determinant of the DNA damage response and cell survival, and that its loss sensitizes tumor cells towards DNA-damaging treatment (Schmidt et al., 2015b). Moreover, loss of G2E3 triggered apoptosis and decreased proliferation of cancer cells. Thus, G2E3 acts as a survival factor (Schmidt et al., 2015a).

Guanylate binding protein 5 (GBP5)—The human guanylate binding protein 5 (hGBP5) belongs to the family of interferon-gamma-inducible large GTPases, which are well known for their high induction by pro-inflammatory cytokines (Wehner and Herrmann, 2010). hGBP5 exists in three splice variants, forming two different proteins, of which the tumor-specific one is C-terminally truncated by 97 amino acids (Fellenberg et al., 2004).

Glutaminase (GLS)—The GLS gene encodes the K-type mitochondrial glutaminase. Glutaminase (GLS), which converts glutamine to glutamate, plays a key role in cancer cell metabolism, growth, and proliferation. Some studies demonstrate that GLS is required for tumorigenesis and support small molecule and genetic inhibition of GLS as potential approaches for targeting the tumor cell-autonomous dependence on GLS for cancer therapy (Xiang et al., 2015). Transient knock down of GLS splice variants indicated that loss of GAC had the most detrimental effect on NSCLC cancer cell growth (van den Heuvel et al., 2012). The expression of GLS1 is upregulated and correlates with clinicopathological factors in colorectal cancer (Huang et al., 2014a), hepatocellular carcinoma (HCC) (Yu et al., 2015) and pancreatic ductal adenocarcinomas (PDA) (Chakrabarti et al., 2015).

Heat shock 70 kDa protein 2 (HSPA2)—HSPA2 has been identified as a potential cancer-promoting protein expressed at abnormal levels in a subset of human cancers, such as breast cancer (Mestiri et al., 2001), cervical cancer (Garg et al., 2010a), bladder urothelial cancer (Garg et al., 2010c), nasopharyngeal carcinoma (Jalbout et al., 2003) and malignant tumors (Chouchane et al., 1997). Some level of the HSPA2 gene activity was also observed in cell lines derived from several human cancers (Scieglinska et al., 2008), while silencing of the HSPA2 gene in cancer cells led to growth arrest and decrease in tumorigenic potential (Rohde et al., 2005; Xia et al., 2008). Furthermore, polymorphism in the HSPA2 gene is associated with an increase in the risk of developing lung cancer (Wang et al., 2010a). Overexpression of HSPA2 is correlated with increased cell proliferation, poor differentiation and lymph node metastases in human breast cancer, cervical cancer and bladder urothelial cancer (Garg et al., 2010a; Garg et al., 2010c; Mestiri et al., 2001).

Heat shock 70 kDa protein 8 (HSPA8)—The HSPA8 gene encodes a member of the heat shock protein 70 family Hsc70, which contains both heat-inducible and constitutively expressed members. HSPA8 binds to nascent polypeptides to facilitate correct protein folding (Beckmann et al., 1990). Hsc70 function as molecular chaperones, assisting in protein synthesis, folding, assembly, trafficking between cellular compartments, and degradation (Bukau and Horwich, 1998; Hartl and Hayer-Hartl, 2002). Hsc70 is expressed in non-malignant mammary cells as well as breast cancer cells (Kao et al., 2003; Vargas-Roig et al., 1998) and the overexpression of Hsp/hsc70 in chemoresistant cancer cells (Ciocca et al., 1992; Lazaris et al., 1997) has prompted studies about possible clinical markers of these proteins (Ciocca and Calderwood, 2005). There is a potential role of this secreted hsc70 chaperone in cell proliferation that might account for the higher tumor growth of cancer cells over-expressing cathepsin D (Nirde et al., 2010). Furthermore Ruisin et al. reported an association between a polymorphism of this gene and lung cancer risk (Rusin et al., 2004).

Heat shock 70 kDa protein 1A (HSPA1A)—HSPA1A, also known as HSP72, was shown to be strongly upregulated in cancers and to play a critical role for tumor cell growth by suppressing p53-dependent and p53-independent senescence pathways (Sherman, 2010). Overexpression is described for RCC (Atkins et al., 2005) and gastrointestinal carcinomas (Wang et al., 2013a), the latter showing a significant correlation with progression, infiltration and the presence of lymph node and remote metastasis.

Heat shock 70 kDa protein 1B (HSPA1B)—HSPA1B, also known as HSP70-2, encodes the testis specific heat-shock protein 70-2, essential for the growth of spermatocytes and cancer cells (Hatfield and Lovas, 2012). Different studies suggest an important role of HSP70-2 in disease progression of cervical cancer (Garg et al., 2010b), renal cell carcinoma (Singh and Suri, 2014) and bladder cancer and polymorphisms within the gene are associated with the development of gastric cancer (Ferrer-Ferrer et al., 2013). Some functional HSPA1B variants are associated with lung cancer risk and survival. These Hsp70 genetic variants may offer useful biomarkers to predict lung cancer risk and prognosis (Szondy et al., 2012; Guo et al., 2011).

Heat shock 70 kDa protein 1-like (HSPA1L)—Heat shock 70 kDa protein 1L is a protein that in humans is encoded by the HSPA1L gene on chromosome 6. Though it shares close homology to HSPA1A and HSPA1B, it is regulated differently and is not heat-inducible (Ito et al., 1998). Polymorphisms within the gene are associated with prostate cancer susceptibility and prognosis (Sfar et al., 2010) and with hepatocellular carcinoma susceptibility (Medhi et al., 2013).

Heat shock 70 kDa protein 6 (HSP70B') (HSPA6)—Heat shock protein (Hsp) 70B' is a human Hsp70 chaperone that is strictly inducible, having little or no basal expression levels in most cells (Noonan et al., 2007). HSPA6, also known as heat shock protein 70B', was shown to be upregulated by Y15 treatment in glioblastoma cells (Huang et al., 2014b) and heat shock in head and neck cancer cells (Narita et al., 2002). High levels of HSPA6 might be associated with earlier recurrence of HCC (Yang et al., 2015).

Heat shock 70 kDa protein 7 (HSP70B) (HSPA7)—HSPA7 is a pseudogene.

HSPA (heat shock 70 kDa) binding protein, cytoplasmic cochaperone 1 (HSPBP1)—Heat shock-binding protein HspBP1 is a member of the Hsp70 co-chaperone family. HspBP1 is a co-chaperone that binds to and regulates the chaperone Hsp70. The levels of HspBP1 and Hsp70 were significantly higher in sera of breast cancer patients compared to sera of healthy individuals (Souza et al., 2009). HSPBP1 was over-expressed in patients with leukemia (Sedlackova et al., 2011). HspBP1 was up-regulated in human HCV-HCC, an increase which correlated with the increase of Hsp70 levels (Yokoyama et al., 2008).

IQ motif containing GTPase activating protein 1 (IQGAP1)—IQGAP1, also known as p195, is a ubiquitously expressed protein that in humans is encoded by the IQGAP1 gene. IQGAP1 is a key mediator of several distinct cellular processes, in particular cytoskeletal rearrangements. Recent studies have implicated a potential role for IQGAP1 in cancer, supported by the over-expression and distinct membrane localization of IQGAP1 observed in a range of tumors (Johnson et al., 2009). The over-expression of IQGAP1 may play an important role in pancreatic cancer occurrence and progression (Wang et al., 2013c). Suppressing IQGAP1 expression reduced the tumor cell growth, migration and invasion in esophageal squamous cell carcinoma (ESCC) (Wang et al., 2014c). Furthermore, increased IQGAP1 expression during the differentiation of ovarian cancer stem cell-like cells (CSC-LCs) is involved in an aggressive cell behavior, which may contribute to metastasis of ovarian cancer (Huang et al., 2015a).

Integrin, beta 6 (ITGB6)—ITGB6 is a subtype of integrin that is expressed exclusively on the surfaces of epithelial cells and is a receptor for extracellular matrix proteins (Weinacker et al., 1994). A study found increased expression of ITGB6 in 10 human tumor types studied relative to normal tissues. Highest frequency of ITGB6 expression was reported for squamous carcinomas of the cervix, skin, esophagus, and head and neck. Of note, antibody-mediated blockade of ITGB6 inhibited tumor progression in vivo (Van Aarsen et al., 2008). ITGB6 has been exploited as target for tumor-specific drug delivery and enhanced therapeutic efficacy in colon carcinoma (Liang et al., 2015; Zhao-Yang et al., 2008). In breast cancer high expression of either the mRNA or protein for ITGB6 was associated with very poor survival and increased metastases to distant sites. An antibody targeting ITGB6 inhibited tumor growth in breast cancer mouse models (Allen et al., 2014).

Lysine (K)-specific demethylase 6B (KDM6B)—KDM6B, also known as JMJD3, is a histone demethylase that in humans is encoded by the KDM6B gene. KDM6B affects transcriptional regulation by demethylating lysine 27 residue of histone 3. Low KDM6B expression was an independent predictor of poor prognosis (P=0.042) in surgically resected CRC patients (Yokoyama et al., 2008). Moreover, over-expression of KDM6B inhibited cell growth by initiating mitochondria-dependent apoptosis and by attenuating the invasion-metastasis cascade in NSCLC cells (Ma et al., 2015). On the other hand, KDM6B has high expression level in clear cell renal cell carcinoma (ccRCC) and is positively correlated with poor ccRCC prognosis. Knockdown of KDM6B could inhibit ccRCC tumorigenesis in vitro (Li et al., 2015). Furthermore, deregulation of KDM6B may contribute to gliomagenesis via inhibition of the p53 pathway resulting in a block to terminal differentiation (Ene et al., 2012).

Keratin 9, type I (KRT9)—Keratin 9 is a type I cytokeratin that in humans is encoded by the KRT9 gene. It is found only in the terminally differentiated epidermis of palms and soles. Mutations in the gene encoding this protein cause epidermolytic palmoplantar keratoderma (Reis et al., 1994). KRT9 was up-regulated in HCC. This over-expression may play a crucial role in HCC metastasis, and can be used as a potential serum marker for predicting HCC metastasis (Fu et al., 2009).

LINE1 retrotransposable element 1 (L1RE1)—The L1RE1 gene, also known as LRE1, encodes a 'LINE' (long interspersed nuclear element) retrotranposable element (LRE), a mobile DNA sequence with autonomous retrotransposon activity. The family of LINE1 retrotransposons is reportedly hypomethylated in many cancers and reflects global methylation status in the genome (Ostertag and Kazazian, Jr., 2001). One long interspersed nuclear element repeat region, LRE1, located on 22q11-q12, is a consistent indicator of global methylation status (Chalitchagorn et al., 2004; Ostertag and Kazazian, Jr., 2001). Some data suggest that LRE1 relative methylation is an independent epigenetic biomarker of head and neck squamous cell carcinoma (HNSCC) (Hsiung et al., 2007).

Laminin, beta 3 (LAMB3)—LAMB3 encodes the beta 3 subunit of laminin, which together with an alpha and a gamma subunit, forms laminin-5. LAMB3 was up-regulated in papillary thyroid carcinoma (PTC) (Barros-Filho et al., 2015), cervical squamous cell carcinoma (cervical SCC) (Yamamoto et al., 2013) and oral squamous cell carcinoma (OSCC) (Tanis et al., 2014). Gene array and bioinformatics analyses implied that LAMB3 was a key gene involved in lung cancer. Knockdown of this gene suppressed human lung cancer cell invasion and metastasis in vitro and in vivo. LAMB3 was over-expressed in lung cancer patients and its expression correlated with lymphatic metastasis (Wang et al., 2013b).

Lysosomal protein transmembrane 5 (LAPTM5)—The LAPTM5 gene encodes a membrane protein on the intracellular vesicles that is associated with lysosomes. LAPTM5 is aberrantly methylated in lung cancer, and the methylation was correlated with the differentiation state of the tumor (Cortese et al., 2008). The accumulation of LAPTM5-positive vesicles was closely associated with the programmed cell death occurring during the spontaneous regression of neuroblastomas (Inoue et al., 2009). The CD1e protein participates in the presentation of lipid antigens in dendritic cells. LATPM5 controls either CD1e ubiquitination or the generation of soluble lysosomal CD1e proteins (Angenieux et al., 2012).

Minichromosome maintenance complex component 4 (MCM4)—The protein encoded by the MCM4 gene is one of the highly conserved mini-chromosome maintenance proteins (MCM) that are essential for the initiation of eukaryotic genome replication. MCM4 was down-regulated in bladder cancer (Zekri et al., 2015) and differentially expressed in lung adenocarcinoma in comparison with normal lung tissues (Zhang et al., 2014). MCM4 over-expression was associated with shorter survival in breast cancer patients (Kwok et al., 2015).

Minichromosome maintenance complex component 5 (MCM5)—MCM5 is implicated in DNA replication and cell cycle regulation. High expression levels of MCM5 were shown to be associated with progression and poorer prognosis in oral squamous cell carcinoma (Yu et al., 2014), cervical cancer (Das et al., 2013), gastric cancer (Giaginis et al., 2011) and colon cancer (Burger, 2009).

Melanoregulin (MREG)—MREG plays a role in intracellular melanosome distribution (Wu et al., 2012), though regulation of retrograde microtubule-dependent melanosome transport (Ohbayashi et al., 2012). Moreover, MREG also functions in regulation of pigment incorporation into melanosomes (Rachel et al., 2012). MREG was shown to be targeted by miRNA-26 in its 3' UTR in estrogen receptor-positive breast cancer cells. However, a direct involvement of MREG in miRNA-26 mediated cell proliferation could not be demonstrated (Tan et al., 2014).

NODAL modulator 1 (NOMO1)/NODAL modulator 2 (NOMO2)/NODAL modulator 3 (NOMO3)—The NOMO1, NOMO2 and NOMO3 genes are three highly similar genes in a region of duplication located on the p arm of chromosome 16. These three genes encode closely related proteins that may have the same function. NOMO1 was identified as over-expressed gene in cutaneous T-cell lymphoma (CTCL) cell line HuT78 (Lange et al., 2009). NOMO1 is an antagonist of Nodal signaling. Nodals are signaling factors of the transforming growth factor-beta (TGFbeta) superfamily with a key role in vertebrate development (Haffner et al., 2004).

Nucleoporin 153 kDa (NUP153)—Nucleoporin 153 (Nup153), a component of the nuclear pore complex (NPC), has been implicated in the interaction of the NPC with the nuclear lamina. Nup153 depletion induces a dramatic cytoskeletal rearrangement that impairs cell migration in human breast carcinoma cells (Zhou and Pante, 2010). The NUP153 nucleoporin regulates the distribution of specific proteins between the nucleus and the cytoplasm, interestingly including the transducer of TGFβ signaling, SMAD2 (Xu et al., 2002). Recently, some analysis revealed novel possible oncogenic functions of nucleoporin NUP153 (ostensibly by modulating TGFβ signaling) in pancreatic cancer (Shain et al., 2013).

PERP, TP53 apoptosis effector (PERP)—PERP is a p53/p63-regulated gene encoding a desmosomal protein that plays a critical role in cell-cell adhesion and tumor suppression. Loss of PERP expression correlates with the transition to squamous cell carcinoma (SCC) and with increased local relapse in patients with oral cavity SCC (Kong et al., 2013). PERP expression was reduced in many human breast cancer cell lines (Dusek et al., 2012). Some studies suggested that Perp-deficiency promoted cancer by enhancing cell survival, desmosome loss, and inflammation (Beaudry et al., 2010). PERP is an apoptosis-associated target of p53, and its activation alone is sufficient to induce apoptotic pathway leading to cell death (Chen et al., 2011).

Putative homeodomain transcription factor 1 (PHTF1)/Putative homeodomain transcription factor 2 (PHTF2)—

PHTF1 (putative homeodomain transcriptional factor) is a putative homeobox gene located at 1p11-p13 in the human genome. This gene is evolutionarily conserved and mainly expressed in the testis (Manuel et al., 2000). As a transcription factor, the PHTF1 gene is mainly involved in biological processes such as DNA-dependent transcription and the regulation of biological processes. PHTF1 over-expression is responsible for regulating cell proliferation and apoptosis in T cell acute lymphoblastic leukemia (T-ALL) cell lines. PHTF1 may be a tumor-suppressor like gene and a therapeutic target for triggering the PHTF1-FEM1b-Apaf-1 apoptosis pathway (Huang et al., 2015b).

Putative homeodomain transcription factor 2 is a protein that in humans is encoded by the PHTF2 gene. PHTF2 is predominantly expressed in muscle and is located at 7q11.23-q21 in the human genome (Manuel et al., 2000).

Pleckstrin homology domain containing, family M (with RUN domain) member 1 (PLEKHM1)—The protein encoded by the PLEKM1 gene is essential for bone resorption, and may play a critical role in vesicular transport in the osteoclast. Mutations in this gene are associated with autosomal recessive osteopetrosis type 6 (OPTB6) (van et al., 2004). PLEKHM1 was suggested to be a candidate susceptibility gene for epithelial ovarian cancer (Permuth-Wey et al., 2013).

Phospholipid transfer protein (PLTP)—Phospholipid transfer protein (PLTP) plays an important role in regulation of inflammation. Some data suggest that PLTP has anti-inflammatory capabilities in macrophages (Vuletic et al., 2011). Moreover, PLTP is essential in mediating the association of triacyl lipid A with lipoproteins, leading to extension of its residence time and to magnification of its proinflammatory and anticancer properties (Gautier et al., 2010). PLTP was differentially expressed in breast cancer patient and might be associated with chemotherapy response (Chen et al., 2012).

Protein phosphatase 2, regulatory subunit B", alpha (PPP2R3A)—This gene encodes one of the regulatory subunits of the protein phosphatase 2. Protein phosphatase 2 (formerly named type 2A) is one of the four major Ser/Thr phosphatases and is implicated in the negative control of cell growth and division (Ruediger et al., 2001). PPP2R3A was frequently methylated in childhood acute lymphoblastic leukemia (ALL) (Dunwell et al., 2009).

PTC7 protein phosphatase homolog (*S. cerevisiae*) (PPTC7)—PPTC7 encodes PTC7 protein phosphatase homolog and is located on chromosome 12q24.11. PPTC7 was recently identified as novel susceptibility gene in response to environmental toxicants (Zhu et al., 2015).

Protein kinase, DNA-activated, catalytic polypeptide (PRKDC)—PRKDC encodes the catalytic subunit of the DNA-dependent protein kinase (DNA-PK), a member of the PI3/PI4-kinase family. It was shown that PRKDC may stabilize the c-Myc oncoprotein via Akt/GSK3 pathway (An et al., 2008). Activation of PRKDC positively correlated with HCC proliferation, genomic instability and microvessel density, and negatively with apoptosis and patient's survival (Evert et al., 2013).

Proteasome (prosome, macropain) subunit, alpha type, 4 (PSMA4)—PSMA4 encodes proteasome subunit alpha 4, which cleaves peptides in an ATP/ubiquitin-dependent process in a non-lysosomal pathway. Single nucleotide polymorphisms in the PSMA4 gene have been associated with the risk of lung cancer in Chinese Han population (Wang et al., 2015). On the other side, it has been reported that single nucleotide polymorphisms in the PSMA4 gene are not major contributors to non-small cell lung cancer susceptibility (Yongjun Zhang et al., 2013). Furthermore, over-expression of PSMA4 was observed in lung tumors compared with normal lung tissues. Down-regulation of PSMA4 expression decreased proteasome activity and induced apoptosis (Liu et al., 2009).

Protein tyrosine phosphatase, non-receptor type 13 (PTPN13)—This gene encodes a member of the protein tyrosine phosphatase (PTP) family. PTPs are signaling molecules that regulate a variety of cellular processes including cell growth, differentiation, mitotic cycle and oncogenic transformation. PTPN13 was found to interact with the Fas receptor and might therefore have a role in Fas mediated programmed cell death. Moreover, PTPN13 interacts with GTPase-activating protein and thus may function as a regulator of Rho signaling pathways. In hematological malignancies PTPN13 has contradictory effects, either suppressing or promoting tumor growth, in lymphoma and in myeloid leukemia, respectively (Wang et al., 2014b). This can be explained by the capacity of PTPN13 to counteract the activity of oncogenic tyrosine kinases and its inhibitory interaction with the Fas death receptor (Freiss and Chalbos, 2011). In breast cancer, PTPN13 was regarded as a unique marker of mammary tumor response to antiestrogens and a potential therapeutic target to activate apoptotic stimuli in tumor cells (Freiss et al., 2004). The inhibition of the Fas/PTPN13 binding might provide a good target to develop anti-cancer drugs (Takahashi and Kataoka, 1997).

RAS p21 protein activator 2 (RASA2)—RAS p21 protein activator 2 encodes a member of the GAP1 family of GTPase-activating proteins. Acting as a suppressor of RAS function, RASA2 enhances the weak intrinsic GTPase activity of RAS proteins resulting in the inactive GDP-bound form of RAS, thereby allowing control of cellular proliferation and differentiation. Depending on the precise genetic alteration, its location within the gene and the effects it exerts on protein function, RASA2 can theoretically function as either an oncogene or as a tumor suppressor gene (Friedman, 1995). Under mild stress conditions, RASA2 is cleaved by caspase-3 which results in a fragment called fragment N stimulating anti-death signaling. When caspase-3 activity further increases, this generates a fragment, called N2, which no longer protects cells. On the other hand, full-length RASA2 favors Akt activity by shielding it from deactivating phosphatases (Cailliau et al., 2015). In breast cancer, stress-activated caspase-3 might contribute to the suppression of metastasis through the generation of fragment N2 (Barras et al., 2014). RASA2 was identified as a tumor-suppressor gene mutated in 5% of melanomas (Arafeh et al., 2015).

Recombination signal binding protein for immunoglobulin kappa J region (RBPJ)—Recombination signal binding protein for immunoglobulin kappa J region encodes a transcriptional regulator important in the Notch signaling pathway. RBPJ acts as a repressor when not bound to Notch proteins and an activator when bound to Notch proteins. It is thought to function by recruiting chromatin remodeling complexes containing histone deacetylase or histone acetylase proteins to Notch signaling pathway genes. Xenograft mouse models showed that RBPJ knockdown inhibited tumorigenicity and decreased tumor volume suggesting that hypoxia promotes Smoothened transcription through up-regulation of RBPJ to induce proliferation, invasiveness and tumorigenesis in pancreatic cancer (Onishi et al., 2016). The effect that RBPJ knockdown led to a significant decrease in cell growth was also found in prostate and lung cancer cells, suggesting that RBPJ expression could be a promising therapeutic approach for treating human cancer (Xue et al., 2015; Lv et al., 2015). Moreover, over-expression of RBPJ promoted the anchorage-independent growth of rhabdomyosarcoma cells (Nagao et al., 2012). The RBPJ-mediated Notch signaling is also essential for dendritic cell-dependent anti-tumor immune responses (Feng et al., 2010).

Sterile alpha motif domain containing 9-like (SAMD9L)—SAMD9L encodes sterile alpha motif domain containing 9-like and is located on chromosome 7q21.2. SAMD9 and SAMD9L genes share a common gene structure and encode proteins with 60% amino acid identity with a suggested role in suppressing inflammatory pathways. SAMD9L localizes in early endosomes and acts as an endosome fusion facilitator. Haploinsufficiency of SAMD9L gene contributes to myeloid transformation and SAMD9L was identified as candidate myeloid tumor suppressor gene (Nagamachi et al., 2013). SAMD9L knockdown significantly promoted cell proliferation and colony formation of hepatocellular carcinoma cell lines as SAMD9L silence facilitated G1-S transition of cell cycle progression and led to the elevated activity of Wnt/beta-catenin pathway. Recent findings highlight the tumor-suppressive role of SAMD9L inactivation by somatic mutation and decreased expression in human cancers (Wang et al., 2014a). SAMD9L exhibited significantly decreased expression in T and B cell populations of patients with metastatic melanoma as compared with those from healthy control individuals (Critchley-Thorne et al., 2007).

Splicing factor 3b, subunit 3, 130 kDa (SF3B3)—SF3B3 encodes subunit 3 of the splicing factor 3b protein complex. Over-expression of SF3B3 is significantly correlated with overall survival and endocrine resistance in estrogen receptor-positive breast cancer (Gokmen-Polar et al., 2015).

Surfactant protein A1 (SFTPA1)/Surfactant protein A2 (SFTPA2)—These genes encode lung surfactant proteins that are a member of a subfamily of C-type lectins called collectins. SFTPAs bind specific carbohydrate moieties found on lipids and on the surface of microorganisms and play an essential role in surfactant homeostasis and in the defense against respiratory pathogens. Mutations in these genes are associated with idiopathic pulmonary fibrosis. A lung cancer-specific gene signature, containing SFTPA1 and SFTPA2 genes, accurately distinguished lung cancer from other cancer samples (Peng et al., 2015). EGFR mutations were significantly more common in pulmonary adenocarcinoma with SFTPA expressions than in those without (Jie et al., 2014). SFTPA suppresses lung cancer progression by regulating the polarization of tumor-associated macrophages (Mitsuhashi et al., 2013). Expression of mutant SFTPA2 in lung epithelial cells leads to secretion of latent TGF-beta1 and TGF-beta1 mediated EMT (Maitra et al., 2012). Moreover, the development of prostate cancer may be related to decreased level of SFTPA (Kankavi et al., 2014).

Solute carrier family 25 (mitochondrial carrier; adenine nucleotide translocator), member 31 (SLC25A31)/solute carrier family 25 (mitochondrial carrier; adenine nucleotide translocator), member 4 (SLC25A4)/solute carrier family 25 (mitochondrial carrier; adenine nucleotide translocator), member 5 (SLC25A5)/solute carrier family 25 (mitochondrial carrier; adenine nucleotide translocator), member 6 (SLC25A6)—Proteins of the solute carrier family 25 are ADP/ATP carrier that exchange cytosolic ADP for matrix ATP in the mitochondria. They function as a gated pore that translocates ADP/ATP and form a homodimer embedded in the inner mitochondria membrane. Cells over-expressing this gene family have been shown to display an anti-apoptotic phenotype. Suppressed expression of this gene family has been shown to induce apoptosis and inhibit tumor growth. While SLC25A4 is preferentially present in differentiated tissues and is specific for muscle and brain, SLC25A5 is expressed in proliferating tissues such as tumors. SLC25A6 is expressed ubiquitously and SLC25A31 is present in liver and germ cells (Dolce et al., 2005). Especially SLC25A5 contributes to carcinogenesis. Since the expression of SLC25A5 is closely linked to the mitochondrial bioenergetics of tumors, it is a promising target for individualizing cancer treatments and for the development of anticancer strategies (Chevrollier et al., 2011). Moreover, stable over-expression of SLC25A31 protected cancer cells from ionidamine and staurosporine apoptosis independent of Bcl-2 expression. Therefore, dichotomy is found in the human SLC25 isoform sub-family with SLC25A4 and SLC25A6 isoforms functioning as pro-apoptotic, while SLC25A5 and SLC25A31 isoforms render cells resistant to death inducing stimuli (Gallerne et al., 2010).

SP140 nuclear body protein (SP140)—SP140 encodes the SP140 nuclear body protein and is located on chromosome 2q37.1. SP140 was shown to be up-regulated in laryngeal squamous cell carcinoma (Zhou et al., 2007). SP140 is associated with chronic lymphocytic leukemia (Lan et al., 2010), multiple myeloma (Kortum et al., 2015) and acute promyelocytic leukemia (Bloch et al., 1996).

Signal transducer and activator of transcription 1, 91 kDa (STAT1)—STAT1 is activated by tyrosine phosphorylation in response to all interferons (Decker et al., 2002) and contributes to Th1 cell differentiation (Schulz et al., 2009). At the molecular level, STAT1 inhibits the proliferation of both mouse and human tumor cells treated with IFN-γ via its ability to increase the expression of cyclin-dependent kinase inhibitor p21Cip1, or to decrease c-myc expression (Ramana et al., 2000). The anti-tumor activity of STAT1 is further supported by its ability to inhibit angiogenesis and tumor metastasis in mouse models (Huang et al., 2002). Increased STAT1 mRNA levels were shown to be part of a molecular signature associated with better prediction of the metastatic outcome for patients with hormone receptor negative and triple-negative breast cancers (Yau et al., 2010).

Transmembrane protein 43 (TMEM43)—This gene encodes transmembrane protein 43. Defects in this gene are the cause of familial arrhythmogenic right ventricular dysplasia type 5 (ARVD5), also known as arrhythmogenic right ventricular cardiomyopathy type 5 (ARVC5). ARVD is an inherited disorder and is characterized by ventricular tachycardia, heart failure, sudden cardiac death and fibrofatty replacement of cardiomyocytes (Siragam et al., 2014). TMEM43 may have an important role in maintaining nuclear envelope structure by organizing protein complexes at the inner nuclear membrane (Bengtsson and Otto, 2008).

Topoisomerase (DNA) II alpha 170 kDa (TOP2A)/topoisomerase (DNA) II beta 180 kDa (TOP2B)—TOP2A and TOP2B encode highly homologous isoforms of a DNA topoisomerase, an enzyme that controls and alters the topologic states of DNA during transcription. This nuclear enzyme is involved in processes such as chromosome condensation, chromatid separation, and the relief of torsional stress that occurs during DNA transcription and replication. TOP2A is essential for cell proliferation and is highly expressed in vigorously growing cells, whereas TOP2B is nonessential for growth and has recently been implicated in treatment-associated secondary malignancies (Toyoda et al., 2008). TOP2A has found to be over-expressed in several cancer types (e.g. malignant pleural mesothelioma (Roe et al., 2010), malignant peripheral nerve sheath tumor (Kresse et al., 2008), lung adenocarcinoma cells (Kobayashi et al., 2004), bladder cancer (Simon et al., 2003), glioblastomas (van den Boom et al., 2003)). TOP2B is involved in DNA transcription, replication, recombination, and mitosis, and besides TOP1, represents the second NUP98 fusion partner gene that belongs to the topoisomerase gene family (Nebral et al., 2005).

Tryptase alpha/beta 1 (TPSAB1)/tryptase beta 2 (TPSB2)—Tryptase alpha/beta 1 (TPSAB1) and tryptase beta 2 (TPSB2) are together with two other tryptase isoforms, expressed by mast cells. Tryptases have been implicated as mediators in the pathogenesis of asthma and other allergic and inflammatory disorders. Tryptase secreted by mast cells has pro-angiogenic function and contributes to tumor vascularization. Tryptase acts by activation of protease-activated receptor-2 (PAR-2) and additionally contributes to extracellular matrix degradation, thus also facilitating vessel growth. Moreover, the presence of tryptase-positive mast cells in tumor tissue correlates with angiogenesis in several cancer types (Ammendola et al., 2014). Elevated levels of tryptase-positive mast cells have been reported in prostate cancer and have been correlated with microvessel density, tumor stage, and shorter survival (Nonomura et al., 2007; Stawerski et al., 2013). Similarly, tryptase-positive mast cells are also associated with tumor stage and angiogenesis in gastric cancer (Zhao et al., 2012; Ribatti et al., 2010) as well as in lung adenocarcinoma (Imada et al., 2000; Takanami et al., 2000).

Tripartite motif containing 11 (TRIM11)—Tripartite motif-containing protein 11 is a protein that in humans is encoded by the TRIM11 gene. TRIM11 is known to be involved in the development of the central nervous system and to destabilize humanin, an inhibitor of Alzheimer-like neuronal insults (Niikura et al., 2003). TRIM11 is overexpressed in high-grade gliomas and promotes proliferation, invasion, migration and glial tumor growth (Di et al., 2013).

Transient receptor potential cation channel, subfamily M, member 2 (TRPM2)—The protein encoded by this gene is a calcium-permeable cation channel that is regulated by free intracellular ADP-ribose. TRPM2 might be involved in mediating apoptosis under certain conditions (Ishii et al., 2007; Cao et al., 2015). However, its effect on cell growth proliferation is less clear and might depend on cell culture conditions and the expression of alternatively spliced isoforms (Chen et al., 2014). In melanoma and prostate cancer, a tumor-enriched TRPM2 antisense transcript has been identified which is correlated with apoptosis and clinical outcome (Orfanelli et al., 2015).

Tubulin gamma complex associated protein 3 (TUBGCP3)—Tubulin gamma complex associated protein 3 is part of the multi-subunit gamma-tubulin complex that is critical for microtubule nucleation in eukaryotic cells (Lynch et al., 2014). Cytoplasmic gamma-tubulin complexes are targeted to centrosomes or to other microtubule organizing centers via a set of so called gamma-tubulin complex binding proteins (Schiebel, 2000). A significant increase in the expression of TUBGCP3 transcripts in glioblastoma cells versus normal human astrocytes was found and TUBGCP3 immunoreactivity was significantly increased over that in normal brains. TUBGCP3 was also associated with microvascular proliferation and interaction with signaling pathways leading to a malignant phenotype (Draberova et al., 2015). Moreover, TUBGCP3 was found to be significantly higher expressed in near-tetraploid than in diploid mantle cell lymphoma samples (Neben et al., 2007).

Ubiquitin-like modifier activating enzyme 6 (UBA6)—Ubiquitin-like modifier-activating enzyme 6 is a protein that in humans is encoded by the UBA6 gene. UBA6 is an ubiquitin-activating enzyme being most abundantly expressed in the testis. Further it is required for cellular response to DNA damage (Moudry et al., 2012).

Xenotropic and polytropic retrovirus receptor 1 (XPR1)—XPR1 is a multipass membrane molecule that contains a 180-residue-long aminoterminal SPX domain (named after SYG1, Pho81, and XPR1). XPR1 has been reported to mediate phosphate export (Giovannini et al., 2013). Upon osteoclast differentiation XPR1 mRNA transcripts were found to increase (Sharma et al., 2010). Originally, XPR1 was described as retroviral receptor, used by xenotropic and polytropic MLV (X-MLV and P-MLV) two gammaretroviruses that can infect human cells as well as various other species, such as mice and birds (Kozak, 2010; Martin et al., 2013).

Zinc finger BED-type containing 5 (ZBED5)—Zinc finger BED-type containing 5 is characterized by a coding sequence that is mostly derived from Charlie-like DNA transposon, however, it does not appear to be an active DNA transposon as it is not flanked by terminal inverted repeats. ZBED5 is related to Buster DNA transposons and is phylogenetically separate from other ZBED5. ZBED genes are widely expressed among vertebrate tissues and together they regulate a remarkable diversity of functions (Hayward et al., 2013).

Zinc finger protein 697 (ZNF697)—The ZNF697 gene encodes zinc finger protein 697 that is located on chromosome 1p12 and probably plays a role in DNA binding (Yu et al., 2011).

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or 13 or longer, and in case of MHC class II peptides (elongated variants of the peptides of the invention) they can be as long as 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 11

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to HLA-A*02 and HLA-A*24. The MHC class II peptides of the invention bind to several different HLA class II molecules and are called promiscuous binders (pan-binding peptides). A vaccine may also include pan-binding MHC class II peptides. Therefore, the vaccine of the invention can be used to treat cancer in patients that are A*02 or A*24 positive, whereas no selection for MHC class II allotypes is necessary due to the pan-binding nature of these peptides.

If A*02 peptides of the invention are combined with A*24 peptides of the invention, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 110 or a variant thereof which is 88% homologous to SEQ ID NO: 1 to SEQ ID NO: 110, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 110. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 110, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 12

Preferred variants and motif of the HLA-A*02 peptides according to SEQ ID NO: 1, 2 and 4

| Position | 1 | 2 | 3 | 4 | 5 | 6 | 7 | 8 | 9 |
|---|---|---|---|---|---|---|---|---|---|
| SEQ ID 1 | K | L | L | P | Y | I | V | G | V |
| Variant | | | | | | | | | I |
| | | | | | | | | | L |
| | | | | | | | | | A |
| | | M | | | | | | | |
| | | M | | | | | | | I |
| | | M | | | | | | | L |
| | | M | | | | | | | A |
| | | A | | | | | | | |
| | | A | | | | | | | I |
| | | A | | | | | | | L |
| | | A | | | | | | | A |
| | | V | | | | | | | |
| | | V | | | | | | | I |
| | | V | | | | | | | L |
| | | V | | | | | | | A |

TABLE 12-continued

Preferred variants and motif of the HLA-A*02 peptides according to SEQ ID NO: 1, 2 and 4

| Position | 1 | 2 | 3 | 4 | 5 | 6 | 7 | 8 | 9 |
|---|---|---|---|---|---|---|---|---|---|
| | | T | | | | | | | |
| | | T | | | | | | | I |
| | | T | | | | | | | L |
| | | T | | | | | | | A |
| | | Q | | | | | | | |
| | | Q | | | | | | | I |
| | | Q | | | | | | | L |
| | | Q | | | | | | | A |
| SEQ ID 2 | F | L | I | P | Y | A | I | M | L |
| Variant | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |
| SEQ ID 4 | F | V | F | S | F | P | V | S | V |
| Variant | | L | | | | | | | |
| | | L | | | | | | | I |
| | | L | | | | | | | L |
| | | L | | | | | | | A |
| | | M | | | | | | | |
| | | M | | | | | | | I |
| | | M | | | | | | | L |
| | | M | | | | | | | A |
| | | A | | | | | | | |
| | | A | | | | | | | I |
| | | A | | | | | | | L |
| | | A | | | | | | | A |
| | | | | | | | | | I |
| | | | | | | | | | L |
| | | | | | | | | | A |
| | | T | | | | | | | |
| | | T | | | | | | | I |
| | | T | | | | | | | L |
| | | T | | | | | | | A |
| | | Q | | | | | | | |
| | | Q | | | | | | | I |
| | | Q | | | | | | | L |
| | | Q | | | | | | | A |

TABLE 12B

Preferred variants and motif of the HLA-A*02 peptide according to SEQ ID NO: 13

| Position | 1 | 2 | 3 | 4 | 5 | 6 | 7 | 8 | 9 |
|---|---|---|---|---|---|---|---|---|---|
| SEQ ID 13 | F | L | F | D | G | S | A | N | L |
| Variant | | | | | | | | | V |
| | | | | | | | | | I |
| | | | | | | | | | A |

TABLE 12B-continued

Preferred variants and motif of the HLA-A*02 peptide according to SEQ ID NO: 13

| Position | 1 | 2 | 3 | 4 | 5 | 6 | 7 | 8 | 9 |
|---|---|---|---|---|---|---|---|---|---|
|  |  | M |  |  |  |  |  |  | V |
|  |  | M |  |  |  |  |  |  | I |
|  |  | M |  |  |  |  |  |  |  |
|  |  | M |  |  |  |  |  |  | A |
|  |  | A |  |  |  |  |  |  | V |
|  |  | A |  |  |  |  |  |  | I |
|  |  | A |  |  |  |  |  |  |  |
|  |  | A |  |  |  |  |  |  | A |
|  |  | V |  |  |  |  |  |  | V |
|  |  | V |  |  |  |  |  |  | I |
|  |  | V |  |  |  |  |  |  |  |
|  |  | V |  |  |  |  |  |  | A |
|  |  | T |  |  |  |  |  |  | V |
|  |  | T |  |  |  |  |  |  | I |
|  |  | T |  |  |  |  |  |  |  |
|  |  | T |  |  |  |  |  |  | A |
|  |  | Q |  |  |  |  |  |  | V |
|  |  | Q |  |  |  |  |  |  | I |
|  |  | Q |  |  |  |  |  |  |  |
|  |  | Q |  |  |  |  |  |  | A |

TABLE 13

Preferred variants and motif of the HLA-A*24 peptides according to SEQ ID NO: 23, 24 and 25

| Position | 1 | 2 | 3 | 4 | 5 | 6 | 7 | 8 | 9 | 10 | 11 |
|---|---|---|---|---|---|---|---|---|---|---|---|
| SEQ ID 23 | V | Y | T | S | W | Q | I | P | Q | K | F |
| Variant |  |  |  |  |  |  |  |  |  |  | I |
|  |  |  |  |  |  |  |  |  |  |  | L |
|  |  | F |  |  |  |  |  |  |  |  | I |
|  |  | F |  |  |  |  |  |  |  |  | L |
|  |  | F |  |  |  |  |  |  |  |  |  |
| SEQ ID 24 | N | Y | P | K | S | I | H | S | F |  |  |
| Variant |  |  |  |  |  |  |  |  | I |  |  |
|  |  |  |  |  |  |  |  |  | L |  |  |
|  |  | F |  |  |  |  |  |  | I |  |  |
|  |  | F |  |  |  |  |  |  | L |  |  |
|  |  | F |  |  |  |  |  |  |  |  |  |
| SEQ ID 25 | R | F | M | D | G | H | I | T | F |  |  |
| Variant |  | Y |  |  |  |  |  |  | I |  |  |
|  |  | Y |  |  |  |  |  |  | L |  |  |
|  |  | Y |  |  |  |  |  |  |  |  |  |
|  |  |  |  |  |  |  |  |  | I |  |  |
|  |  |  |  |  |  |  |  |  | L |  |  |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 14.

TABLE 14

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 110.

"Consisting essentially of" shall mean that a peptide according to the present invention, in addition to the sequence according to any of SEQ ID NO: 1 to SEQ ID NO 110 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other alpha-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004) and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from lung cancer (NSCLC) samples (N=91 A*02-positive samples and N=80 A*24-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 155 lung cancer (NSCLC) patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from lung cancer (NSCLC) tissue samples were purified and HLA-associated peptides were isolated and analyzed by LC-MS (see examples). All TUMAPs contained in the present application were identified with this approach on primary lung cancer (NSCLC) samples confirming their presentation on primary lung cancer (NSCLC).

TUMAPs identified on multiple lung cancer (NSCLC) and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2.x allows for the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see examples and Table 22).

The present invention provides peptides that are useful in treating cancers/tumors, preferably lung cancer that over- or exclusively present the peptides of the invention. These peptides were shown by mass spectrometry to be naturally presented by HLA molecules on primary human lung cancer (NSCLC) samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy lung cells or other normal tissue cells, demonstrating a high degree of tumor association of the source genes (see example 2). Moreover, the peptides themselves are strongly over-presented on tumor tissue—"tumor tissue" in relation to this invention shall mean a sample from a patient suffering from lung cancer (NSCLC), but not on normal tissues (see example 1).

HLA-bound peptides can be recognized by the immune system, specifically T lymphocytes. T cells can destroy the cells presenting the recognized HLA/peptide complex, e.g. lung cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see example 3, example 4). Furthermore, the peptides when complexed with the respective MHC can be used for the production of antibodies, specifically binding fragments thereof, antibody-like binders and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Additional methods for the production are disclosed in WO 2013/057586A1.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 110, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides.

The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, Juvlmmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 110, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 110, or a variant thereof which is at least 88% homologous (preferably identical) to SEQ ID NO: 1 to SEQ ID NO: 110 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 110 or a variant thereof which is at least 88% homologous (preferably identical) to SEQ ID NO: 1 to SEQ ID NO: 110, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 110.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of lung cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 110 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are lung cancer cells or other solid or hematological tumor cells such as brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), esophageal cancer including cancer of the gastric-esophageal junction (OSCAR), gallbladder cancer and cholangiocarcinoma (GBC, CCC), urinary bladder cancer (UBC), and uterine cancer (UEC).

The present invention further relates to particular marker proteins and biomarkers based on the peptides according to the present invention, herein called "targets" that can be used in the diagnosis and/or prognosis of lung cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a lung cancer marker (poly)peptide, delivery of a toxin to a lung cancer cell expressing a cancer marker gene at an increased level, and/or inhibiting the activity of a lung cancer marker polypeptide) according to the invention.

Whenever possible, the antibodies of the invention may be purchased from commercial sources. The antibodies of the invention may also be generated using well-known methods. The skilled artisan will understand that either full length lung cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 110 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the lung cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014). For example, the antibodies may be tested in ELISA assays or, Western blots, immunohistochemical staining of formalin-fixed lung cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating lung cancer, the efficacy of the therapeutic antibody can be assessed in various ways well known to the skilled practitioner. For instance, the size, number, and/or distribution of lung cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of lung cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1 \times 10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 110, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, and vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 110.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from lung cancer, the medicament of the invention is preferably used to treat lung cancer.

The present invention further relates to a method for producing a personalized pharmaceutical (composition) for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly over-expressed in the tumor tissue of lung cancer patients with various HLA-A HLA-B and HLA-C alleles. It may contain MHC class I and MHC class II peptides or elongated MHC class I peptides. In addition to the tumor associated peptides collected from several lung cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, lung cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (lung cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from lung cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumine). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from lung cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for lung cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

EXAMPLES

Example 1

Identification and Quantitation of Tumor Associated Peptides Presented on the Cell Surface Tissue Samples Patients' tumor tissues were obtained from University Hospital of Heidelberg; University Hospital of Munich. Normal (healthy) tissues were obtained from Bio-Options Inc., CA, USA; BioServe, Beltsville, Md., USA; Capital BioScience Inc., Rockville, Md., USA; Geneticist Inc., Glendale, Calif., USA; University Hospital of Geneva; University Hospital of Heidelberg; Kyoto Prefectural University of Medicine (KPUM); Osaka City University (OCU); University Hospital Munich; ProteoGenex Inc., Culver City, Calif., USA; University Hospital of Tübingen.

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose lung cancer samples to a baseline of normal tissue samples.

Presentation profiles of exemplary over-presented peptides are shown in FIG. 1. Presentation scores for exemplary peptides are shown in Table 15 and Table 16.

TABLE 15

Presentation scores.

| SEQ ID No. | Sequence | Peptide Code | Peptide Presentation |
|---|---|---|---|
| 1 | KLLPYIVGV | COL6A3-010 | +++ |
| 2 | FLIPYAIML | SLC6A14-001 | +++ |
| 3 | FLYDVVKSL | COL6A3-007 | ++ |
| 4 | FVFSFPVSV | DUSP4-001 | + |
| 5 | ALTSTLISV | GPNM-002 | ++ |
| 9 | ALSGTLSGV | MCM5-001 | ++ |
| 13 | FLFDGSANL | COL6A3-008 | +++ |
| 14 | LIQDRVAEV | LAMB3-001 | + |
| 15 | ELDRTPPEV | SF3B3-001 | + |
| 16 | LIFDLGGGTFDV | HSP-003 | + |
| 17 | TLLQEQGTKTV | KRT-006 | + |
| 18 | ILLTEQINL | PHT-001 | + |
| 20 | LMTKEISSV | PRKDC-001 | + |

TABLE 15-continued

Presentation scores.

| SEQ ID No. | Sequence | Peptide Code | Peptide Presentation |
|---|---|---|---|
| 21 | VLSSGLTAA | CSNK2A2-001 | + |
| 94 | ILVDWLVQV | CCNB2-001 | +++ |
| 96 | AMGIAPPKV | PRPF3-001 | + |
| 97 | TLFPVRLLV | LPCAT1-001 | + |
| 98 | VLYPHEPTAV | DONSON-001 | ++ |
| 99 | ALFQRPPLI | DKC-001 | + |
| 101 | LLLEILHEI | ER0-001 | + |
| 102 | SLLSELQHA | GBP5-001 | ++ |
| 103 | KLLSDPNYGV | TMEM43-001 | + |
| 105 | IVAESLQQV | STA-002 | + |
| 111 | SLYKGLLSV | RAD54B-001 | +++ |
| 112 | VLAPLFVYL | FZD-001 | ++ |
| 113 | FLLDGSANV | COL6A3-002 | +++ |
| 114 | AMSSKFFLV | WNT5A-001 | ++ |
| 115 | YVYQNNIYL | FAP-003 | + |
| 116 | KIQEMQHFL | MMP12-003 | +++ |
| 117 | ILIDWLVQV | CCNB1-002 | ++ |
| 118 | SLHFLILYV | ATP-001 | + |
| 119 | IVDDITYNV | FN1-001 | ++ |
| 120 | KIQEILTQV | IGF2BP3-001 | +++ |
| 121 | RLLDSVSRL | LAMC2-001 | + |
| 122 | KLSWDLIYL | CERC-001 | + |
| 123 | GLTDNIHLV | MXRA5-002 | ++ |
| 124 | NLLDLDYEL | COL6A3-003 | +++ |
| 125 | RLDDLKMTV | LAMC2-002 | ++ |
| 126 | KLLTEVHAA | ADAM8-001 | ++ |
| 127 | ILFPDIIARA | MAGEF1-001 | + |
| 128 | TLSSIKVEV | MXRA5-001 | +++ |
| 129 | GLIEIISNA | SNRNP20-001 | + |
| 130 | KILEDVVGV | TPX2-001 | + |
| 131 | ALVQDLAKA | CCNB1-001 | + |
| 132 | ALFVRLLALA | TGFBI-001 | ++ |
| 133 | RLASYLDKV | KRT-007 | + |
| 134 | TLVVYRAPEV | CDK4-001 | + |
| 136 | ALVDHTPYL | VCAN-002 | + |
| 137 | FLVDGSWSV | COL12A1-002 | ++ |
| 138 | ALNEEAGRLLL | UBE2S-001 | ++ |
| 139 | SLIEDLILL | SMYD3-001 | ++ |
| 142 | VLLPVEVATHYL | SLC34A2-001 | + |
| 143 | AIVDKVPSV | COPG1-001 | + |
| 144 | KIFDEILVNA | TOP-001 | + |
| 145 | AMTQLLAGV | TNC-001 | + |
| 146 | FQYDHEAFL | RCN1-001 | ++ |
| 148 | ALFGALFLA | PLT-001 | + |
| 149 | KLVEFDFLGA | TACC3-001 | + |
| 150 | GVLENIFGV | PCNXL3-001 | + |
| 152 | ILQDRLNQV | CDC6-001 | + |
| 153 | ALYDSVILL | DIO2-001 | ++ |
| 156 | TVAEVIQSV | KIF26B-001 | + |

The table lists HLA-A*02 peptides that are very highly over-presented on tumors compared to a panel of normal tissues (+++), highly over-presented on tumors compared to a panel of normal (healthy) tissues (++) or over-presented on tumors compared to a panel of normal tissues (+).

TABLE 16

Presentation scores.

| SEQ ID No. | Sequence | Peptide Code | Peptide Presentation |
|---|---|---|---|
| 23 | VYTSWQIPQKF | CCL18-001 | +++ |
| 24 | NYPKSIHSF | MMP12-005 | +++ |
| 25 | RFMDGHITF | LAMP3-001 | +++ |
| 26 | RYLEKFYGL | MMP12-006 | +++ |
| 27 | RYPPPVREF | COL6A3-012 | +++ |
| 28 | RYLDSLKAIVF | CENPN-001 | +++ |
| 29 | YYTKGFALLNF | PLOD2-002 | +++ |
| 30 | KYLEKYYNL | MMP1-001 | +++ |
| 31 | SYLDKVRAL | KRT-008 | +++ |
| 32 | EYQPEMLEKF | COL6A3-013 | +++ |
| 33 | TYSEKTTLF | MUC16-001 | +++ |
| 34 | VFMKDGFFYF | MMP1-002 | +++ |
| 35 | TYNPEIYVI | ITGA2-002 | +++ |
| 36 | YYGNTLVEF | OLFML2B-001 | +++ |
| 37 | RYLEYFEKI | TTC13-001 | +++ |

TABLE 16-continued

Presentation scores.

| SEQ ID No. | Sequence | Peptide Code | Peptide Presentation |
|---|---|---|---|
| 38 | VFLNRAKAVFF | GPNM-003 | +++ |
| 39 | KFLEHTNFEF | DOCK2-001 | +++ |
| 40 | IYNPSMGVSVL | PVRL1-001 | +++ |
| 41 | TYIGQGYII | FKBP10-002 | +++ |
| 42 | VYVTIDENNIL | ABCC1-001 | +++ |
| 43 | RYTLHINTL | ALOX15B-001 | +++ |
| 44 | IYNQIAELW | SMPDL3B-001 | +++ |
| 45 | KFLESKGYEF | GFPT2-002 | +++ |
| 46 | NYTNGSFGSNF | DDX5-007 | +++ |
| 47 | RYISPDQLADL | EN01-001 | +++ |
| 48 | YYYGNTLVEF | OLFML2B-002 | +++ |
| 49 | QYLFPSFETF | KLRD-001 | +++ |
| 50 | LYIGWDKHYGF | PSMA4-001 | +++ |
| 51 | NYLLESPHRF | PLE-001 | +++ |
| 52 | SYMEVPTYLNF | LAPTM5-001 | +++ |
| 53 | IYAGQWNDF | COLEC12-001 | +++ |
| 54 | AYKDKDISFF | ZBED5-001 | +++ |
| 55 | IYPVKYTQTF | PERP-001 | +++ |
| 56 | RYFPTQALNF | SLC-003 | +++ |
| 57 | SYSIGIANF | COL12A1-003 | +++ |
| 58 | VYFKPSLTPSGEF | NUP153-001 | +++ |
| 59 | HYFNTPFQL | PPTC-001 | +++ |
| 60 | SYPAKLSFI | FLJ44796-001 | +++ |
| 61 | RYGSPINTF | C6orf132-001 | +++ |
| 62 | AYKPGALTF | AIFM2-001 | +++ |
| 63 | LYINKANIW | G2E-002 | +++ |
| 64 | VYPLALYGF | XPR-001 | +++ |
| 65 | IYQRWKDLL | SAMD9L-001 | +++ |
| 66 | DYIPQLAKF | GLS-001 | +++ |
| 67 | IFLDYEAGHLSF | TRIM11-001 | +++ |
| 68 | RYLFVVDRL | MREG-001 | +++ |
| 69 | TYAALNSKATF | IQGAP1-001 | +++ |
| 70 | VYHSYLTIF | TRPM2-001 | +++ |
| 71 | TYLTNHLRL | ZNF697-001 | +++ |
| 72 | YYVDKLFNTI | RASA2-001 | +++ |
| 73 | RYLHVEGGNF | RBPJ-001 | +++ |
| 74 | EYLPEFLHTF | ABCA13-003 | +++ |
| 75 | AYPDLNEIYRSF | SP14-001 | +++ |
| 76 | VYTZIQSRF | DYR-001 | +++ |
| 77 | RYLEAGAAGLRW | HSPBP-001 | +++ |
| 78 | IYTRVTYYL | TPS-001 | +++ |
| 79 | RYGGSFAEL | KDM6B-001 | ++ |
| 81 | KYIEAIQWI | DCSTA-001 | +++ |
| 82 | FYQGIVQQF | TUBGCP3-001 | +++ |
| 83 | EYSDVLAKLAF | AHD-001 | +++ |
| 84 | TFDVAPSRLDF | NOM-001 | +++ |
| 85 | PFLQASPHF | FAM83A-001 | +++ |
| 159 | TYKYVDINTF | MMP12-004 | +++ |
| 160 | SYLQAANAL | COL6A3-001 | +++ |
| 161 | LYQILQGIVF | CDC2-001 | +++ |

The table lists HLA-A*24 peptides that are very highly over-presented on tumors compared to a panel of normal tissues (+++), highly over-presented on tumors compared to a panel of normal tissues (++) or over-presented on tumors compared to a panel of normal tissues (+).

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Figure 2A:
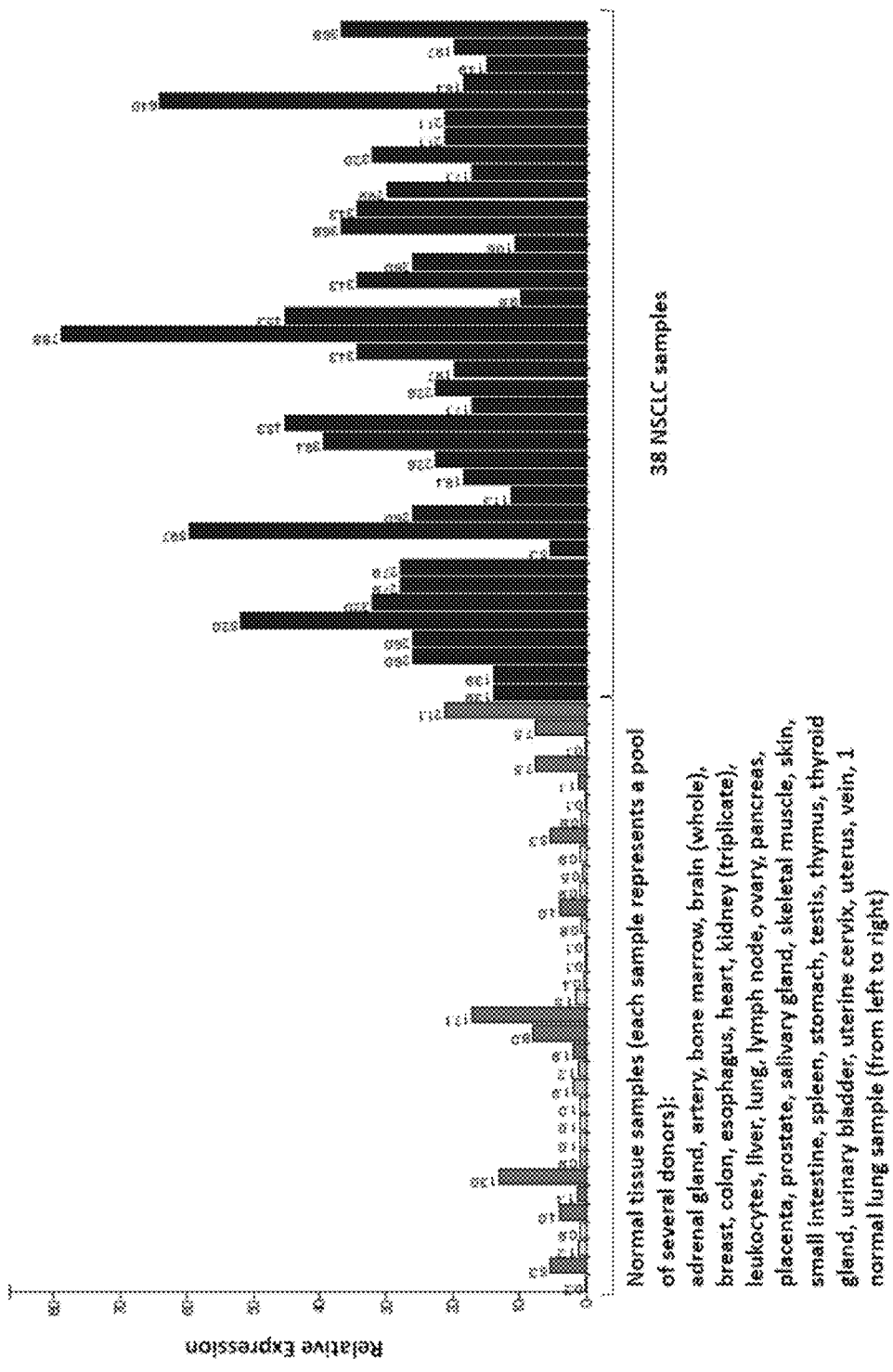
Figure 2B:
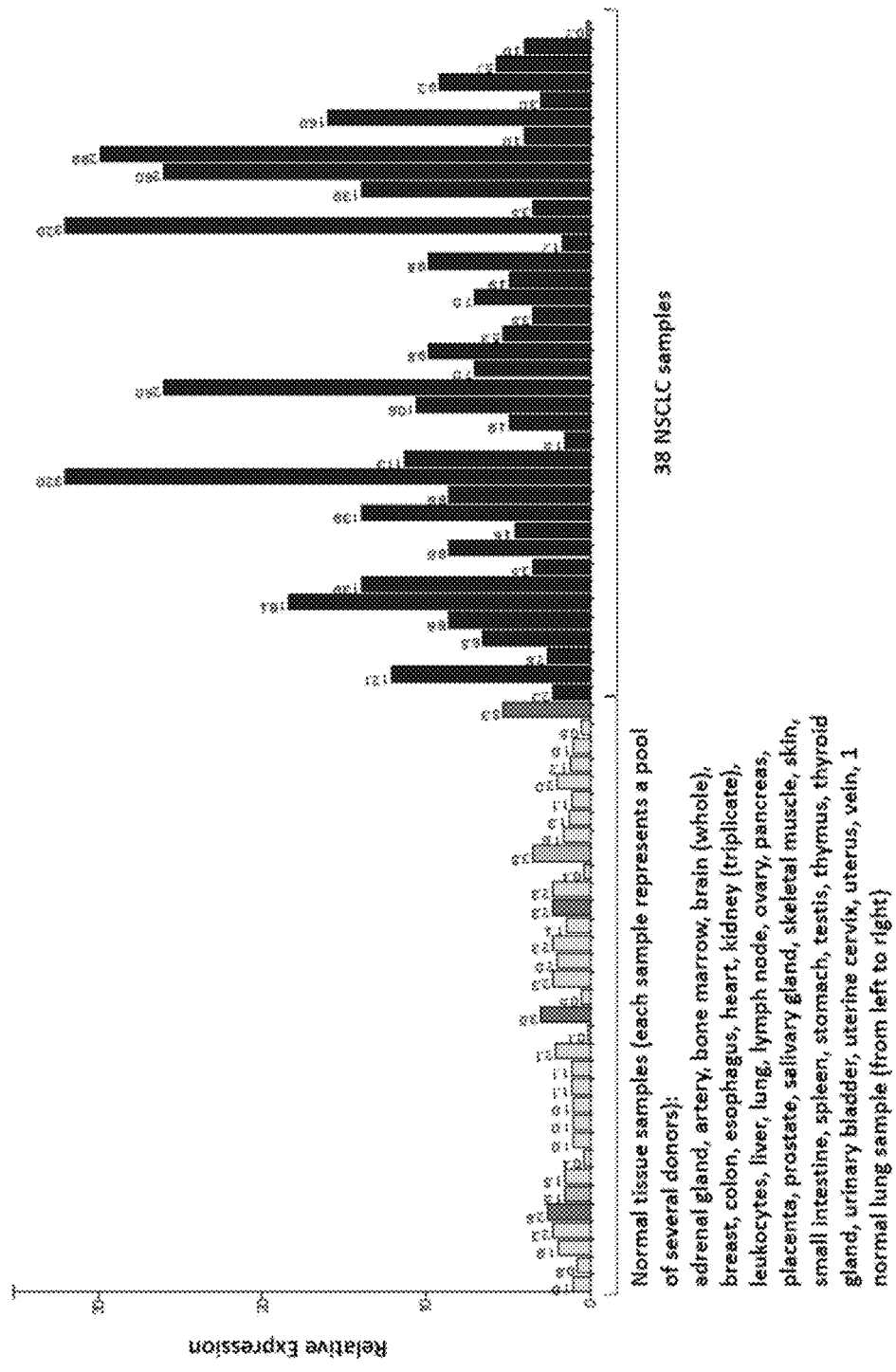
Figure 3A:
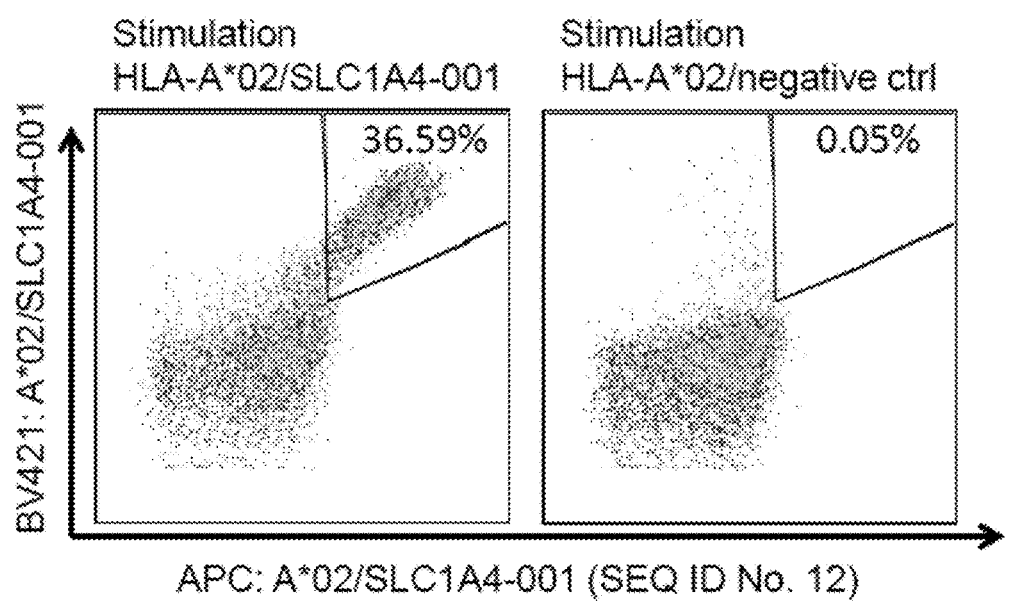
FIGS. 3A-3E show exemplary immunogenicity data: flow cytometry results after peptide-specific multimer staining.
Figure 3B:
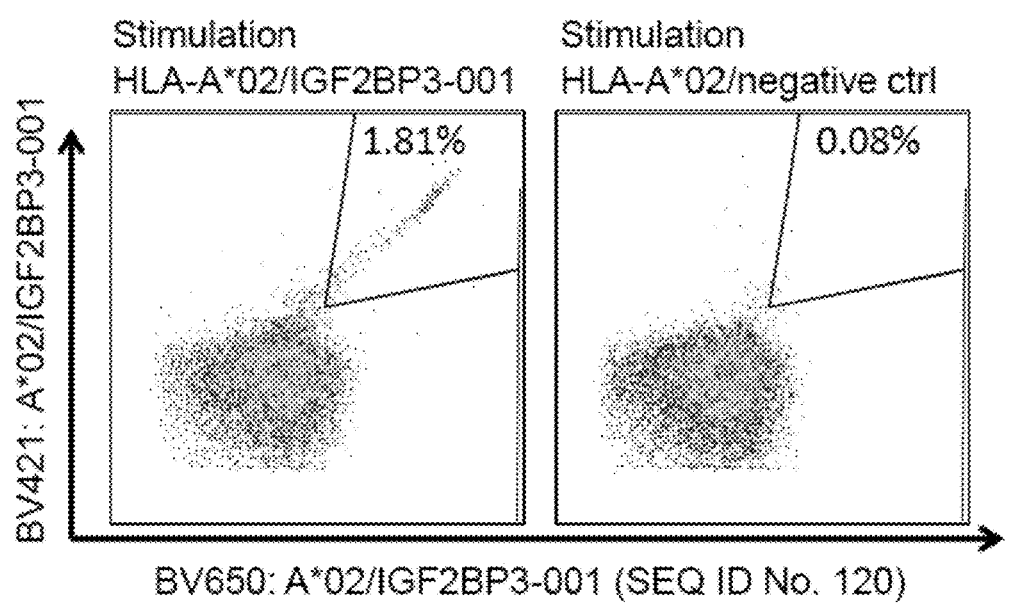
Figure 3C:
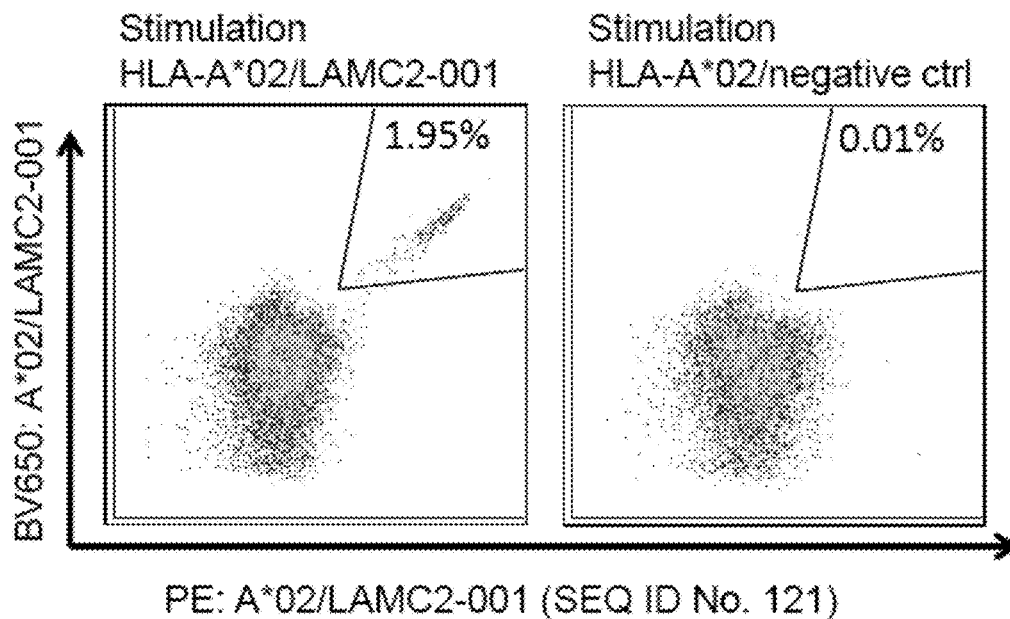
Figure 3D:
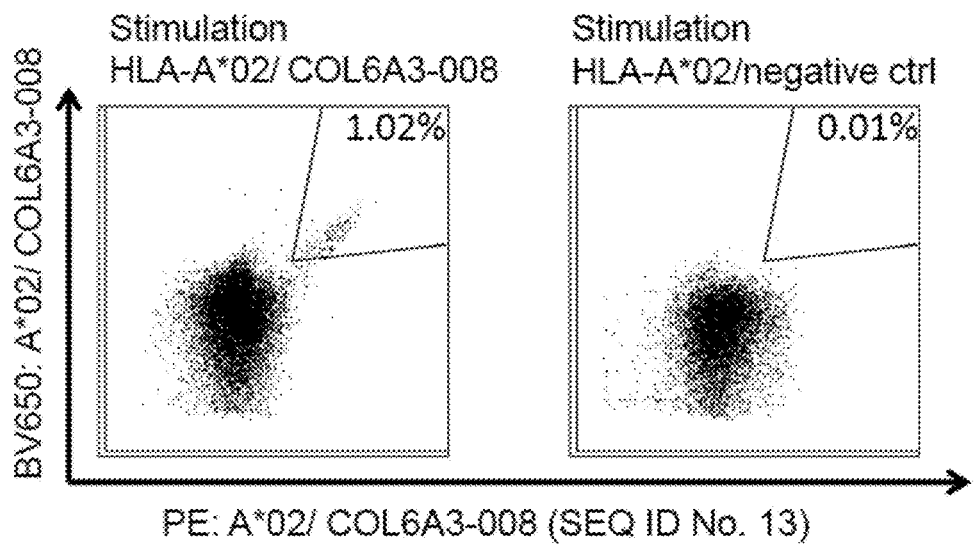
Figure 3:
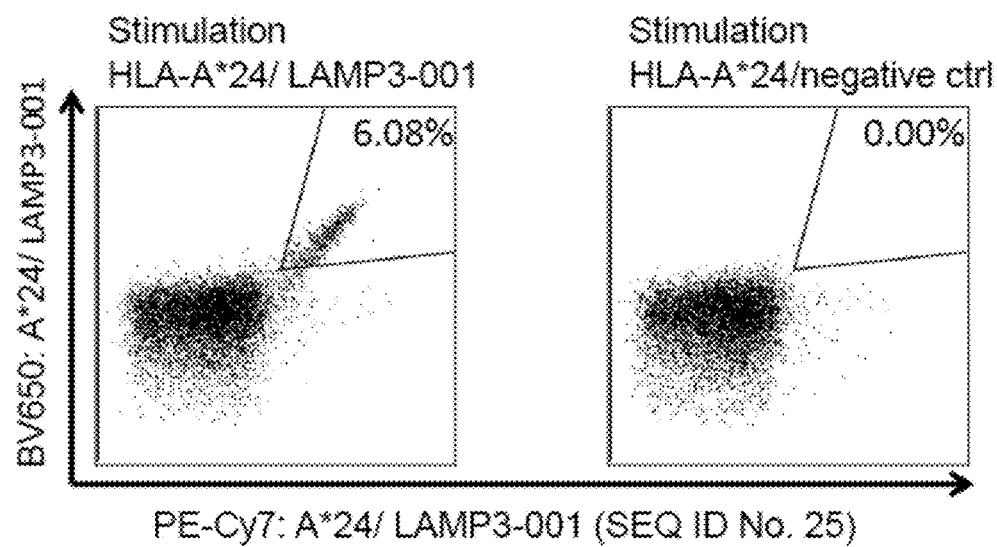

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in lung cancer are shown in FIG. 2. Expression scores for further exemplary genes are shown in Table 17 and Table 18.

TABLE 17

Expression scores.

| SEQ ID No. | Sequence | Peptide Code | Gene Expression |
|---|---|---|---|
| 2 | FLIPYAIML | SLC6A14-001 | ++ |
| 5 | ALTSTLISV | GPNM-002 | + |
| 6 | SLQGSIMTV | SFT-001 | ++ |
| 8 | ALLNILSEV | UBA6-002 | ++ |
| 11 | YLNVQVKEL | SMC4-002 | ++ |
| 12 | IVDRTTTVV | SLC1A4-001 | + |
| 14 | LIQDRVAEV | LAMB3-001 | ++ |
| 16 | LIFDLGGGTFDV | HSP-003 | + |
| 18 | ILLTEQINL | PHT-001 | + |
| 19 | VLTSDSPAL | GPNM-001 | + |
| 95 | KIIGIMEEV | MSH6-001 | ++ |
| 97 | TLFPVRLLV | LPCAT1-001 | + |
| 105 | IVAESLQQV | STA-002 | ++ |
| 106 | SILEHQIQV | MCM4-001 | ++ |
| 108 | TLLDFINAV | UBA6-001 | ++ |
| 115 | YVYQNNIYL | FAP-003 | + |
| 116 | KIQEMQHFL | MMP12-003 | +++ |

TABLE 17-continued

Expression scores.

| SEQ ID No. | Sequence | Peptide Code | Gene Expression |
|---|---|---|---|
| 117 | ILIDWLVQV | CCNB1-002 | + |
| 119 | IVDDITYNV | FN1-001 | + |
| 120 | KIQEILTQV | IGF2BP3-001 | ++ |
| 121 | RLLDSVSRL | LAMC2-001 | ++ |
| 125 | RLDDLKMTV | LAMC2-002 | ++ |
| 130 | KILEDVVGV | TPX2-001 | + |
| 131 | ALVQDLAKA | CCNB1-001 | + |
| 133 | RLASYLDKV | KRT-007 | + |
| 136 | ALVDHTPYL | VCAN-002 | + |
| 140 | TLYPHTSQV | VCAN-001 | + |
| 141 | NLIEKSIYL | DST-001 | + |
| 142 | VLLPVEVATHYL | SLC34A2-001 | ++ |
| 143 | AIVDKVPSV | COPG1-001 | + |
| 144 | KIFDEILVNA | TOP-001 | ++ |
| 152 | ILQDRLNQV | CDC6-001 | + |
| 158 | KLDETNNTL | DST-002 | + |

The table lists HLA-A*02 peptides from genes that are very highly over-expressed in tumors compared to a panel of normal tissues (+++), highly over-expressed in tumors compared to a panel of normal tissues (++) or over-expressed in tumors compared to a panel of normal tissues (+).

TABLE 18

Expression scores.

| SEQ ID No. | Sequence | Peptide Code | Gene Expression |
|---|---|---|---|
| 23 | VYTSWQIPQKF | CCL18-001 | +++ |
| 24 | NYPKSIHSF | MMP12-005 | +++ |
| 25 | RFMDGHITF | LAMP3-001 | +++ |
| 26 | RYLEKFYGL | MMP12-006 | +++ |
| 28 | RYLDSLKAIVF | CENPN-001 | ++ |
| 29 | YYTKGFALLNF | PLOD2-002 | + |
| 30 | KYLEKYYNL | MMP1-001 | + |
| 31 | SYLDKVRAL | KRT-008 | + |
| 34 | VFMKDGFFYF | MMP1-002 | + |
| 35 | TYNPEIYVI | ITGA2-002 | + |
| 38 | VFLNRAKAVFF | GPNM-003 | + |
| 39 | KFLEHTNFEF | DOCK2-001 | + |
| 43 | RYTLHINTL | ALOX15B-001 | + |
| 47 | RYISPDQLADL | ENO1-001 | + |
| 159 | TYKYVDINTF | MMP12-004 | +++ |
| 161 | LYQILQGIVF | CDC2-001 | + |

The table lists HLA-A*24 peptides from genes that are very highly over-expressed in tumors compared to a panel of normal tissues (+++), highly over-expressed in tumors compared to a panel of normal tissues (++) or over-expressed in tumors compared to a panel of normal tissues (+).

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 84 HLA-A*02 restricted TUMAPs of the invention so far, demonstrating that these peptides are T-cell epitopes against which CD8+ precursor T cells exist in humans (Table 19).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 163) from modified Melan-A/MART-1) and A*0201/DDX5-001 (YLLPAIVHI from DDX5, SEQ ID NO. 164), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Lung Cancer Peptides

For tested HLA class I peptides, in vitro immunogenicity could be demonstrated by generation of peptide specific T-cell lines. Exemplary flow cytometry results after TUMAP-specific multimer staining for 3 peptides of the invention are shown in FIGS. 3A-3E together with corresponding negative controls. Results for 84 peptides from the invention are summarized in Table 19.

TABLE 19 in vitro immunogenicity of HLA-A*02 peptides of the invention
Exemplary results of in vitro immunogenicity experiments
conducted by the applicant for the peptides of the invention.

| Seq ID | Peptide code | wells | donors |
|---|---|---|---|
| 1 | COL6A3-010 | ++ | ++++ |
| 2 | SLC6A14-001 | + | ++++ |
| 3 | COL6A3-007 | + | ++++ |
| 4 | DUSP4-001 | ++ | ++++ |
| 5 | GPNM-002 | + | ++++ |
| 6 | SFT-001 | ++ | ++++ |
| 7 | KRT80-001 | + | ++ |
| 8 | UBA6-002 | ++ | ++++ |
| 9 | MCM5-001 | + | ++++ |
| 10 | KRT15-001 | ++++ | ++++ |
| 11 | SMC4-002 | + | ++++ |
| 12 | SLC1A4-001 | ++++ | ++++ |
| 13 | COL6A3-008 | + | ++ |
| 14 | LAMB3-001 | + | ++++ |
| 15 | 5F3B3-001 | ++ | ++++ |
| 16 | HSP-003 | + | +++ |
| 17 | KRT-006 | + | ++ |
| 18 | PHT-001 | + | ++ |
| 19 | GPNM-001 | + | ++++ |
| 21 | CSNK2A2-001 | + | + |
| 22 | PTPN13-001 | + | + |
| 94 | CCNB2-001 | ++ | ++++ |
| 95 | MSH6-001 | ++++ | ++++ |
| 96 | PRPF3-001 | ++++ | ++++ |
| 97 | LPCAT1-001 | +++ | ++++ |
| 98 | DONSON-001 | + | ++++ |
| 99 | DKC-001 | ++ | ++++ |
| 100 | BUB1B-001 | ++ | ++++ |
| 101 | ERO-001 | + | +++ |
| 102 | GBPS-001 | + | ++ |
| 103 | TMEM43-001 | + | ++++ |
| 104 | COG4-001 | + | ++++ |
| 105 | STA-002 | + | + |
| 106 | MCM4-001 | + | + |
| 107 | PSMD14-002 | + | +++ |
| 108 | UBA6-001 | + | +++ |
| 109 | CCZ-001 | + | +++ |
| 111 | RAD54B-001 | ++ | ++++ |
| 112 | FZD-001 | +++ | ++++ |
| 113 | COL6A3-002 | ++ | ++++ |
| 114 | WNT5A-001 | ++ | ++++ |
| 115 | FAP-003 | + | ++++ |
| 116 | MMP12-003 | + | ++++ |
| 117 | CCNB1-002 | ++ | ++++ |
| 118 | ATP-001 | ++++ | ++++ |
| 119 | FN1-001 | ++ | ++++ |
| 120 | IGF2BP3-001 | + | ++++ |
| 121 | LAMC2-001 | ++ | ++++ |
| 122 | CERC-001 | +++ | ++++ |
| 123 | MXRA5-002 | + | ++++ |
| 124 | COL6A3-003 | + | ++++ |
| 125 | LAMC2-002 | + | ++++ |
| 126 | ADAM8-001 | + | ++++ |
| 127 | MAGEF1-001 | +++ | ++++ |
| 128 | MXRA5-001 | + | ++++ |
| 129 | SNRNP20-001 | ++ | ++++ |
| 130 | TPX2-001 | ++ | ++++ |
| 131 | CCNB1-001 | ++ | ++++ |
| 132 | TGFBI-001 | ++ | ++++ |
| 133 | KRT-007 | ++ | ++++ |
| 134 | CDK4-001 | ++++ | ++++ |
| 135 | GFPT2-001 | +++ | ++++ |
| 136 | VCAN-002 | + | ++++ |
| 137 | COL12A1-002 | + | ++ |
| 138 | UBE2S-001 | + | ++++ |
| 139 | SMYD3-001 | + | ++ |
| 140 | VCAN-001 | ++ | ++++ |
| 141 | DST-001 | + | ++++ |
| 142 | 5LC34A2-001 | + | ++ |

TABLE 19-continued in vitro immunogenicity of HLA-A*02 peptides of the invention
Exemplary results of in vitro immunogenicity experiments
conducted by the applicant for the peptides of the invention.

| Seq ID | Peptide code | wells | donors |
|---|---|---|---|
| 143 | COPG1-001 | + | +++ |
| 144 | TOP-001 | + | ++ |
| 145 | TNC-001 | + | ++ |
| 147 | BNC1-001 | + | ++++ |
| 148 | PLT-001 | + | ++ |
| 149 | TACC3-001 | + | +++ |
| 150 | PCNXL3-001 | + | +++ |
| 151 | DROSHA-001 | + | ++++ |
| 152 | CDC6-001 | + | +++ |
| 153 | DIO2-001 | + | + |
| 154 | ABCA13-001 | + | ++++ |
| 155 | ABCA13-002 | + | +++ |
| 156 | KIF26B-001 | + | + |
| 157 | SERPINB3-001 | + | +++ |
| 158 | DST-002 | + | ++ |

<20% = +;
20%-49% = ++;
50%-69% = +++;
>=70% = ++++

TABLE 20 in vitro immunogenicity of HLA-A*24 peptides of the invention
Exemplary results of in vitro immunogenicity experiments conducted by
the applicant for the peptides of the invention.

| Seq ID | Peptide code | wells | donors |
|---|---|---|---|
| 23 | CCL18-001 | + | + |
| 25 | LAMP3-001 | + | ++ |
| 26 | MMP12-006 | + | ++++ |
| 27 | COL6A3-012 | ++ | ++++ |
| 28 | CENPN-001 | + | ++++ |
| 29 | PLOD2-002 | + | +++ |
| 30 | MMP1-001 | ++ | ++++ |
| 32 | COL6A3-013 | + | + |
| 33 | MUC16-001 | + | ++ |
| 34 | MMP1-002 | + | ++ |
| 35 | ITGA2-002 | ++ | ++++ |
| 36 | OLFML2B-001 | ++ | ++++ |
| 37 | TTC13-001 | +++ | ++++ |
| 39 | DOCK2-001 | + | ++ |
| 40 | PVRL1-001 | + | ++ |
| 41 | FKBP10-002 | + | ++++ |
| 42 | ABCC1-001 | + | ++ |
| 43 | ALOX15B-001 | + | ++ |
| 44 | SMPDL3B-001 | ++ | ++++ |
| 46 | DDX5-007 | + | + |
| 47 | ENO1-001 | + | +++ |
| 48 | OLFML2B-002 | + | ++ |
| 49 | KLRD-001 | + | ++++ |
| 50 | PSMA4-001 | + | ++++ |
| 52 | LAPTM5-001 | + | ++ |
| 53 | COLEC12-001 | + | +++ |
| 54 | ZBED5-001 | + | ++++ |
| 56 | SLC-003 | + | + |
| 57 | COL12A1-003 | + | ++++ |
| 58 | NUP153-001 | + | + |
| 59 | PPTC-001 | ++ | ++++ |
| 61 | C6orf132-001 | + | +++ |
| 62 | AIFM2-001 | + | ++ |
| 63 | G2E-002 | + | ++ |
| 64 | XPR-001 | ++ | ++++ |
| 65 | SAMD9L-001 | + | +++ |
| 66 | GLS-001 | + | ++++ |
| 67 | TRIM11-001 | + | + |
| 68 | MREG-001 | ++++ | ++++ |
| 69 | IQGAP1-001 | + | + |
| 70 | TRPM2-001 | ++ | ++++ |
| 71 | ZNF697-001 | ++ | ++++ |
| 72 | RASA2-001 | + | ++ |
| 73 | RBPJ-001 | + | ++ |
| 74 | ABCA13-003 | + | ++ |
| 75 | SP14-001 | + | + |
| 76 | DYR-001 | + | ++ |
| 77 | HSPBP-001 | + | + |
| 78 | TPS-001 | ++ | ++++ |
| 79 | KDM6B-001 | + | ++ |
| 81 | DCSTA-001 | ++ | ++++ |
| 82 | TUBGCP3-001 | + | ++ |
| 83 | AHD-001 | + | +++ |
| 85 | FAM83A-001 | ++ | ++++ |
| 159 | MMP12-004 | + | +++ |
| 160 | COL6A3-001 | + | ++ |
| 161 | CDC2-001 | + | ++++ |

<20% = +;
20%-49% = ++;
50%-69% = +++;
>=70% = ++++

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >85%. All TUMAPs are preferably administered as trifluoro-acetate salts or acetate salts, other pharmaceutically acceptable salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (62m) of stabilized MHC complexes. The assay was performed as generally described in Rodenko et al (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-62m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 21

MHC class I binding scores

| Seq. ID | Peptide code | Peptide exchange |
|---|---|---|
| 31 | KRT-008 | +++ |
| 45 | GFPT2-002 | +++ |
| 51 | PLE-001 | +++ |
| 55 | PERP-001 | +++ |
| 60 | FLJ44796-001 | +++ |
| 80 | FXR1-001 | +++ |

<20% = +;
20%-49% = ++;
50%-75% = +++;
>=75% = ++++

Example 6

Absolute Quantitation of Tumor Associated Peptides Presented on the Cell Surface The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. In addition to the isolation and relative quantitation of peptides as described in example 1, the inventors did analyze absolute peptide copies per cell. The quantitation of TUMAP copies per cell in solid tumor samples requires the absolute quantitation of the isolated TUMAP, the efficiency of TUMAP isolation, and the cell count of the tissue sample analyzed. Experimental steps are described below.

Peptide Quantitation by Nano LC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments. The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression. For the quantitation of tumor-associated peptides from tissue samples, the respective samples were also spiked with the internal standard, the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs. The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Forsey and Chaudhuri, 2009; Alcoser et al., 2011; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates. In order to calculate the cell number, a DNA standard curve from aliquots of single healthy blood cells, with a range of defined cell numbers, was generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell numbers for selected peptides are shown in Table 22.

TABLE 22

Absolute copy numbers. The table lists the results of absolute peptide quantitation in NSCLC tumor samples.

| SEQ ID No. | Peptide Code | Copies per cell (median) | Number of samples |
|---|---|---|---|
| 13 | COL6A3-008 | +++ | 18 |
| 23 | CCL18-001 | +++ | 19 |
| 24 | MMP12-005 | +++ | 11 |
| 25 | LAMP3-001 | ++++ | 7 |
| 26 | MMP12-006 | +++ | 17 |
| 27 | COL6A3-012 | +++ | 12 |
| 29 | PLOD2-002 | ++ | 22 |
| 30 | MMP1-001 | +++ | 11 |
| 32 | COL6A3-013 | ++ | 20 |
| 33 | MUC16-001 | ++ | 22 |

TABLE 22-continued

Absolute copy numbers. The table lists the results of absolute peptide quantitation in NSCLC tumor samples.

| SEQ ID No. | Peptide Code | Copies per cell (median) | Number of samples |
|---|---|---|---|
| 35 | ITGA2-002 | ++ | 19 |
| 36 | OLFML2B-001 | +++ | 22 |
| 37 | TTC13-001 | +++ | 13 |
| 38 | GPNM-003 | +++ | 5 |
| 41 | FKBP10-002 | ++ | 19 |
| 98 | DONSON-001 | + | 18 |
| 100 | BUB1B-001 | + | 11 |
| 111 | RAD54B-001 | + | 16 |
| 113 | COL6A3-002 | ++ | 19 |
| 114 | WNT5A-001 | ++ | 17 |
| 115 | FAP-003 | ++ | 17 |
| 120 | IGF2BP3-001 | ++ | 14 |
| 121 | LAMC2-001 | ++ | 10 |
| 123 | MXRA5-002 | + | 17 |
| 124 | COL6A3-003 | +++ | 18 |
| 126 | ADAM8-001 | + | 15 |
| 128 | MXRA5-001 | ++ | 19 |
| 137 | COL12A1-002 | ++ | 12 |
| 140 | VCAN-001 | + | 19 |
| 141 | DST-001 | ++ | 12 |
| 147 | BNC1-001 | + | 10 |
| 158 | DST-002 | ++ | 7 |
| 159 | MMP12-004 | ++ | 22 |
| 160 | COL6A3-001 | ++++ | 23 |
| 161 | CDC2-001 | +++ | 18 |

The median numbers of copies per cell are indicated for each peptide: <100 = +; >=100 = ++; >=1,000 +++; >=10,000 = ++++.
The number of samples, in which evaluable, high quality MS data are available is indicated.

Example 6

HLA Class II T-Cell Proliferation Assays

The experiments as follows summarize the results of T-cell Proliferation Assays of selected MHC class II TUMAPs. Nine of 10 tested peptide antigens tested positive for immunogenicity. Eleven out of 21 evaluable T-cell samples showed a positive response for at least one peptide. Individual peptide antigens stimulated the CD4+ T-cell proliferation in up to 6 donors. These numbers are comparable to the results for five reference peptides tested in the same assay runs and with immunogenicity demonstrated for the majority of patients in clinical vaccine trial settings. Thus, it can be concluded that the newly tested peptides also have a high potential to induce T-cell responses in vaccine trials.

In order to characterize selected peptides for their potential especially as vaccine candidates, their in vitro immunogenicity was determined by analysis of T-cell proliferation using a commercial T-cell Proliferation Assay from the company ProImmune.

Healthy donor CD8-depleted blood cells samples were tested with the selected peptides. The peptides that induce the proliferation of CD4+ T cells can potentially result in the development of a helper T-cell immune response, and therefore are considered to be immunogenic. The proliferation of CD4+ T cells was determined using carboxyfluorescein succinimidyl ester (CFSE) labelling. In proliferating cells, CFSE is distributed evenly to dividing cells. Thus, the proliferation can be measured as a decrease in CFSE fluorescence in the cells as analyzed.

TABLE 23

Selected HLA class II peptides.

| Sequence ID NO: | Peptide ID | Sequence | Origin |
|---|---|---|---|
| 86 | MMP12-007 | LSADDIRGIQSLYGDPK | This app. |
| 87 | COL11A1-001 | EGDIQQFLITGDPKAAYDY | This app. |
| 92 | COL1A2-001 | NKPSRLPFLDIAPLDIGGAD | This app. |
| 91 | COL5A2-001 | VARLPIIDLAPVDVGGTD | This app. |
| 93 | FN1-002 | SRPQAPITGYRIVYSPSV | This app. |
| 88 | ITGB6-001 | NPVSQVEILKNKPLSVG | This app. |
| 90 | LAMC2-003 | DAVQMVITEAQKVDTR | This app. |
| 110 | LAMP3-002 | IQLIVQDKESVFSPR | This app. |
| 89 | IGF2BP3-002 | KLYIGNLSENAAPS | This app. |
| 162 | POSTN-002 | TNGVIHVVDKLLYPADT | This app. |
| 165 | BIR-002 | TLGEFLKLDRERAKN | Pos. contr. |
| 166 | MET-005 | TFSYVDPVITSISPKYG | Pos. contr. |
| 167 | MMP-001 | SQDDIKGIQKLYGKRS | Pos. contr. |
| 168 | CEA-006 | SPQYSWRINGIPQQHT | Pos. contr. |
| 169 | TGFBI-004 | TPPIDAHTRNLLRNH | Pos. contr. |

Principle of Test

Peripheral blood mononuclear cell (PBMC) samples from healthy human donors were selected from the ProImmune cell bank based on HLA-DRB1 allele expression. CD8+ T-cells were depleted from donor blood samples prior to use to avoid a false-positive response. The remaining CD4+ T cells were labelled with CFSE and subsequently incubated with 5 µM of each selected peptide. Each peptide was tested in six replicated wells. The background was measured on each plate in six unstimulated control wells.

After an incubation period of 7 days the cells were co-stained with anti-CD4 antibody and analyzed by flow cytometry. The degree of proliferation was determined by measuring a reduction in CFSE intensity.

The evaluation of flow cytometric data was performed using FlowJo Software (Tree Star, Inc.). The results of flow cytometric analysis were expressed as the ratio of the CD4+ dim population to the total CD4+ population. The degree of proliferation was expressed as percentage of stimulation above background, i.e. proportion of antigen stimulated CD4+ CFSE dim cells minus the proportion of CD4+ CFSE dim cells from unstimulated control wells. For each sample, a mean and the corresponding standard error of the mean (SEM) of the six replicates were calculated.

Selection of Donors

Donors were chosen by HLA-DRB1 allele expression. The other two HLA class II loci (DQ and DP) have not been included into the analysis. The interesting DRB1 alleles were selected according to the frequencies of predicted peptide binding based on SYFPEITHI algorithm (Rammensee et al., 1999). For HLA-DR, binding was defined by a SYFPEITHI binding prediction score equal or greater than 18. This threshold score for binding was defined based on the analysis of binding scores of known published promiscuous HLA-DR ligands (Table 24).

Table 24: SYFPEITHI prediction scores for HLA-DR binding of peptides that have been shown experimentally to bind to several HLA-DR alleles. Prediction scores are only shown, if binding to the indicated DR allele has been shown experimentally. If high resolution information of DR alleles is not available this is marked by*. 23 of 26 (89%) SYFPEITHI scores are >=18, if the binding was experimentally shown for an allele.

| Peptide | DRB1* allele | | | | | |
|---|---|---|---|---|---|---|
| | 0101 | 0301 | 0401 | 0701 | 1101 | 1501 |
| SSX2₄₅₋₅₉ KIFYVYMKRKYEAMT SEQ ID NO: 170 | — | — | — | 18 | 24 | — |
| MAGE A3₁₁₁₋₁₂₅ RKVAELVHFLLLKYR SEQ ID NO: 171 | 24* | — | 26* | — | 23* | — |
| MAGE A3₁₄₆₋₁₆₀ FFPVIFSKASSSLQL SEQ ID NO: 172 | 31* | — | 28* | 24* | 24* | — |
| MAGE A3₁₉₁₋₂₀₅ GDNQIMPKAGLLIV SEQ ID NO: 173 | 24* | — | 20* | — | 14* | — |
| MAGE A3₂₈₁₋₃₉₅ TSYVKVLHHMVKISG SEQ ID NO: 174 | 27* | — | 28* | — | 28* | — |
| NY-ESO-1₁₂₁₋₁₃₈ VLLKEFTVSGNILTIRLT SEQ ID NO: 175 | 22 | — | — | 24 | 14 | — |
| HER2/neu₈₈₃₋₈₉₉ KVPIKWMALESILRRRF SEQ ID NO: 176 | 25 | — | 22 | — | — | — |
| PADRE [D-Ala]K[L-cyclohexyl-Ala] VAAWTLKAA[D-Ala] SEQ ID NO: 177 | 26 | 11 | 28 | 28 | 17 | 24 |

All DRB1 alleles with binding frequency over 20% over all selected peptides were requested to be included into the donor panel) by ProImmune. 4 other rare DRB1 alleles (DRB1*10:01, DRB1*16:01, DRB1*08:01, and DRB1*13:03) were requested additionally. The assembled donor panel is shown in Table 26.

TABLE 25

Binding capacity of selected peptides to various HLA-DRB1 alleles with known binding motif: A SYFPEITHI score over 17 was counted with 1 as a binding event. The last column shows the percentage of binding events over all selected peptides.

| MHC | MMP12-007 | COL11A1-001 | COL1A2-001 | COL5A2-001 | FN1-002 | ITGB6-001 | LAMC2-003 | LAMP3-002 |
|---|---|---|---|---|---|---|---|---|
| DRB1*0401 | 1 | 1 | 1 | 1 | 1 | 1 | 1 | 1 |
| DRB1*0404 | 1 | 1 | 1 | 1 | 1 | 1 | 1 | 1 |
| DRB1*0101 | 1 | 1 | 1 | 1 | 1 | 1 | 1 | 1 |
| DRB1*0301 | 1 | 1 | 1 | 1 | 0 | 1 | 1 | 1 |
| DRB1*1104 | 1 | 1 | 1 | 1 | 1 | 1 | 1 | 1 |
| DRB1*0405 | 1 | 1 | 1 | 1 | 1 | 1 | 1 | 1 |
| DRB1*0402 | 1 | 1 | 1 | 1 | 0 | 1 | 1 | 1 |
| DRB1*0701 | 1 | 1 | 1 | 1 | 1 | 1 | 1 | 1 |
| DRB1*1501 | 1 | 1 | 1 | 1 | 1 | 1 | 1 | 1 |
| DRB1*1301 | 0 | 1 | 1 | 1 | 1 | 0 | 1 | 0 |
| DRB1*1502 | 1 | 1 | 1 | 1 | 1 | 1 | 0 | 0 |
| DRB1*1101 | 1 | 0 | 1 | 0 | 0 | 1 | 0 | 0 |
| DRB1*0901 | 0 | 0 | 0 | 1 | 1 | 1 | 0 | 0 |
| DRB1*1302 | 0 | 1 | 0 | 0 | 0 | 0 | 0 | 0 |
| DRB1*0802 | 0 | 1 | 0 | 0 | 0 | 0 | 0 | 0 |
| DRB1*0803 | 0 | 0 | 0 | 0 | 0 | 0 | 0 | 0 |

| MHC | IGF2BP3-002 | POSTN-002 | BIR-002 | MET-005 | MMP-001 | CEA-006 | TGFBI-004 | % of Peptide binders |
|---|---|---|---|---|---|---|---|---|
| DRB1*0401 | 1 | 1 | 1 | 1 | 1 | 1 | 1 | 100% |
| DRB1*0404 | 1 | 1 | 1 | 1 | 1 | 1 | 1 | 100% |
| DRB1*0101 | 1 | 1 | 1 | 1 | 1 | 1 | 0 | 93% |
| DRB1*0301 | 1 | 1 | 1 | 1 | 1 | 1 | 1 | 93% |
| DRB1*1104 | 1 | 1 | 1 | 1 | 1 | 0 | 1 | 93% |
| DRB1*0405 | 1 | 1 | 1 | 1 | 1 | 1 | 0 | 93% |
| DRB1*0402 | 1 | 1 | 1 | 1 | 1 | 1 | 0 | 87% |
| DRB1*0701 | 1 | 1 | 0 | 1 | 0 | 0 | 1 | 80% |
| DRB1*1501 | 0 | 0 | 1 | 1 | 1 | 0 | 0 | 73% |
| DRB1*1301 | 1 | 1 | 1 | 1 | 1 | 0 | 0 | 67% |
| DRB1*1502 | 1 | 0 | 1 | 1 | 1 | 0 | 0 | 67% |
| DRB1*1101 | 1 | 1 | 1 | 1 | 1 | 0 | 0 | 53% |
| DRB1*0901 | 0 | 1 | 0 | 1 | 0 | 1 | 0 | 40% |
| DRB1*1302 | 0 | 1 | 1 | 0 | 0 | 0 | 0 | 20% |
| DRB1*0802 | 0 | 1 | 1 | 0 | 0 | 0 | 0 | 20% |
| DRB1*0803 | 0 | 1 | 1 | 0 | 0 | 0 | 0 | 13% |

TABLE 26

Donor panel. HLA-DRB1 allele distribution of 21 selected donors

| Donor ID | DRB1_1 | DRB1_2 |
|---|---|---|
| D778 | *04:04 | *1001 |
| D780 | *01:01 | *04:01 |
| D789 | *13:01 | *16:01 |
| D799 | *03:01 | *09:01 |
| D800 | *15:02 | *16:01 |
| D801 | *11:01 | *15:01 |
| D813 | *07:01 | *15:01 |
| D816 | *01:01 | *04:05 |
| D817 | *10:01 | *13:01 |
| D820 | *01:01 | *07:01 |
| D822 | *04:04 | *08:01 |
| D829 | *07:01 | *11:01 |
| D836 | *13:01 | *13:03 |
| D845 | *03:01 | *11:04 |
| D857 | *03:01 | *04:05 |
| D906 | *15:01 | *15:02 |
| D940 | *04:01 | *15:01 |
| D946 | *11:01 | *14:01 |
| D951 | *03:01 | *04:04 |
| D962 | *03:01 | *09:01 |
| D973 | *03:01 | *11:04 |

Results of In Vitro Immunogenicity

The antigen-stimulated proliferation of CD4+ T cells was considered as an indicator of in vitro immunogenicity and was investigated in a commercially available T-cell Proliferation Assay from ProImmune. The degree of antigen-stimulated CD4+ T-cell proliferation was expressed as a percentage of stimulation above background. A response over 0.02% stimulation above background with SEM=2 (i.e. values two standard errors greater than background) was considered to be positive.

Figure 4:
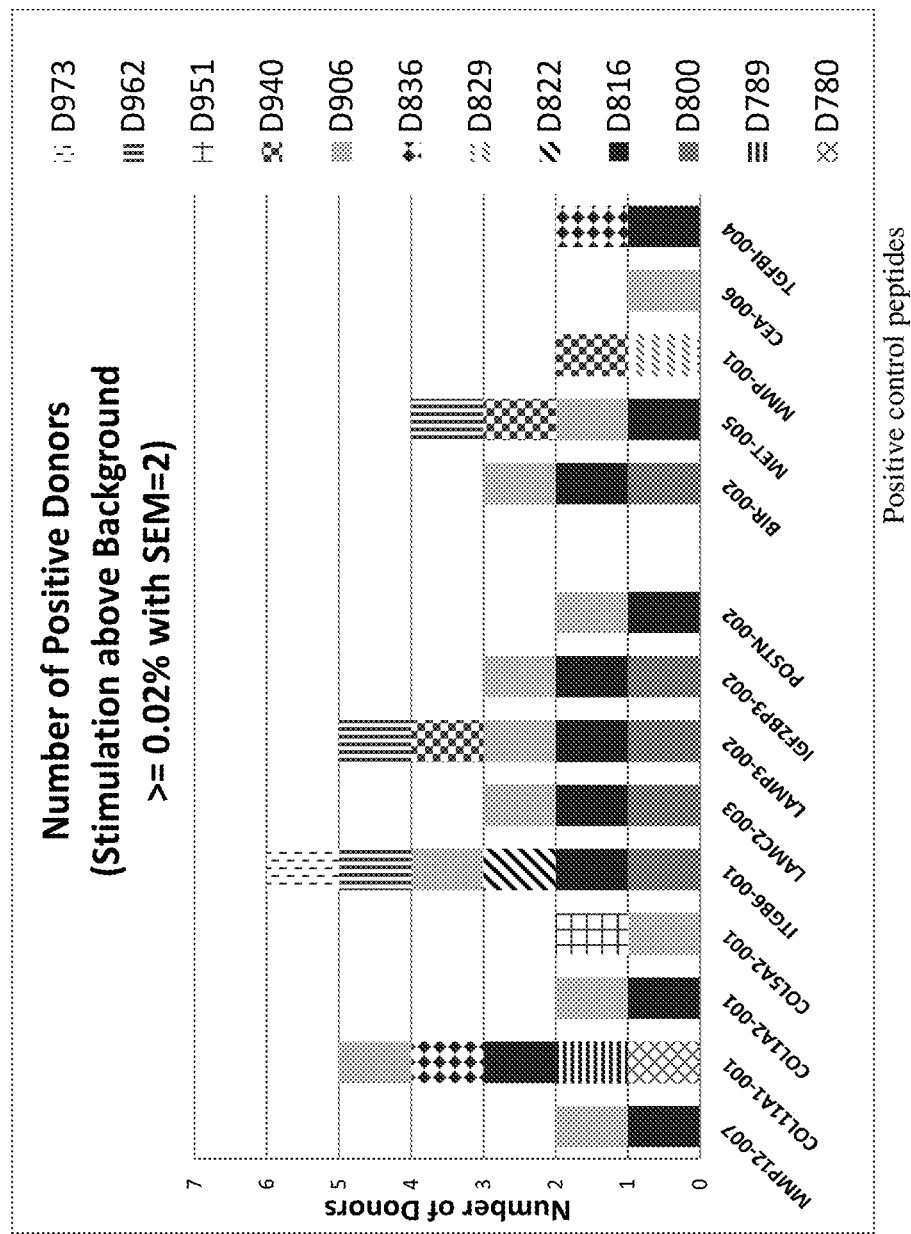
FIG. 4 shows the results of antigen stimulated CD4+ T-cell proliferation: The figure shows the number of positive donors for each peptide.

Nine of 10 selected peptide antigens (with the exception of FN1-002) were tested positive. Eleven out of 21 evaluable T-cell samples showed a positive response for at least one peptide (FIG. 4). Individual peptide antigens stimulated the CD4+ T-cell proliferation in up to 6 donors.

Comparison of In Vivo to In Vitro Immunogenicity

The T-cell proliferation analysis included 5 peptides with known in vivo immunogenicity as positive controls. The in vivo immunogenicity of these peptides was determined in blood samples of patients vaccinated with these peptides in clinical trials using intracellular cytokine staining (ICS) of CD4 T cells.

Figure 5:
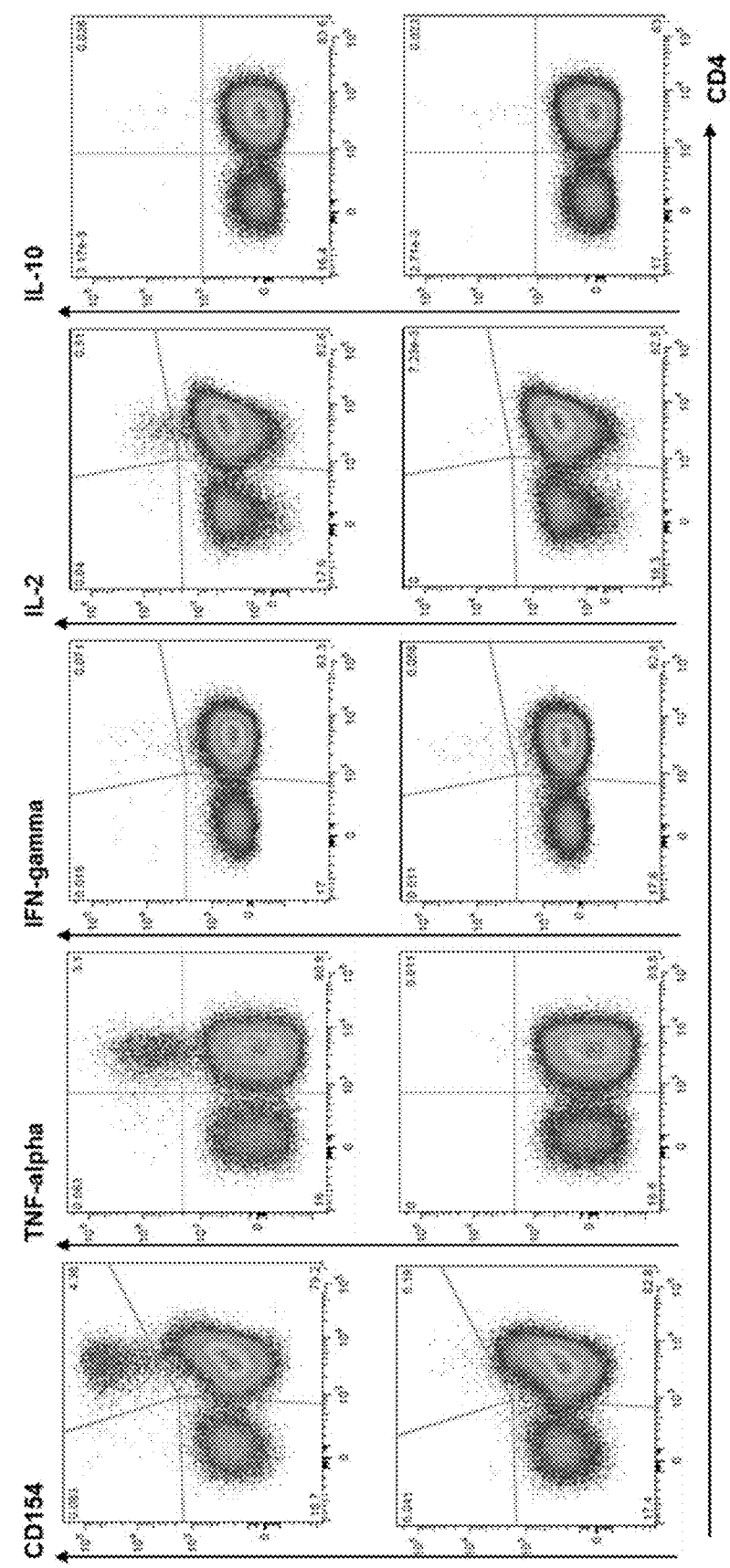
FIG. 5 shows exemplary vaccine-induced CD4 T-cell response to CEA-006 in class II ICS assay. Following in vitro sensitization PBMCs of patient 36-031 were analyzed for CD4 T-cell responses to CEA-006 (upper panel) and mock (lower panel) at time point pool V8/EOS. Cells were stimulated with corresponding peptides and stained with viability, anti-CD3, anti-CD8, anti-CD4 and effector markers (from right to left: CD154, TNF-alpha, IFN-gamma, IL-2, IL-10), respectively. Viable CD4 T-cells were analyzed for the proportion of cells positive for one or more effector molecules.

In principle, ICS assays analyze the quality of specific T cells in terms of effector functions. Therefore the peripheral mononuclear cells (PBMCs) were re-stimulated in vitro with the peptide of interest, a reference peptide and a negative control (here MOCK). Following the re-stimulated cells were stained for IFN-gamma, TNF-alpha, IL-2 and IL-10 production, as well as expression of the co-stimulatory molecule CD154. The counting of stained cells was performed on a flow cytometer (FIG. 5).

Figure 6:
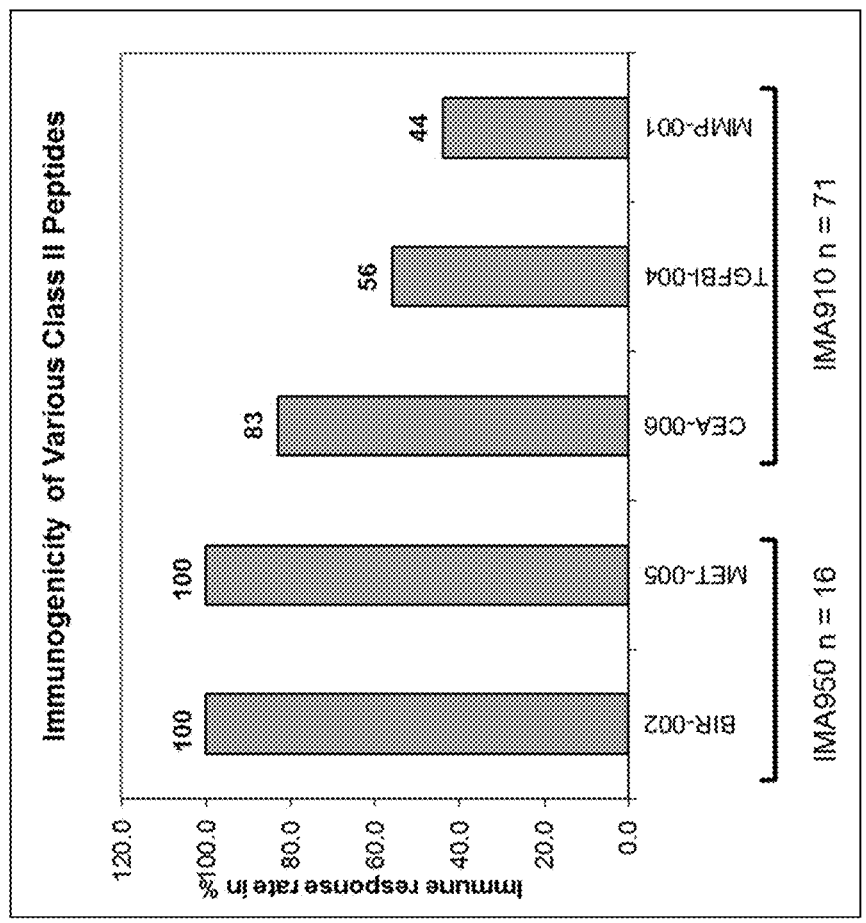
FIG. 6 shows the immunogenicity of control class II peptides: The diagram shows the immune response rate to 5 class II peptides detected in 16 patients for IMA950 peptides and in 71 patients for IMA910 peptides using ICS.

The immunogenicity analysis revealed 100% immune response by vaccination with IMA950 peptides (BIR-002 and MET-005) in 16 patients (study IMA950-101) and 44% to 86% immune response by vaccination with IMA910 peptides (CEA-006, TGFBI-004 and MMP-001) in 71 patients (study IMA910-101) (FIG. 6).

The results of in vitro immunogenicity of peptides with known in vivo immunogenicity were compared to the selected peptides (Table 27). The analysis showed that the positive control peptides stimulated a CD4+ T-cell proliferation in 7 of 21 investigated donor samples. The strength of stimulation response on average ranged from 0.09 to 0.31% above the background in up to 4 donor samples per peptide. For example, the strength of stimulation for BIR-002 was 0.24%. BIR-002 was found to be highly immunogenic in different clinical trials. BIR-002 was tested as a component of a prostate cancer-specific peptide vaccine in a clinical trial with 19 evaluable patients expressing different HLA-DR alleles (Feyerabend et al., 2009). Sixteen (84%) patients mounted a strong CD4+ T-cell response against BIR-002 (Widenmeyer et al., 2008) demonstrating its high immunogenicity potential. In the IMA950 trial, 100% (n=16) of the patients showed an immune response against BIR-002.

By comparison, with exception of FN1-002, the selected peptides for the current analysis stimulated the CD4+ T-cell proliferation in overall 11 investigated donor samples. Thereby, the strength of stimulation response in average ranged from 0.19 to 0.48% above the background in up to 6 donors per peptide. These values were similar to the strength of stimulation response of the highly immunogenic peptide BIR-002. Interestingly, for all positive control peptides the fraction of positive donor samples in the in vitro immunogenicity assay (range: 4-19%) was considerably lower than the fraction of patients mounting an immune response against these peptides in clinical trials (range: 44-100%). This observation indicates that the current in vitro immunogenicity assay setup is rather conservative and is likely to underestimate immunogenicity of the peptides in a clinical setting. Thus, it can be expected that 9 of the 10 investigated peptides are highly likely to induce an in vivo immune response in clinical trials in the majority of patients.

TABLE 27

Results of T-cell proliferation assay of selected peptides and positive control peptides with known in vivo immunogenicity.

| Sequence ID No | Peptide ID | Number of positive donors | Strength of response: mean in % above the background |
|---|---|---|---|
| 86 | MMP12-007 | 2 | 0.28 |
| 87 | COL11A1-001 | 5 | 0.19 |
| 92 | COL1A2-001 | 2 | 0.48 |
| 91 | COL5A2-001 | 2 | 0.21 |
| 88 | ITGB6-001 | 6 | 0.23 |
| 90 | LAMC2-003 | 3 | 0.27 |
| 110 | LAMP3-002 | 5 | 0.25 |
| 89 | IGF2BP3-002 | 3 | 0.40 |
| 162 | POSTN-002 | 2 | 0.39 |
| 165 | BIR-002 | 3 | 0.24 |
| 166 | MET-005 | 4 | 0.31 |
| 167 | MMP-001 | 2 | 0.09 |
| 168 | CEA-006 | 1 | 0.20 |
| 169 | TGFBI-004 | 2 | 0.19 |

REFERENCE LIST

Aaltonen, K. et al., Br. J Cancer 100 (2009): 1055-1060
Abdelzaher, E. et al., Tumour. Biol. (2015)
Acuff, H. B. et al., Cancer Research 66 (2006): 7968-7975
Adhikary, G. et al., PLoS. ONE. 8 (2013): e84324
Agarwal, R. et al., Clinical Cancer Research 15 (2009): 3654-3662
Alcoser, S. Y. et al., BMC. Biotechnol. 11 (2011): 124
Allison, J. P. et al., Science 270 (1995): 932-933
Andersen, R. S. et al., Nat. Protoc. 7 (2012): 891-902
Anderson, N. L. et al., J Proteome. Res 11 (2012): 1868-1878
Appay, V. et al., Eur. J Immunol. 36 (2006): 1805-1814

Asteriti, I. A. et al., Biochim. Biophys. Acta 1806 (2010): 230-239
Badiglian, Filho L. et al., Oncol Rep. 21 (2009): 313-320
Bae, J. S. et al., Biochem. Biophys. Res. Commun. 294 (2002): 940-948
Bafna, S. et al., Oncogene 29 (2010): 2893-2904
Banchereau, J. et al., Cancer Res. 61 (2001): 6451-6458
Bargo, S. et al., Biochem. Biophys. Res Commun. 400 (2010): 606-612
Bartsch, S. et al., J Neurosci. 12 (1992): 736-749
Beatty, G. et al., J Immunol 166 (2001): 2276-2282
Beggs, J. D., Nature 275 (1978): 104-109
Begnami, M. D. et al., Hum. Pathol. 41 (2010): 1120-1127
Beljan, Perak R. et al., Diagn. Pathol. 7 (2012): 165
Benaglio, P. et al., Hum. Mutat. 32 (2011): E2246-E2258
Benjamini, Y. et al., Journal of the Royal Statistical Society.Series B (Methodological), Vol. 57 (1995): 289-300
Bergner, A. et al., J Exp. Clin Cancer Res. 28 (2009): 25
Berndt, A. et al., Histochem. Cell Biol. 133 (2010): 467-475
Berthon, P. et al., Am. J Hum. Genet. 62 (1998): 1416-1424
Bird, A. W. et al., J Cell Biol. 182 (2008): 289-300
Blanco, M. A. et al., Cell Res 22 (2012): 1339-1355
Blatch, G. L. et al., BioEssays 21 (1999): 932-939
Bossard, C. et al., Int. J Cancer 131 (2012): 855-863
Bostrom, P. et al., BMC. Cancer 11 (2011): 348
Boulter, J. M. et al., Protein Eng 16 (2003): 707-711
Bragulla, H. H. et al., J Anat. 214 (2009): 516-559
Braumuller, H. et al., Nature (2013)
Brossart, P. et al., Blood 90 (1997): 1594-1599
Bruckdorfer, T. et al., Curr. Pharm. Biotechnol. 5 (2004): 29-43
Byrne, A. et al., Exp. Cell Res 316 (2010): 258-271
Calabrese, F. et al., Pathology 44 (2012): 192-198
Cao, Y. et al., Cancer Lett. (2015)
Capello, M. et al., FEBS J 278 (2011): 1064-1074
Cappello, P. et al., Int J Cancer 125 (2009): 639-648
Card, K. F. et al., Cancer Immunol. Immunother. 53 (2004): 345-357
Carroll, C. W. et al., Nat Cell Biol. 11 (2009): 896-902
Cataldo, D. D. et al., Cell Mol. Biol. (Noisy.-le-grand) 49 (2003): 875-884
Cedres, S. et al., Clin Lung Cancer 12 (2011): 172-179
Cervantes, M. D. et al., Mol. Cell Biol. 26 (2006): 4690-4700
Chakraborti, S. et al., Mol. Cell Biochem. 253 (2003): 269-285
Chami, M. et al., Oncogene 19 (2000): 2877-2886
Chandler, S. et al., Biochem. Biophys. Res Commun. 228 (1996): 421-429
Chang, G. C. et al., Clinical Cancer Research 12 (2006): 5746-5754
Chanock, S. J. et al., Hum. Immunol. 65 (2004): 1211-1223
Chen, D. R. et al., Anticancer Res. 30 (2010): 4135-4140
Chen, G. et al., Biomed. Res Int. 2014 (2014): 230183
Chen, J. et al., Cancer Cell 19 (2011): 541-555
Chen, M. F. et al., J Mol. Med 87 (2009): 307-320
Chen, P. et al., J Mol. Histol. 43 (2012): 63-70
Chen, Q. et al., Mediators. Inflamm. 2013 (2013): 928315
Chen, Z. S. et al., FEBS J 278 (2011): 3226-3245
Cheon, D. J. et al., Clin. Cancer Res. 20 (2014): 711-723
Chiquet-Ehrismann, R., Semin. Cancer Biol. 4 (1993): 301-310
Chiquet-Ehrismann, R. et al., J Pathol. 200 (2003): 488-499
Cho, N. H. et al., Oncogene 23 (2004): 845-851
Choi, K. U. et al., Int J Cancer (2010)
Chung, F. Y. et al., J Surg. Oncol 102 (2010): 148-153
Cirak, Y. et al., Med. Oncol 30 (2013): 526
Cohen, C. J. et al., J Mol. Recognit. 16 (2003a): 324-332
Cohen, C. J. et al., J Immunol. 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Conde-Perezprina, J. C. et al., Oxid. Med. Cell Longev. 2012 (2012): 728430
Cooper, C. R. et al., J Cell Biochem. 104 (2008): 2298-2309
Cooper, W. A. et al., Histopathology 55 (2009): 28-36
Cordes, C. et al., Anticancer Res 30 (2010): 3541-3547
Creighton, C. J. et al., Mol. Cancer Res 3 (2005): 119-129
Da Forno, P. D. et al., Clinical Cancer Research 14 (2008): 5825-5832
Dai, T. Y. et al., J Exp. Clin Cancer Res 33 (2014): 64
Davidson, N. O., Keio J Med. 56 (2007): 14-20
de Souza Meyer, E. L. et al., Clin Endocrinol. (Oxf) 62 (2005): 672-678
De, Boeck A. et al., Proteomics. 13 (2013): 379-388
De, Luca P. et al., Mol Cancer Res 9 (2011): 1078-1090
De, Vriendt, V et al., Biomarkers 18 (2013): 516-524
Deeley, R. G. et al., Physiol Rev. 86 (2006): 849-899
Dengjel, J. et al., Clin Cancer Res. 12 (2006): 4163-4170
Denkberg, G. et al., J Immunol. 171 (2003): 2197-2207
Denli, A. M. et al., Nature 432 (2004): 231-235
Denys, H. et al., Br. J Cancer 90 (2004): 1443-1449
Dharmavaram, R. M. et al., Matrix Biol. 16 (1998): 343-348
Dolznig, H. et al., Cancer Immun. 5 (2005): 10
Dong, S. et al., J Neuropathol. Exp. Neurol. 64 (2005): 948-955
Drucker, K. L. et al., Genes Chromosomes. Cancer 48 (2009): 854-864
Dulak, A. M. et al., Nat Genet. 45 (2013): 478-486
Egloff, A. M. et al., Ann N.Y. Acad. Sci. 1062 (2005): 29-40
Ellsworth, R. E. et al., Clin. Exp. Metastasis 26 (2009): 205-213
Escobar-Hoyos, L. F. et al., Mod. Pathol. 27 (2014): 621-630
Espinosa, A. M. et al., PLoS. ONE. 8 (2013): e55975
Ewald, J. A. et al., PLoS. ONE. 8 (2013): e55414
Falk, K. et al., Nature 351 (1991): 290-296
Fang, W. Y. et al., Acta Biochim. Biophys. Sin. (Shanghai) 37 (2005): 541-546
Fang, Z. Q. et al., Genet. Mol. Res. 12 (2013): 1479-1489
Feng, C. J. et al., Anticancer Res 28 (2008): 3763-3769
Findeis-Hosey, J. J. et al., Biotech. Histochem. 87 (2012): 24-29
Findeis-Hosey, J. J. et al., Hum. Pathol. 41 (2010): 477-484
Fiorentini, C. et al., Exp. Cell Res 323 (2014): 100-111
Fong, L. et al., Proc. Natl. Acad. Sci. U.S.A 98 (2001): 8809-8814
Forsey, R. W. et al., Biotechnol. Lett. 31 (2009): 819-823
Freire, J. et al., Pathol. Res. Pract. 210 (2014): 879-884
Fuchs, B. C. et al., Am. J Physiol Gastrointest. Liver Physiol 286 (2004): G467-G478
Fuchs, F. et al., Mol Syst. Biol. 6 (2010): 370
Fujita, A. et al., Virchows Arch. 460 (2012): 163-169
Fukuda, T. et al., J Histochem. Cytochem. 55 (2007): 335-345
Fukunaga-Kalabis, M. et al., Oncogene 29 (2010): 6115-6124
Fuller-Pace, F. V., RNA. Biol. 10 (2013): 121-132
Furukawa, T. et al., Sci. Rep. 1 (2011): 161
Furutani, Y. et al., Biochem. J 389 (2005): 675-684
Gabrilovich, D. I. et al., Nat. Med 2 (1996): 1096-1103
Garnett, M. J. et al., Nat. Cell Biol. 11 (2009): 1363-1369
Gattinoni, L. et al., Nat. Rev. Immunol. 6 (2006): 383-393

Ghosh, S. et al., Gynecol. Oncol 119 (2010): 114-120
Gibbs, M. et al., Am. J Hum. Genet. 64 (1999): 1087-1095
Gilkes, D. M. et al., Mol Cancer Res 11 (2013): 456-466
Gladhaug, I. P. et al., Histopathology 56 (2010): 345-355
Gnjatic, S. et al., Proc Natl. Acad. Sci. U.S.A 100 (2003): 8862-8867
Godkin, A. et al., Int. Immunol 9 (1997): 905-911
Gonzalez, A. L. et al., Hum. Pathol. 35 (2004): 840-849
Gooden, M. et al., Proc. Natl. Acad. Sci. U.S.A 108 (2011): 10656-10661
Gorrin Rivas, M. J. et al., Hepatology 28 (1998): 986-993
Gorrin-Rivas, M. J. et al., Ann Surg 231 (2000): 67-73
Graf, F. et al., Mini. Rev. Med. Chem. 10 (2010): 527-539
Graf, M. et al., Eur. J Haematol. 75 (2005): 477-484
Green, M. R. et al., Molecular Cloning, A Laboratory Manual 4th (2012)
Greenfield, E. A., Antibodies: A Laboratory Manual 2nd (2014)
Gregory, K. E. et al., J Bone Miner. Res. 16 (2001): 2005-2016
Grunda, J. M. et al., Clin Cancer Res. 16 (2010): 2890-2898
Grupp, K. et al., Mol Oncol 7 (2013): 1001-1011
Gupta, N. et al., Biochim. Biophys. Acta 1741 (2005): 215-223
Gupta, N. et al., Gynecol. Oncol 100 (2006): 8-13
Hagemann, T. et al., Eur. J Cancer 37 (2001): 1839-1846
Hamamoto, R. et al., Cancer Sci. 97 (2006): 113-118
Han, J. et al., Cell 125 (2006): 887-901
Hannisdal, K. et al., Head Neck 32 (2010): 1354-1362
Hatina, J. et al., Neoplasma 59 (2012): 728-736
He, P. et al., Cancer Sci. 98 (2007): 1234-1240
Hernandez, I. et al., Oncogene 29 (2010): 3758-3769
Hodgson, J. G. et al., Neuro Oncol 11 (2009): 477-487
Hofmann, H. S. et al., Am. J Respir. Crit Care Med. 170 (2004): 516-519
Hofmann, H. S. et al., Clinical Cancer Research 11 (2005): 1086-1092
Hood, F. E. et al., Bioarchitecture. 1 (2011): 105-109
Houghton, A. M. et al., Cancer Research 66 (2006): 6149-6155
Hourihan, R. N. et al., Anticancer Res 23 (2003): 161-165
Hu, Y. et al., Carcinogenesis 34 (2013): 176-182
Huang, C. et al., Cancer Epidemiol. Biomarkers Prev. 21 (2012a): 166-175
Huang, C. L. et al., J Clin Oncol 23 (2005): 8765-8773
Huang, M. Y. et al., DNA Cell Biol. 31 (2012b): 625-635
Huang, T. et al., Int. J Clin Exp.Pathol. 7 (2014): 1544-1552
Huo, J. et al., Arch. Dermatol. Res. 302 (2010): 769-772
Hwang, M. L. et al., J Immunol. 179 (2007): 5829-5838
Hwang, Y. S. et al., Head Neck 34 (2012): 1329-1339
Ida-Yonemochi, H. et al., Mod. Pathol. 25 (2012): 784-794
Imadome, K. et al., Cancer Biol.Ther 10 (2010): 1019-1026
Irigoyen, M. et al., Mol. Cancer 9 (2010): 130
Ishikawa, N. et al., Clin Cancer Res. 10 (2004): 8363-8370
Ishikawa, Y. et al., J Biol.Chem. 283 (2008): 31584-31590
Iuchi, S. et al., Proc. Natl. Acad. Sci. U.S.A 96 (1999): 9628-9632
Ivanov, S. V. et al., Biochem. Biophys. Res. Commun. 370 (2008): 536-540
Jeng, Y. M. et al., Br. J Surg 96 (2009): 66-73
Jensen, K. et al., J Pathol. 221 (2010): 193-200
Jung, C. K. et al., Pathol. Int 56 (2006): 503-509
Jung, G. et al., Proc Natl Acad Sci USA 84 (1987): 4611-4615
Kabbarah, O. et al., PLoS. ONE. 5 (2010): e10770
Kadara, H. et al., Cancer Prev. Res (Phila) 2 (2009): 702-711
Kanai, Y. et al., Mol Aspects Med. 34 (2013): 108-120
Kanno, A. et al., Int J Cancer 122 (2008): 2707-2718
Karantza, V., Oncogene 30 (2011): 127-138
Karunakaran, S. et al., J Biol. Chem. 286 (2011): 31830-31838
Kastrinos, F. et al., Semin. Oncol 34 (2007): 418-424
Katagiri, C. et al., J Dermatol. Sci. 57 (2010): 95-101
Katoh, M., Curr. Drug Targets. 9 (2008): 565-570
Katoh, M. et al., Int J Mol. Med 19 (2007): 273-278
Kennedy, A. et al., Int J Cancer 124 (2009): 27-35
Kibbe, A. H., Handbook of Pharmaceutical Excipients rd (2000)
Kikuchi, A. et al., Acta Physiol (Oxf) 204 (2012): 17-33
Kikuchi, Y. et al., J Histochem. Cytochem. 56 (2008): 753-764
Kim, C. H. et al., Surg Neurol. 54 (2000): 235-240
Kim, C. Y. et al., Oncol. Rep. 27 (2012): 608-620
Kim, E. H. et al., Oncogene 29 (2010a): 4725-4731
Kim, H. S. et al., Korean J Intern. Med. 25 (2010b): 399-407
Kim, S. et al., Korean J Hepatol. 10 (2004): 62-72
Kitahara, O. et al., Cancer Res. 61 (2001): 3544-3549
Knight, H. M. et al., Am J Hum. Genet. 85 (2009): 833-846
Korosec, B. et al., Cancer Genet. Cytogenet. 171 (2006): 105-111
Krieg, A. M., Nat. Rev. Drug Discov. 5 (2006): 471-484
Kuan, C. T. et al., Clinical Cancer Research 12 (2006): 1970-1982
Kuang, S. Q. et al., Leukemia 22 (2008): 1529-1538
Kubo, H. et al., BMC. Cancer 14 (2014): 755
Kudo, Y. et al., Cancer Research 66 (2006): 6928-6935
Kwon, O. H. et al., Biochem. Biophys. Res. Commun. 406 (2011): 539-545
Kwon, Y. J. et al., Oncol Res 18 (2009): 141-151
Labied, S. et al., Hum. Reprod. 24 (2009): 113-121
Ladanyi, A. et al., Cancer Immunol. Immunother. 56 (2007): 1459-1469
Lamba, J. K. et al., Pharmacogenomics. 15 (2014): 1565-1574
Langbein, L. et al., J Biol. Chem. 285 (2010): 36909-36921
Langenskiold, M. et al., Scand. J Gastroenterol. 48 (2013): 563-569
Lau, E. et al., EMBO Rep. 7 (2006): 425-430
Lee, J. I. et al., World J Gastroenterol. 18 (2012): 4751-4757
Lee, Y. et al., Nature 425 (2003): 415-419
Lee, Y. K. et al., Br. J Cancer 101 (2009): 504-510
Leivo, I. et al., Cancer Genet. Cytogenet. 156 (2005): 104-113
Li, C. et al., Proteomics. 6 (2006): 547-558
Li, H. G. et al., J Craniofac. Surg. 22 (2011): 2022-2025
Li, J. et al., Cancer Biol. Ther. 10 (2010a): 617-624
Li, J. Q. et al., Int. J Oncol 22 (2003): 1101-1110
Li, M. et al., Lung Cancer 69 (2010b): 341-347
Li, X. et al., Neoplasma 59 (2012): 500-507
Li, Y. N. et al., APMIS 122 (2014): 140-146
Liang, W. J. et al., Ai. Zheng. 27 (2008a): 460-465
Liang, Y. et al., J Neurooncol. 86 (2008b): 133-141
Liao, B. et al., J Biol.Chem. 286 (2011): 31145-31152
Liao, B. et al., J Biol.Chem. 280 (2005): 18517-18524
Liddy, N. et al., Nat. Med. 18 (2012): 980-987
Lim, J. H. et al., J Cell Biochem. 105 (2008): 1117-1127
Lin, D. M. et al., Zhonghua Bing. Li Xue. Za Zhi. 35 (2006): 540-544
Lindskog, C. et al., FASEB J (2014)
Litjens, S. H. et al., Trends Cell Biol. 16 (2006): 376-383
Liu, J. et al., Pathol. Res Pract. 206 (2010): 602-606
Liu, T. et al., PLoS. ONE. 7 (2012): e45464
Liu, Z. et al., Mol Neurobiol. 47 (2013): 325-336
Ljunggren, H. G. et al., J Exp. Med 162 (1985): 1745-1759

Loh, E. et al., J Biol. Chem. 279 (2004): 24640-24648
Longenecker, B. M. et al., Ann N.Y. Acad. Sci. 690 (1993): 276-291
Lu, D. et al., Am. J Surg. Pathol. 35 (2011): 1638-1645
Lu, Y. et al., Am. J Transl. Res 3 (2010): 8-27
Lugassy, C. et al., J Cutan. Pathol. 36 (2009): 1237-1243
Lukas, T. J. et al., Proc. Natl. Acad. Sci. U.S.A 78 (1981): 2791-2795
Lundblad, R. L., Chemical Reagents for Protein Modification 3rd (2004)
Lv, M. et al., Exp. Lung Res. 41 (2015): 74-83
Ma, L. J. et al., Arch. Med Res 40 (2009): 114-123
Ma, T. S. et al., Cell Calcium 26 (1999): 25-36
Ma, Y. et al., Clinical Cancer Research 12 (2006): 1121-1127
Maciejczyk, A. et al., J Histochem.Cytochem. 61 (2013): 330-339
Mackie, E. J. et al., J Cell Biol. 107 (1988): 2757-2767
MacLennan, D. H. et al., J Biol.Chem. 272 (1997): 28815-28818
Maeder, C. et al., Nat Struct. Mol. Biol. 16 (2009): 42-48
Mandi, K. M. et al., Asian Pac. J Cancer Prev. 14 (2013): 3403-3409
Manda, R. et al., Biochem. Biophys. Res. Commun. 275 (2000): 440-445
Mansilla, F. et al., J Mol Med.(Berl) 87 (2009): 85-97
Marchand, M. et al., Int. J. Cancer 80 (1999): 219-230
Marchand, M. et al., Int. J Cancer 63 (1995): 883-885
McClelland, S. E. et al., EMBO J 26 (2007): 5033-5047
McManus, K. J. et al., Proc. Natl. Acad. Sci. U.S.A 106 (2009): 3276-3281
Merscher, S. et al., Front Endocrinol. (Lausanne) 5 (2014): 127
Metz, R. L. et al., Breast Cancer Res 9 (2007): R58
Metz, R. L. et al., Cell Cycle 4 (2005): 315-322
Meyer, E. L. et al., Mol. Cell Endocrinol. 289 (2008): 16-22
Meziere, C. et al., J Immunol 159 (1997): 3230-3237
Middel, P. et al., BMC. Cancer 10 (2010): 578
Mikami, T. et al., Oral Oncol. 47 (2011): 497-503
Miller, N. H. et al., Hum. Hered. 74 (2012): 36-44
Milovanovic, T. et al., Int. J Oncol 25 (2004): 1337-1342
Mochizuki, S. et al., Cancer Sci. 98 (2007): 621-628
Morgan, R. A. et al., Science (2006)
Mori, M. et al., Transplantation 64 (1997): 1017-1027
Morita, Y. et al., J Hepatol. 59 (2013): 292-299
Morris, M. R. et al., Oncogene 29 (2010): 2104-2117
Mortara, L. et al., Clin Cancer Res. 12 (2006): 3435-3443
Moss, D. K. et al., J Cell Sci. 122 (2009): 644-655
Mueller, L. N. et al., J Proteome.Res. 7 (2008): 51-61
Mueller, L. N. et al., Proteomics. 7 (2007): 3470-3480
Mumberg, D. et al., Proc. Natl. Acad. Sci. U.S.A 96 (1999): 8633-8638
Murakami, M. et al., J Clin Endocrinol. Metab 85 (2000): 4403-4406
Nag, A. et al., RNA. Biol. 9 (2012): 334-342
Narita, D. et al., Rom. J Morphol. Embryol. 52 (2011): 1261-1267
Nestle, F. O. et al., Nat Med. 4 (1998): 328-332
Nicastri, A. et al., J Proteome. Res (2014)
Niehof, M. et al., Gastroenterology 134 (2008): 1191-1202
Nishinakamura, R. et al., Pediatr. Nephrol. 26 (2011): 1463-1467
Noda, T. et al., Liver Int. 32 (2012): 110-118
Nones, K. et al., Int. J Cancer 135 (2014): 1110-1118
Odermatt, A. et al., Nat Genet. 14 (1996): 191-194
Oh, S. P. et al., Genomics 14 (1992): 225-231
Ohta, S. et al., Oncol Rep. 8 (2001): 1063-1066
Ortega, P. et al., Int. J Oncol 36 (2010): 1209-1215
Ostroff, R. M. et al., PLoS. ONE. 5 (2010): e15003
Park, S. H. et al., Clinical Cancer Research 13 (2007): 858-867
Paron, I. et al., PLoS. ONE. 6 (2011): e21684
Pascreau, G. et al., J Biol. Chem. 284 (2009): 5497-5505
Patterson, C. E. et al., Cell Stress. Chaperones. 10 (2005): 285-295
Patterson, C. E. et al., Mol. Biol. Cell 11 (2000): 3925-3935
Pernemalm, M. et al., J Proteome. Res 12 (2013): 3934-3943
Perrin-Tricaud, C. et al., PLoS. ONE. 6 (2011): e29390
Perumal, D. et al., PLoS. ONE. 7 (2012): e43589
Pinheiro, J. et al., nlme: Linear and Nonlinear Mixed Effects Models (http://CRAN.R-project.org/packe=nlme) (2015)
Plebanski, M. et al., Eur. J Immunol 25 (1995): 1783-1787
Plones, T. et al., PLoS. ONE. 7 (2012): e41746
Pokrovskaya, I. D. et al., Glycobiology 21 (2011): 1554-1569
Pontisso, P. et al., Br. J Cancer 90 (2004): 833-837
Porta, C. et al., Virology 202 (1994): 949-955
Prades, C. et al., Cytogenet. Genome Res 98 (2002): 160-168
Prasad, P. et al., BMC. Med. Genet. 11 (2010): 52
Puppin, C. et al., J Endocrinol. 197 (2008): 401-408
Puri, V. et al., Biol. Psychiatry 61 (2007): 873-879
Puyol, M. et al., Cancer Cell 18 (2010): 63-73
Qin, C. et al., Mol Med. Rep. 9 (2014): 851-856
Qu, P. et al., Cancer Research 69 (2009): 7252-7261
Quaas, M. et al., Cell Cycle 11 (2012): 4661-4672
Rajkumar, T. et al., BMC. Cancer 11 (2011): 80
Ramakrishna, M. et al., PLoS. ONE. 5 (2010): e9983
Ramirez, N. E. et al., J Clin Invest 121 (2011): 226-237
Rammensee, H. G. et al., Immunogenetics 50 (1999): 213-219
Reinmuth, N. et al., Dtsch. Med. Wochenschr. 140 (2015): 329-333
Renkonen, S. et al., Head Neck (2012)
Rettig, W. J. et al., Cancer Research 53 (1993): 3327-3335
Rettig, W. J. et al., Int J Cancer 58 (1994): 385-392
Rini, B. I. et al., Cancer 107 (2006): 67-74
Ripka, S. et al., Carcinogenesis 28 (2007): 1178-1187
Ritzenthaler, J. D. et al., Mol Biosyst. 4 (2008): 1160-1169
Rock, K. L. et al., Science 249 (1990): 918-921
Rodenko, B. et al., Nat. Protoc. 1 (2006): 1120-1132
Rodningen, O. K. et al., Radiother. Oncol 86 (2008): 314-320
Roemer, A. et al., Oncol Rep. 11 (2004a): 529-536
Roemer, A. et al., J Urol. 172 (2004b): 2162-2166
Romagnoli, S. et al., Am J Pathol. 174 (2009): 762-770
Rose, A. A. et al., Mol Cancer Res 5 (2007): 1001-1014
Rotty, J. D. et al., J Cell Biol. 197 (2012): 381-389
Ruan, K. et al., Cell Mol.Life Sci. 66 (2009): 2219-2230
S3-Leitlinie Lungenkarzinom, 020/007, (2011)
Sagara, N. et al., Biochem. Biophys. Res. Commun. 252 (1998): 117-122
Saiki, R. K. et al., Science 239 (1988): 487-491
Sakuntabhai, A. et al., Nat Genet. 21 (1999): 271-277
Samanta, S. et al., Oncogene 31 (2012): 4689-4697
Sameer, A. S. et al., Eur. J Cancer Prev. 23 (2014): 246-257
Sandel, M. H. et al., Clinical Cancer Research 11 (2005): 2576-2582
Sang, Q. X., Cell Res 8 (1998): 171-177
Sarai, N. et al., Nucleic Acids Res. 36 (2008): 5441-5450
Satow, R. et al., Clinical Cancer Research 16 (2010): 2518-2528
Scanlan, M. J. et al., Proc Natl. Acad. Sci. U.S.A 91 (1994): 5657-5661
Schalken, J. A. et al., Urology 62 (2003): 11-20

Schegg, B. et al., Mol. Cell Biol. 29 (2009): 943-952
Schleypen, J. S. et al., Int. J Cancer 106 (2003): 905-912
Schneider, D. et al., Biochim. Biophys. Acta 1588 (2002): 1-6
Schuetz, C. S. et al., Cancer Research 66 (2006): 5278-5286
Seeger, F. H. et al., Immunogenetics 49 (1999): 571-576
SEER Stat facts, (2014), http://seer.cancer.gov/Shaikhibrahim,
Z. et al., Int. J Mol Med. 28 (2011): 605-611
Shao, G. et al., Cancer Res. 66 (2006): 4566-4573
Shappell, S. B. et al., Neoplasia. 3 (2001): 287-303
Shepherd, F. A. et al., J Clin. Oncol. 31 (2013): 2173-2181
Sherman, F. et al., Laboratory Course Manual for Methods in Yeast Genetics (1986)
Sherman-Baust, C. A. et al., Cancer Cell 3 (2003): 377-386
Sheu, B. C. et al., Cancer Res. 65 (2005): 2921-2929
Shigeishi, H. et al., Int J Oncol 34 (2009): 1565-1571
Shimbo, T. et al., PLoS. ONE. 5 (2010): e10566
Shubbar, E. et al., BMC. Cancer 13 (2013): 1
Shyian, M. et al., Exp. Oncol 33 (2011): 94-98
Silva, F. C. et al., Sao Paulo Med.J 127 (2009): 46-51
Silva, L. P. et al., Anal. Chem. 85 (2013): 9536-9542
Simpson, N. E. et al., Breast Cancer Res.Treat. 133 (2012): 959-968
Singh, R., Br. J Cancer 83 (2000): 1654-1658
Singh-Jasuja, H. et al., Cancer Immunol. Immunother. 53 (2004): 187-195
Siu, A. et al., Anticancer Res. 32 (2012): 3683-3688
Slack, F. J. et al., N. Engl. J Med. 359 (2008): 2720-2722
Slany, A. et al., J Proteome. Res 13 (2014): 844-854
Sloan, J. L. et al., J Biol.Chem. 274 (1999): 23740-23745
Small, E. J. et al., J Clin Oncol. 24 (2006): 3089-3094
Smith, M. J. et al., Br. J Cancer 100 (2009a): 1452-1464
Smith, S. C. et al., Am J Pathol. 174 (2009b): 371-379
Solomon, S. et al., Cancer J 18 (2012): 485-491
Spataro, V. et al., Anticancer Res 22 (2002): 3905-3909
Spataro, V. et al., J Biol. Chem. 272 (1997): 30470-30475
Starzyk, R. M. et al., J Infect. Dis. 181 (2000): 181-187
Steffens, S. et al., Oncol Lett. 3 (2012): 787-790
Stuart, J. E. et al., J Neuropathol. Exp. Neurol. (2010)
Sturm, M. et al., BMC. Bioinformatics. 9 (2008): 163
Suminami, Y. et al., Biochem. Biophys. Res. Commun. 181 (1991): 51-58
Suvasini, R. et al., J Biol. Chem. 286 (2011): 25882-25890
Takanami, I. et al., Int J Biol. Markers 23 (2008): 182-186
Takashima, S. et al., Tumour. Biol. 35 (2014): 4257-4265
Tanaka, S. et al., Proc. Natl. Acad. Sci. U.S.A 95 (1998): 10164-10169
Terabayashi, T. et al., PLoS. ONE. 7 (2012): e39714
Teufel, R. et al., Cell Mol. Life Sci. 62 (2005): 1755-1762
Thierry, L. et al., J Mol. Histol. 35 (2004): 803-810
Thorsen, K. et al., Mol. Cell Proteomics. 7 (2008): 1214-1224
Thurner, B. et al., J Exp. Med 190 (1999): 1669-1678
Tischler, V. et al., BMC. Cancer 10 (2010): 273
Tondreau, T. et al., BMC. Genomics 9 (2008): 166
Tong, W. G. et al., Epigenetics. 5 (2010): 499-508
Torre, G. C., Tumour. Biol. 19 (1998): 517-526
Tran, E. et al., Science 344 (2014): 641-645
Travis, W. D. et al., J Clin. Oncol. 31 (2013): 992-1001
Troy, T. C. et al., Stem Cell Rev. 7 (2011): 927-934
Tsai, J. R. et al., Lung Cancer 56 (2007): 185-192
Tseng, H., Front Biosci. 3 (1998): D985-D988
Tseng, H. et al., J Cell Sci. 112 Pt 19 (1999): 3039-3047
Tseng, H. et al., J Cell Biol. 126 (1994): 495-506
Tsuji, A. et al., Biochem.J 396 (2006): 51-59
Tsukamoto, Y. et al., J Pathol. 216 (2008): 471-482
Uchiyama, Y. et al., Proc. Natl. Acad. Sci. U.S.A 107 (2010): 9240-9245
Ullman, E. et al., Mol. Cell Biol. 31 (2011): 2902-2919
Urquidi, V. et al., PLoS. ONE. 7 (2012): e37797
Utispan, K. et al., Mol. Cancer 9 (2010): 13
van, Asseldonk M. et al., Genomics 66 (2000): 35-42
Vazquez-Ortiz, G. et al., BMC. Cancer 5 (2005): 68
Vermeulen, K. et al., Cell Prolif. 36 (2003): 131-149
Vilar, E. et al., Nat Rev. Clin Oncol 7 (2010): 153-162
von, Au A. et al., Neoplasia. 15 (2013): 925-938
Waalkes, S. et al., BMC. Cancer 10 (2010): 503
Walchli, C. et al., J Cell Sci. 107 (Pt 2) (1994): 669-681
Wallace, A. M. et al., COPD. 5 (2008): 13-23
Walter, S. et al., J.Immunol. 171 (2003): 4974-4978
Walter S et al., J Immunother (SITC Annual Meeting 2011) 35, (2012)
Wang, H. Y. et al., Cancer Lett. 191 (2003): 229-237
Wang, L. et al., J Thorac. Dis. 6 (2014): 1380-1387
Wang, Q. et al., J Natl. Cancer Inst. 105 (2013a): 1463-1473
Wang, S. Z. et al., BMB. Rep. 41 (2008): 294-299
Wang, W. X. et al., Sichuan. Da. Xue. Xue. Bao. Yi. Xue. Ban. 40 (2009): 857-860
Wang, Y. F. et al., Tumour. Biol. 34 (2013b): 1685-1689
Warner, S. L. et al., Clinical Cancer Research 15 (2009): 6519-6528
Watanabe, M. et al., Proteomics. Clin Appl. 2 (2008): 925-935
Watt, S. L. et al., J Biol. Chem. 267 (1992): 20093-20099
Wawrzynska, L. et al., Monaldi Arch. Chest Dis. 59 (2003): 140-145
Weeraratna, A. T. et al., Cancer Cell 1 (2002): 279-288
Weiner, L. et al., Differentiation 63 (1998): 263-272
Wen, G. et al., Cancer Lett. 308 (2011): 23-32
Wildeboer, D. et al., J Neuropathol. Exp. Neurol. 65 (2006): 516-527
Wilke, S. et al., BMC. Biol. 10 (2012): 62
Willcox, B. E. et al., Protein Sci. 8 (1999): 2418-2423
Willett, R. et al., Nat Commun. 4 (2013): 1553
World Cancer Report, (2014)
Wu, A. et al., J Transl. Med. 9 (2011): 38
Wu, D. et al., Mol. Med.Rep. 10 (2014a): 2415-2420
Wu, G. C. et al., Ai.Zheng. 27 (2008): 874-878
Wu, H. et al., J Biol. Chem. 275 (2000): 36957-36965
Wu, J. et al., BMC. Clin Pathol. 13 (2013a): 15
Wu, K. D. et al., Am. J Physiol 269 (1995): C775-C784
Wu, M. et al., BMC. Cancer 13 (2013b): 44
Wu, S. Q. et al., Mol. Med.Rep. 7 (2013c): 875-880
Wu, Y. H. et al., Oncogene 33 (2014b): 3432-3440
Xiao, L. et al., Biochem. J 403 (2007): 573-581
Xiao, X. et al., Gynecol. Oncol 132 (2014): 506-512
Xiao, X. Y. et al., Tumour. Biol. 33 (2012): 2385-2392
Xiong, D. et al., Carcinogenesis 33 (2012): 1797-1805
Xu, B. et al., Br. J Cancer 109 (2013): 1279-1286
Xu, X. Y. et al., Pathol. Res Pract. (2014)
Xu, Y. et al., PLoS. ONE. 6 (2011): e21119
Yamamoto, H. et al., Oncogene 29 (2010): 2036-2046
Yan, Z. et al., Biomark. Insights. 9 (2014): 67-76
Yang, S. et al., Biochim. Biophys. Acta 1772 (2007): 1033-1040
Yasui, W. et al., Cancer Sci. 95 (2004): 385-392
Ye, H. et al., BMC. Genomics 9 (2008): 69
Yin, J. Y. et al., Clin Exp. Pharmacol. Physiol 38 (2011): 632-637
Yoon, H. et al., Proc Natl. Acad. Sci. U.S.A 99 (2002): 15632-15637
Yoshida, K. et al., J Cell Sci. 123 (2010): 225-235
Younes, M. et al., Anticancer Res 20 (2000): 3775-3779

Yu, D. et al., Int. J Mol Sci. 14 (2013): 11145-11156
Yu, J. et al., Gut (2014)
Yu, J. M. et al., Cancer Lett. 257 (2007): 172-181
Yuan, A. et al., APMIS 116 (2008): 445-456
Yuzugullu, H. et al., Mol. Cancer 8 (2009): 90
Zaremba, S. et al., Cancer Res. 57 (1997): 4570-4577
Zeitlin, S. G. et al., Proc. Natl. Acad. Sci. U.S.A 106 (2009): 15762-15767
Zhang, C. et al., PLoS. ONE. 6 (2011): e23849
Zhang, C. et al., Am. J Clin Pathol. 142 (2014): 320-324
Zhang, H. et al., J Clin Endocrinol. Metab 89 (2004): 748-755
Zhang, J. et al., Front Biosci. (Elite. Ed) 2 (2010a): 1154-1163
Zhang, J. Y. et al., Cancer Epidemiol. Biomarkers Prev. 12 (2003): 136-143
Zhang, L. et al., Am. J Pathol. 182 (2013): 2048-2057
Zhang, Y. et al., J Cell Sci. 123 (2010b): 1285-1294
Zhang, Y. et al., J Surg Res 160 (2010c): 102-106
Zhao, C. et al., Am. J Hum. Genet. 85 (2009a): 617-627
Zhao, H. et al., Cancer Gene Ther 21 (2014a): 448-455
Zhao, W. et al., Int. J Clin Exp. Pathol. 7 (2014b): 4247-4253
Zhao, Y. et al., Mol. Carcinog. 45 (2006): 84-92
Zhao, Y. et al., Radiat. Res. 162 (2004): 655-659
Zhao, Y. et al., Anat. Rec. (Hoboken.) 292 (2009b): 692-700
Zhao, Z. et al., Genomics 27 (1995): 370-373
Zheng, P. S. et al., FASEB J 18 (2004): 754-756
Zhou, X. et al., Exp. Mol Pathol. 92 (2012): 105-110
Zong, J. et al., Clin. Transl. Oncol. 14 (2012): 21-30
Zou, J. N. et al., Cancer Lett. 280 (2009): 78-85
Zou, T. T. et al., Oncogene 21 (2002): 4855-4862
Allen, M. D. et al., Clin Cancer Res. 20 (2014): 344-357
Ammendola, M. et al., Biomed. Res. Int. 2014 (2014): 154702
An, J. et al., Mol Cancer 7 (2008): 32
Angenieux, C. et al., PLoS. ONE. 7 (2012): e42634
Arafeh, R. et al., Nat Genet. 47 (2015): 1408-1410
Atkins, D. et al., Contrib. Nephrol. 148 (2005): 35-56
Barras, D. et al., Int. J Cancer 135 (2014): 242-247
Barros-Filho, M. C. et al., J Clin Endocrinol. Metab 100 (2015): E890-E899
Beaudry, V. G. et al., PLoS. Genet. 6 (2010): e1001168
Beckmann, R. P. et al., Science 248 (1990): 850-854
Bengtsson, L. et al., J Cell Sci. 121 (2008): 536-548
Bloch, D. B. et al., J Biol Chem 271 (1996): 29198-29204
Bosch, D. G. et al., Eur. J Hum. Genet. (2015)
Boyer, A. P. et al., Mol. Cell Proteomics. 12 (2013): 180-193
Brooks, W. S. et al., J Biol Chem 283 (2008): 22304-22315
Bukau, B. et al., Cell 92 (1998): 351-366
Burger, M., Dig. Dis. Sci. 54 (2009): 197-198
Cailliau, K. et al., J Biol Chem 290 (2015): 19653-19665
Cao, Q. F. et al., Cancer Biother. Radiopharm. 30 (2015): 87-93
Chakrabarti, G. et al., Cancer Metab 3 (2015): 12
Chalitchagorn, K. et al., Oncogene 23 (2004): 8841-8846
Chen, K. et al., Cancer Biol Ther. 12 (2011): 1114-1119
Chen, S. J. et al., J Biol. Chem 289 (2014): 36284-36302
Chen, Y. Z. et al., Cancer Chemother. Pharmacol. 70 (2012): 637-644
Chevrollier, A. et al., Biochim. Biophys. Acta 1807 (2011): 562-567
Chouchane, L. et al., Cancer 80 (1997): 1489-1496
Ciocca, D. R. et al., Cell Stress. Chaperones. 10 (2005): 86-103
Ciocca, D. R. et al., Cancer Res. 52 (1992): 3648-3654
Cipriano, R. et al., Mol. Cancer Res. 12 (2014): 1156-1165
Cortese, R. et al., Int. J Biochem. Cell Biol 40 (2008): 1494-1508
Critchley-Thorne, R. J. et al., PLoS. Med. 4 (2007): e176
Das, M. et al., PLoS. ONE. 8 (2013): e69607
Decker, T. et al., J Clin Invest 109 (2002): 1271-1277
Di, K. et al., Oncogene 32 (2013): 5038-5047
Dolce, V. et al., FEBS Lett. 579 (2005): 633-637
Draberova, E. et al., J Neuropathol. Exp. Neurol. 74 (2015): 723-742
Dunwell, T. L. et al., Epigenetics. 4 (2009): 185-193
Dusek, R. L. et al., Breast Cancer Res 14 (2012): R65
Ene, C. I. et al., PLoS. ONE. 7 (2012): e51407
Espinal-Enriquez, J. et al., BMC. Genomics 16 (2015): 207
Evert, M. et al., Br. J Cancer 109 (2013): 2654-2664
Fellenberg, F. et al., J Invest Dermatol. 122 (2004): 1510-1517
Feng, F. et al., Mol. Cancer 9 (2010): 90
Ferrer-Ferrer, M. et al., Arch. Med. Res 44 (2013): 467-474
Fischer, H. et al., Carcinogenesis 22 (2001): 875-878
Freiss, G. et al., Bull. Cancer 91 (2004): 325-332
Freiss, G. et al., Anticancer Agents Med.Chem 11 (2011): 78-88
Friedman, E., Pathobiology 63 (1995): 348-350
Fu, B. S. et al., Nan. Fang Yi. Ke. Da. Xue. Xue. Bao. 29 (2009): 1775-1778
Gallerne, C. et al., Int. J Biochem. Cell Biol 42 (2010): 623-629
Garg, M. et al., Cancer 116 (2010a): 3785-3796
Garg, M. et al., Cancer 116 (2010b): 3785-3796
Garg, M. et al., Eur. J Cancer 46 (2010c): 207-215
Gautier, T. et al., FASEB J 24 (2010): 3544-3554
Giaginis, C. et al., Dig. Dis. Sci. 56 (2011): 777-785
Giovannini, D. et al., Cell Rep. 3 (2013): 1866-1873
Gokmen-Polar, Y. et al., Mod. Pathol. 28 (2015): 677-685
Guo, H. et al., Cancer Research 71 (2011): 7576-7586
Haffner, C. et al., EMBO J 23 (2004): 3041-3050
Hartl, F. U. et al., Science 295 (2002): 1852-1858
Hatfield, M. P. et al., Protein Pept. Lett. 19 (2012): 616-624
Hayward, A. et al., PLoS. ONE. 8 (2013): e59940
Hillier, L. W. et al., Nature 424 (2003): 157-164
Hsiung, D. T. et al., Cancer Epidemiol. Biomarkers Prev. 16 (2007): 108-114
Huang, F. et al., Int. J Clin Exp. Pathol. 7 (2014a): 1093-1100
Huang, G. et al., Anticancer Agents Med. Chem 14 (2014b): 9-17
Huang, L. et al., Int. J Gynecol. Cancer 25 (2015a): 559-565
Huang, S. et al., Oncogene 21 (2002): 2504-2512
Huang, X. et al., Cancer Cell Int. 15 (2015b): 93
Imada, A. et al., Eur. Respir. J 15 (2000): 1087-1093
Inoue, J. et al., PLoS. ONE. 4 (2009): e7099
Ishii, M. et al., Anticancer Res. 27 (2007): 3987-3992
Ito, Y. et al., J Biochem. 124 (1998): 347-353
Jalbout, M. et al., Cancer Lett. 193 (2003): 75-81
Jia, W. H. et al., Nat. Genet. 45 (2013): 191-196
Jie, Liu et al., Pathol. Res Pract. 210 (2014): 176-181
Jin, X. et al., Tumour. Biol (2015)
Johnson, M. et al., Cell Signal. 21 (2009): 1471-1478
Kankavi, O. et al., Ren Fail. 36 (2014): 258-265
Kao, R. H. et al., Int. J Exp. Pathol. 84 (2003): 207-212
Kim, H. S. et al., Korean J Intern. Med. 25 (2010): 399-407
Kobayashi, K. et al., Oncogene 23 (2004): 3089-3096
Kong, C. S. et al., Oral Surg. Oral Med. Oral Pathol. Oral Radiol. 115 (2013): 95-103
Kortum, K. M. et al., Ann. Hematol. 94 (2015): 1205-1211
Kozak, C. A., Retrovirology. 7 (2010): 101
Kresse, S. H. et al., Mol. Cancer 7 (2008): 48

Kukita, K. et al., J Immunol. 194 (2015): 4988-4996
Kutomi, G. et al., Cancer Sci. 104 (2013): 1091-1096
Kwok, H. F. et al., Am. J Cancer Res 5 (2015): 52-71
Lai, C. H. et al., Genome Res 10 (2000): 703-713
Lan, Q. et al., Eur. J Haematol. 85 (2010): 492-495
Lange, A. et al., Exp. Dermatol. 18 (2009): 527-535
Lazaris, A. C. et al., Breast Cancer Res. Treat. 43 (1997): 43-51
Lee, K. Y. et al., Yonsei Med.J 50 (2009): 60-67
Leypoldt, F. et al., J Neurochem. 76 (2001): 806-814
Li, Q. et al., Int. J Clin Exp. Pathol. 8 (2015): 6334-6344
Li, Y. et al., Neoplasia. 7 (2005): 1073-1080
Liang, B. et al., Clin Cancer Res. 21 (2015): 1183-1195
Liu, B. et al., PLoS. ONE. 7 (2012): e43147
Liu, L. et al., Biochem. Biophys. Res. Commun. 372 (2008): 756-760
Liu, Y. et al., Cancer Research 69 (2009): 7844-7850
Lv, Q. et al., Tumour. Biol 36 (2015): 3751-3756
Lynch, E. M. et al., Curr. Biol 24 (2014): 896-903
Ma, J. et al., Cell Physiol Biochem. 37 (2015): 201-213
Maitra, M. et al., Proc. Natl. Acad. Sci. U.S.A 109 (2012): 21064-21069
Manuel, A. et al., Genomics 64 (2000): 216-220
Martin, C. et al., J Virol. 87 (2013): 10094-10104
May, D. et al., Oncogene 24 (2005): 1011-1020
Medhi, S. et al., J Viral Hepat. 20 (2013): e141-e147
Mei, J. et al., Oncogene 25 (2006): 849-856
Mestiri, S. et al., Cancer 91 (2001): 672-678
Meulmeester, E. et al., Curr. Cancer Drug Targets. 8 (2008): 87-97
Mimoto, R. et al., Cancer Lett. 339 (2013): 214-225
Mitsuhashi, A. et al., Am. J Pathol. 182 (2013): 1843-1853
Moudry, P. et al., Cell Cycle 11 (2012): 1573-1582
Mungall, A. J. et al., Nature 425 (2003): 805-811
Nagamachi, A. et al., Cancer Cell 24 (2013): 305-317
Nagao, H. et al., PLoS. ONE. 7 (2012): e39268
Narita, N. et al., Int. J Radiat. Oncol Biol Phys. 53 (2002): 190-196
Neben, K. et al., Int. J Cancer 120 (2007): 1669-1677
Nebral, K. et al., Clinical Cancer Research 11 (2005): 6489-6494
Nibbe, R. K. et al., Mol. Cell Proteomics. 8 (2009): 827-845
Nieto, C. et al., J Cell Sci. 123 (2010): 2001-2007
Niikura, T. et al., Eur. J Neurosci. 17 (2003): 1150-1158
Nirde, P. et al., Oncogene 29 (2010): 117-127
Nonomura, N. et al., Br. J Cancer 97 (2007): 952-956
Noonan, E. J. et al., Cell Stress. Chaperones. 12 (2007): 219-229
Ohbayashi, N. et al., J Cell Sci. 125 (2012): 1508-1518
Ohiro, Y. et al., FEBS Lett. 524 (2002): 163-171
Onishi, H. et al., Cancer Lett. 371 (2016): 143-150
Orfanelli, U. et al., Oncogene 34 (2015): 2094-2102
Ostertag, E. M. et al., Annu. Rev Genet. 35 (2001): 501-538
Papadopoulos, C. et al., J Biol. Chem 286 (2011): 5494-5505
Park, H. J. et al., J Proteome. Res 7 (2008): 1138-1150
Peng, L. et al., Sci. Rep. 5 (2015): 13413
Penzo, M. et al., Oncotarget. 6 (2015): 21755-21760
Permuth-Wey, J. et al., Nat Commun. 4 (2013): 1627
Peters, U. et al., Gastroenterology 144 (2013): 799-807
Qian, J. et al., Proc. Natl. Acad. Sci. U.S.A 112 (2015a): 3469-3474
Qian, J. et al., Genom. Data 5 (2015b): 272-274
Rachel, R. A. et al., PLoS. ONE. 7 (2012): e42446
Ramana, C. V. et al., EMBO J 19 (2000): 263-272
Reis, A. et al., Nat Genet. 6 (1994): 174-179
Ribatti, D. et al., Int. J Exp. Pathol. 91 (2010): 350-356
Roe, 0. D. et al., Lung Cancer 67 (2010): 57-68
Rohde, M. et al., Genes Dev. 19 (2005): 570-582
Ruediger, R. et al., Oncogene 20 (2001): 1892-1899
Rusin, M. et al., Mol. Carcinog. 39 (2004): 155-163
Schiebel, E., Curr. Opin. Cell Biol 12 (2000): 113-118
Schmidt, F. et al., Aging (Albany. N.Y.) 7 (2015a): 527-528
Schmidt, F. et al., Oncotarget. 6 (2015b): 617-632
Schulz, E. G. et al., Immunity. 30 (2009): 673-683
Scieglinska, D. et al., J Cell Biochem. 104 (2008): 2193-2206
Sedlackova, L. et al., Tumour. Biol 32 (2011): 33-44
Sfar, S. et al., Hum. Immunol. 71 (2010): 377-382
Shain, A. H. et al., BMC. Genomics 14 (2013): 624
Sharma, P. et al., Biochem. Biophys. Res. Commun. 399 (2010): 129-132
Sherman, M., Ann. N.Y. Acad. Sci. 1197 (2010): 152-157
Simon, R. et al., Int J Cancer 107 (2003): 764-772
Singh, S. et al., Tumour. Biol 35 (2014): 12695-12706
Siragam, V. et al., PLoS. ONE. 9 (2014): e109128
Slepak, T. I. et al., Cytoskeleton (Hoboken.) 69 (2012): 514-527
Souza, A. P. et al., Cell Stress. Chaperones. 14 (2009): 301-310
Stawerski, P. et al., Contemp. Oncol (Pozn.) 17 (2013): 378-382
Szondy, K. et al., Cancer Invest 30 (2012): 317-322
Taira, N. et al., Mol. Cell 25 (2007): 725-738
Takahashi, M. et al., Gan To Kagaku Ryoho 24 (1997): 222-228
Takanami, I. et al., Cancer 88 (2000): 2686-2692
Tan, S. et al., Breast Cancer Res 16 (2014): R40
Tanis, T. et al., Arch. Oral Biol 59 (2014): 1155-1163
Toyoda, E. et al., J Biol. Chem. 283 (2008): 23711-23720
Van Aarsen, L. A. et al., Cancer Res. 68 (2008): 561-570
van den Boom, J. et al., Am. J Pathol. 163 (2003): 1033-1043
van den Heuvel, A. P. et al., Cancer Biol Ther. 13 (2012): 1185-1194
van, Wesenbeeck L. et al., J Bone Miner. Res 19 (2004): 183-189
Vargas, A. C. et al., Breast Cancer Res. Treat. 135 (2012): 153-165
Vargas-Roig, L. M. et al., Int. J Cancer 79 (1998): 468-475
von der, Heyde S. et al., PLoS. ONE. 10 (2015): e0117818
Vuletic, S. et al., Biochim. Biophys. Acta 1813 (2011): 1917-1924
Wang, Q. et al., Int. J Biol Sci. 10 (2014a): 807-816
Wang, T. et al., Clin Transl. Oncol 17 (2015): 564-569
Wang, W. M. et al., Zhongguo Shi Yan. Xue. Ye. Xue. Za Zhi. 22 (2014b): 1744-1747
Wang, X. et al., Clin Chim. Acta 417 (2013a): 73-79
Wang, X. M. et al., PLoS. ONE. 8 (2013b): e55714
Wang, X. X. et al., Hepatobiliary. Pancreat. Dis. Int. 12 (2013c): 540-545
Wang, X. X. et al., PLoS. ONE. 9 (2014c): e96501
Wang, Y. et al., Clin Chem. Lab Med. 48 (2010a): 1657-1663
Wang, Y. N. et al., Biochem. Biophys. Res Commun. 399 (2010b): 498-504
Wang, Z. et al., Med. Sci. Monit. 16 (2010c): CR357-CR364
Watson, P. J. et al., Traffic. 5 (2004): 79-88
Wehner, M. et al., FEBS J 277 (2010): 1597-1605
Weinacker, A. et al., J Biol. Chem 269 (1994): 6940-6948
Wu, D. et al., Mol. Med. Rep. 10 (2014): 2415-2420
Wu, M. et al., Oncogene 23 (2004): 6815-6819
Wu, X. S. et al., Proc. Natl. Acad. Sci. U.S.A 109 (2012): E2101-E2109

Xia, F. et al., Am. J Hum. Genet. 94 (2014): 784-789
Xia, L. M. et al., Zhonghua Gan Zang. Bing. Za Zhi. 16 (2008): 678-682
Xiang, Y. et al., J Clin Invest 125 (2015): 2293-2306
Xu, L. et al., Mol. Cell 10 (2002): 271-282
Xue, L. et al., Cell Physiol Biochem. 36 (2015): 1982-1990
Yamamoto, N. et al., Int. J Oncol 42 (2013): 1523-1532
Yang, D. et al., Cell Physiol Biochem. 27 (2011): 37-44
Yang, Z. et al., Int. J Med. Sci. 12 (2015): 256-263
Yau, C. et al., Breast Cancer Res 12 (2010): R85
Yokoyama, Y. et al., Mol. Med. Rep. 1 (2008): 197-201
Yongjun Zhang, M. M. et al., J Cancer Res Ther. 9 (2013): 660-663
Yu, D. et al., Oncotarget. 6 (2015): 7619-7631
Yu, H. et al., Nat Methods 8 (2011): 478-480
Yu, S. Y. et al., J Oral Pathol. Med. 43 (2014): 344-349
Zekri, A. R. et al., Asian Pac. J Cancer Prev. 16 (2015): 3543-3549
Zhang, W. et al., Tumori 100 (2014): 338-345
Zhao, Y. et al., Oncol Lett. 4 (2012): 755-758
Zhao-Yang, Z. et al., Cancer Lett. 266 (2008): 209-215
Zhou, J. R. et al., Zhonghua Er. Bi Yan. Hou Tou. Jing. Wai Ke. Za Zhi. 42 (2007): 934-938
Zhou, L. et al., FEBS Lett. 584 (2010): 3013-3020
Zhu, J. et al., J Pharmacol. Toxicol. Methods 76 (2015): 76-82

The invention claimed is:

1. A method of eliciting an immune response in a patient who has cancer overexpressing a MUC16 polypeptide comprising SEQ ID NO: 33, comprising administering to said patient a population of activated T cells that kill cancer cells, wherein the activated T cells are cytotoxic CD8+ T cells produced by contacting T cells with an antigen presenting cell that presents a peptide consisting of the amino acid sequence of SEQ ID NO: 33 in a complex with an MHC class I molecule on the surface of the antigen presenting cell in vitro, for a period of time sufficient to activate said T cell, wherein the cancer is lung cancer or gastric cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 5, wherein the expansion is in the presence of an anti-CD28 antibody and IL-12.

7. The method of claim 1, wherein the antigen presenting cell is infected with a recombinant virus expressing the peptide.

8. The method of claim 7, wherein the antigen presenting cell is a dendritic cell or a macrophage.

9. The method of claim 1, wherein the population of activated T cells are administered in the form of a composition.

10. The method of claim 9, wherein the composition further comprises an adjuvant.

11. The method of claim 10, wherein the adjuvant is selected from the group consisting of anti-CD40 antibody, imiquimod, resiquimod, GM-CSF, cyclophosphamide, Sunitinib, bevacizumab, interferon-alpha, interferon-beta, CpG oligonucleotides and derivatives, poly-(I:C) and derivatives, RNA, sildenafil, and particulate formations with poly(lactide coglycolide) (PLG), virosomes, interleukin (IL)-1, IL-2, IL-4, IL-7, IL-12, IL-13, IL-15, IL-21, and IL-23.

12. The method of claim 1, wherein the MEW molecule is HLA-A*24.

13. The method of claim 1, wherein the immune response is cytotoxic T cell response.

14. The method of claim 11, wherein the adjuvant comprises IL-2.

15. The method of claim 11, wherein the adjuvant comprises IL-7.

16. The method of claim 11, wherein the adjuvant comprises IL-12.

17. The method of claim 11, wherein the adjuvant comprises IL-15.

18. The method of claim 11, wherein the adjuvant comprises IL-21.

19. The method of claim 1, wherein the cancer is lung cancer.

20. The method of claim 1, wherein the cancer is gastric cancer.

* * * * *

SEQUENCE LISTING

```
<160> NUMBER OF SEQ ID NOS: 177

<210> SEQ ID NO 1
<211> LENGTH: 9
<212> TYPE: PRT
<213> ORGANISM: Homo sapiens

<400> SEQUENCE: 1

Lys Leu Leu Pro Tyr Ile Val Gly Val
1               5

<210> SEQ ID NO 2
<211> LENGTH: 9
<212> TYPE: PRT
<213> ORGANISM: Homo sapiens

<400> SEQUENCE: 2

Phe Leu Ile Pro Tyr Ala Ile Met Leu
1               5

<210> SEQ ID NO 3
<211> LENGTH: 9
<212> TYPE: PRT
<213> ORGANISM: Homo sapiens

<400> SEQUENCE: 3

Phe Leu Tyr Asp Val Val Lys Ser Leu
1               5

<210> SEQ ID NO 4
<211> LENGTH: 9
<212> TYPE: PRT
<213> ORGANISM: Homo sapiens

<400> SEQUENCE: 4

Phe Val Phe Ser Phe Pro Val Ser Val
1               5

<210> SEQ ID NO 5
<211> LENGTH: 9
<212> TYPE: PRT
<213> ORGANISM: Homo sapiens

<400> SEQUENCE: 5

Ala Leu Thr Ser Thr Leu Ile Ser Val
1               5

<210> SEQ ID NO 6
<211> LENGTH: 9
<212> TYPE: PRT
<213> ORGANISM: Homo sapiens
```

<400> SEQUENCE: 6

Ser Leu Gln Gly Ser Ile Met Thr Val
1               5

<210> SEQ ID NO 7
<211> LENGTH: 9
<212> TYPE: PRT
<213> ORGANISM: Homo sapiens

<400> SEQUENCE: 7

Asn Leu Leu Gln Val Leu Glu Lys Val
1               5

<210> SEQ ID NO 8
<211> LENGTH: 9
<212> TYPE: PRT
<213> ORGANISM: Homo sapiens

<400> SEQUENCE: 8

Ala Leu Leu Asn Ile Leu Ser Glu Val
1               5

<210> SEQ ID NO 9
<211> LENGTH: 9
<212> TYPE: PRT
<213> ORGANISM: Homo sapiens

<400> SEQUENCE: 9

Ala Leu Ser Gly Thr Leu Ser Gly Val
1               5

<210> SEQ ID NO 10
<211> LENGTH: 10
<212> TYPE: PRT
<213> ORGANISM: Homo sapiens

<400> SEQUENCE: 10

Lys Met Ala Gly Ile Gly Ile Arg Glu Ala
1               5                   10

<210> SEQ ID NO 11
<211> LENGTH: 9
<212> TYPE: PRT
<213> ORGANISM: Homo sapiens

<400> SEQUENCE: 11

Tyr Leu Asn Val Gln Val Lys Glu Leu
1               5

<210> SEQ ID NO 12
<211> LENGTH: 9
<212> TYPE: PRT
<213> ORGANISM: Homo sapiens

<400> SEQUENCE: 12

Ile Val Asp Arg Thr Thr Thr Val Val
1               5

<210> SEQ ID NO 13
<211> LENGTH: 9
<212> TYPE: PRT
<213> ORGANISM: Homo sapiens

<400> SEQUENCE: 13

```
Phe Leu Phe Asp Gly Ser Ala Asn Leu
1               5

<210> SEQ ID NO 14
<211> LENGTH: 9
<212> TYPE: PRT
<213> ORGANISM: Homo sapiens

<400> SEQUENCE: 14

Leu Ile Gln Asp Arg Val Ala Glu Val
1               5

<210> SEQ ID NO 15
<211> LENGTH: 9
<212> TYPE: PRT
<213> ORGANISM: Homo sapiens

<400> SEQUENCE: 15

Glu Leu Asp Arg Thr Pro Pro Glu Val
1               5

<210> SEQ ID NO 16
<211> LENGTH: 12
<212> TYPE: PRT
<213> ORGANISM: Homo sapiens

<400> SEQUENCE: 16

Leu Ile Phe Asp Leu Gly Gly Gly Thr Phe Asp Val
1               5                   10

<210> SEQ ID NO 17
<211> LENGTH: 11
<212> TYPE: PRT
<213> ORGANISM: Homo sapiens

<400> SEQUENCE: 17

Thr Leu Leu Gln Glu Gln Gly Thr Lys Thr Val
1               5                   10

<210> SEQ ID NO 18
<211> LENGTH: 9
<212> TYPE: PRT
<213> ORGANISM: Homo sapiens

<400> SEQUENCE: 18

Ile Leu Leu Thr Glu Gln Ile Asn Leu
1               5

<210> SEQ ID NO 19
<211> LENGTH: 9
<212> TYPE: PRT
<213> ORGANISM: Homo sapiens

<400> SEQUENCE: 19

Val Leu Thr Ser Asp Ser Pro Ala Leu
1               5

<210> SEQ ID NO 20
<211> LENGTH: 9
<212> TYPE: PRT
<213> ORGANISM: Homo sapiens

<400> SEQUENCE: 20

Leu Met Thr Lys Glu Ile Ser Ser Val
```

```
<210> SEQ ID NO 21
<211> LENGTH: 9
<212> TYPE: PRT
<213> ORGANISM: Homo sapiens

<400> SEQUENCE: 21

Val Leu Ser Ser Gly Leu Thr Ala Ala
1               5

<210> SEQ ID NO 22
<211> LENGTH: 9
<212> TYPE: PRT
<213> ORGANISM: Homo sapiens

<400> SEQUENCE: 22

Asn Leu Ile Asn Gln Glu Ile Met Leu
1               5

<210> SEQ ID NO 23
<211> LENGTH: 11
<212> TYPE: PRT
<213> ORGANISM: Homo sapiens

<400> SEQUENCE: 23

Val Tyr Thr Ser Trp Gln Ile Pro Gln Lys Phe
1               5                   10

<210> SEQ ID NO 24
<211> LENGTH: 9
<212> TYPE: PRT
<213> ORGANISM: Homo sapiens

<400> SEQUENCE: 24

Asn Tyr Pro Lys Ser Ile His Ser Phe
1               5

<210> SEQ ID NO 25
<211> LENGTH: 9
<212> TYPE: PRT
<213> ORGANISM: Homo sapiens

<400> SEQUENCE: 25

Arg Phe Met Asp Gly His Ile Thr Phe
1               5

<210> SEQ ID NO 26
<211> LENGTH: 9
<212> TYPE: PRT
<213> ORGANISM: Homo sapiens

<400> SEQUENCE: 26

Arg Tyr Leu Glu Lys Phe Tyr Gly Leu
1               5

<210> SEQ ID NO 27
<211> LENGTH: 9
<212> TYPE: PRT
<213> ORGANISM: Homo sapiens

<400> SEQUENCE: 27

Arg Tyr Pro Pro Pro Val Arg Glu Phe
1               5
```

```
<210> SEQ ID NO 28
<211> LENGTH: 11
<212> TYPE: PRT
<213> ORGANISM: Homo sapiens

<400> SEQUENCE: 28

Arg Tyr Leu Asp Ser Leu Lys Ala Ile Val Phe
1               5                   10

<210> SEQ ID NO 29
<211> LENGTH: 11
<212> TYPE: PRT
<213> ORGANISM: Homo sapiens

<400> SEQUENCE: 29

Tyr Tyr Thr Lys Gly Phe Ala Leu Leu Asn Phe
1               5                   10

<210> SEQ ID NO 30
<211> LENGTH: 9
<212> TYPE: PRT
<213> ORGANISM: Homo sapiens

<400> SEQUENCE: 30

Lys Tyr Leu Glu Lys Tyr Tyr Asn Leu
1               5

<210> SEQ ID NO 31
<211> LENGTH: 9
<212> TYPE: PRT
<213> ORGANISM: Homo sapiens

<400> SEQUENCE: 31

Ser Tyr Leu Asp Lys Val Arg Ala Leu
1               5

<210> SEQ ID NO 32
<211> LENGTH: 10
<212> TYPE: PRT
<213> ORGANISM: Homo sapiens

<400> SEQUENCE: 32

Glu Tyr Gln Pro Glu Met Leu Glu Lys Phe
1               5                   10

<210> SEQ ID NO 33
<211> LENGTH: 9
<212> TYPE: PRT
<213> ORGANISM: Homo sapiens

<400> SEQUENCE: 33

Thr Tyr Ser Glu Lys Thr Thr Leu Phe
1               5

<210> SEQ ID NO 34
<211> LENGTH: 10
<212> TYPE: PRT
<213> ORGANISM: Homo sapiens

<400> SEQUENCE: 34

Val Phe Met Lys Asp Gly Phe Phe Tyr Phe
1               5                   10

<210> SEQ ID NO 35
```

```
<211> LENGTH: 9
<212> TYPE: PRT
<213> ORGANISM: Homo sapiens

<400> SEQUENCE: 35

Thr Tyr Asn Pro Glu Ile Tyr Val Ile
1               5

<210> SEQ ID NO 36
<211> LENGTH: 9
<212> TYPE: PRT
<213> ORGANISM: Homo sapiens

<400> SEQUENCE: 36

Tyr Tyr Gly Asn Thr Leu Val Glu Phe
1               5

<210> SEQ ID NO 37
<211> LENGTH: 9
<212> TYPE: PRT
<213> ORGANISM: Homo sapiens

<400> SEQUENCE: 37

Arg Tyr Leu Glu Tyr Phe Glu Lys Ile
1               5

<210> SEQ ID NO 38
<211> LENGTH: 11
<212> TYPE: PRT
<213> ORGANISM: Homo sapiens

<400> SEQUENCE: 38

Val Phe Leu Asn Arg Ala Lys Ala Val Phe Phe
1               5                   10

<210> SEQ ID NO 39
<211> LENGTH: 10
<212> TYPE: PRT
<213> ORGANISM: Homo sapiens

<400> SEQUENCE: 39

Lys Phe Leu Glu His Thr Asn Phe Glu Phe
1               5                   10

<210> SEQ ID NO 40
<211> LENGTH: 11
<212> TYPE: PRT
<213> ORGANISM: Homo sapiens

<400> SEQUENCE: 40

Ile Tyr Asn Pro Ser Met Gly Val Ser Val Leu
1               5                   10

<210> SEQ ID NO 41
<211> LENGTH: 9
<212> TYPE: PRT
<213> ORGANISM: Homo sapiens

<400> SEQUENCE: 41

Thr Tyr Ile Gly Gln Gly Tyr Ile Ile
1               5

<210> SEQ ID NO 42
<211> LENGTH: 11
<212> TYPE: PRT
```

<213> ORGANISM: Homo sapiens

<400> SEQUENCE: 42

Val Tyr Val Thr Ile Asp Glu Asn Asn Ile Leu
1               5                   10

<210> SEQ ID NO 43
<211> LENGTH: 9
<212> TYPE: PRT
<213> ORGANISM: Homo sapiens

<400> SEQUENCE: 43

Arg Tyr Thr Leu His Ile Asn Thr Leu
1               5

<210> SEQ ID NO 44
<211> LENGTH: 9
<212> TYPE: PRT
<213> ORGANISM: Homo sapiens

<400> SEQUENCE: 44

Ile Tyr Asn Gln Ile Ala Glu Leu Trp
1               5

<210> SEQ ID NO 45
<211> LENGTH: 10
<212> TYPE: PRT
<213> ORGANISM: Homo sapiens

<400> SEQUENCE: 45

Lys Phe Leu Glu Ser Lys Gly Tyr Glu Phe
1               5                   10

<210> SEQ ID NO 46
<211> LENGTH: 11
<212> TYPE: PRT
<213> ORGANISM: Homo sapiens

<400> SEQUENCE: 46

Asn Tyr Thr Asn Gly Ser Phe Gly Ser Asn Phe
1               5                   10

<210> SEQ ID NO 47
<211> LENGTH: 11
<212> TYPE: PRT
<213> ORGANISM: Homo sapiens

<400> SEQUENCE: 47

Arg Tyr Ile Ser Pro Asp Gln Leu Ala Asp Leu
1               5                   10

<210> SEQ ID NO 48
<211> LENGTH: 10
<212> TYPE: PRT
<213> ORGANISM: Homo sapiens

<400> SEQUENCE: 48

Tyr Tyr Tyr Gly Asn Thr Leu Val Glu Phe
1               5                   10

<210> SEQ ID NO 49
<211> LENGTH: 10
<212> TYPE: PRT
<213> ORGANISM: Homo sapiens

<400> SEQUENCE: 49

Gln Tyr Leu Phe Pro Ser Phe Glu Thr Phe
1               5                   10

<210> SEQ ID NO 50
<211> LENGTH: 11
<212> TYPE: PRT
<213> ORGANISM: Homo sapiens

<400> SEQUENCE: 50

Leu Tyr Ile Gly Trp Asp Lys His Tyr Gly Phe
1               5                   10

<210> SEQ ID NO 51
<211> LENGTH: 10
<212> TYPE: PRT
<213> ORGANISM: Homo sapiens

<400> SEQUENCE: 51

Asn Tyr Leu Leu Glu Ser Pro His Arg Phe
1               5                   10

<210> SEQ ID NO 52
<211> LENGTH: 11
<212> TYPE: PRT
<213> ORGANISM: Homo sapiens

<400> SEQUENCE: 52

Ser Tyr Met Glu Val Pro Thr Tyr Leu Asn Phe
1               5                   10

<210> SEQ ID NO 53
<211> LENGTH: 9
<212> TYPE: PRT
<213> ORGANISM: Homo sapiens

<400> SEQUENCE: 53

Ile Tyr Ala Gly Gln Trp Asn Asp Phe
1               5

<210> SEQ ID NO 54
<211> LENGTH: 10
<212> TYPE: PRT
<213> ORGANISM: Homo sapiens

<400> SEQUENCE: 54

Ala Tyr Lys Asp Lys Asp Ile Ser Phe Phe
1               5                   10

<210> SEQ ID NO 55
<211> LENGTH: 10
<212> TYPE: PRT
<213> ORGANISM: Homo sapiens

<400> SEQUENCE: 55

Ile Tyr Pro Val Lys Tyr Thr Gln Thr Phe
1               5                   10

<210> SEQ ID NO 56
<211> LENGTH: 10
<212> TYPE: PRT
<213> ORGANISM: Homo sapiens

<400> SEQUENCE: 56

Arg Tyr Phe Pro Thr Gln Ala Leu Asn Phe
1               5                   10

<210> SEQ ID NO 57
<211> LENGTH: 9
<212> TYPE: PRT
<213> ORGANISM: Homo sapiens

<400> SEQUENCE: 57

Ser Tyr Ser Ile Gly Ile Ala Asn Phe
1               5

<210> SEQ ID NO 58
<211> LENGTH: 13
<212> TYPE: PRT
<213> ORGANISM: Homo sapiens

<400> SEQUENCE: 58

Val Tyr Phe Lys Pro Ser Leu Thr Pro Ser Gly Glu Phe
1               5                   10

<210> SEQ ID NO 59
<211> LENGTH: 9
<212> TYPE: PRT
<213> ORGANISM: Homo sapiens

<400> SEQUENCE: 59

His Tyr Phe Asn Thr Pro Phe Gln Leu
1               5

<210> SEQ ID NO 60
<211> LENGTH: 9
<212> TYPE: PRT
<213> ORGANISM: Homo sapiens

<400> SEQUENCE: 60

Ser Tyr Pro Ala Lys Leu Ser Phe Ile
1               5

<210> SEQ ID NO 61
<211> LENGTH: 9
<212> TYPE: PRT
<213> ORGANISM: Homo sapiens

<400> SEQUENCE: 61

Arg Tyr Gly Ser Pro Ile Asn Thr Phe
1               5

<210> SEQ ID NO 62
<211> LENGTH: 9
<212> TYPE: PRT
<213> ORGANISM: Homo sapiens

<400> SEQUENCE: 62

Ala Tyr Lys Pro Gly Ala Leu Thr Phe
1               5

<210> SEQ ID NO 63
<211> LENGTH: 9
<212> TYPE: PRT
<213> ORGANISM: Homo sapiens

<400> SEQUENCE: 63

Leu Tyr Ile Asn Lys Ala Asn Ile Trp
1               5

<210> SEQ ID NO 64
<211> LENGTH: 9
<212> TYPE: PRT
<213> ORGANISM: Homo sapiens

<400> SEQUENCE: 64

Val Tyr Pro Leu Ala Leu Tyr Gly Phe
1               5

<210> SEQ ID NO 65
<211> LENGTH: 9
<212> TYPE: PRT
<213> ORGANISM: Homo sapiens

<400> SEQUENCE: 65

Ile Tyr Gln Arg Trp Lys Asp Leu Leu
1               5

<210> SEQ ID NO 66
<211> LENGTH: 9
<212> TYPE: PRT
<213> ORGANISM: Homo sapiens

<400> SEQUENCE: 66

Asp Tyr Ile Pro Gln Leu Ala Lys Phe
1               5

<210> SEQ ID NO 67
<211> LENGTH: 12
<212> TYPE: PRT
<213> ORGANISM: Homo sapiens

<400> SEQUENCE: 67

Ile Phe Leu Asp Tyr Glu Ala Gly His Leu Ser Phe
1               5                   10

<210> SEQ ID NO 68
<211> LENGTH: 9
<212> TYPE: PRT
<213> ORGANISM: Homo sapiens

<400> SEQUENCE: 68

Arg Tyr Leu Phe Val Val Asp Arg Leu
1               5

<210> SEQ ID NO 69
<211> LENGTH: 11
<212> TYPE: PRT
<213> ORGANISM: Homo sapiens

<400> SEQUENCE: 69

Thr Tyr Ala Ala Leu Asn Ser Lys Ala Thr Phe
1               5                   10

<210> SEQ ID NO 70
<211> LENGTH: 9
<212> TYPE: PRT
<213> ORGANISM: Homo sapiens

<400> SEQUENCE: 70

Val Tyr His Ser Tyr Leu Thr Ile Phe
1               5

```
<210> SEQ ID NO 71
<211> LENGTH: 9
<212> TYPE: PRT
<213> ORGANISM: Homo sapiens

<400> SEQUENCE: 71

Thr Tyr Leu Thr Asn His Leu Arg Leu
1               5

<210> SEQ ID NO 72
<211> LENGTH: 10
<212> TYPE: PRT
<213> ORGANISM: Homo sapiens

<400> SEQUENCE: 72

Tyr Tyr Val Asp Lys Leu Phe Asn Thr Ile
1               5                   10

<210> SEQ ID NO 73
<211> LENGTH: 10
<212> TYPE: PRT
<213> ORGANISM: Homo sapiens

<400> SEQUENCE: 73

Arg Tyr Leu His Val Glu Gly Gly Asn Phe
1               5                   10

<210> SEQ ID NO 74
<211> LENGTH: 10
<212> TYPE: PRT
<213> ORGANISM: Homo sapiens

<400> SEQUENCE: 74

Glu Tyr Leu Pro Glu Phe Leu His Thr Phe
1               5                   10

<210> SEQ ID NO 75
<211> LENGTH: 12
<212> TYPE: PRT
<213> ORGANISM: Homo sapiens

<400> SEQUENCE: 75

Ala Tyr Pro Asp Leu Asn Glu Ile Tyr Arg Ser Phe
1               5                   10

<210> SEQ ID NO 76
<211> LENGTH: 9
<212> TYPE: PRT
<213> ORGANISM: Homo sapiens

<400> SEQUENCE: 76

Val Tyr Thr Glx Ile Gln Ser Arg Phe
1               5

<210> SEQ ID NO 77
<211> LENGTH: 12
<212> TYPE: PRT
<213> ORGANISM: Homo sapiens

<400> SEQUENCE: 77

Arg Tyr Leu Glu Ala Gly Ala Ala Gly Leu Arg Trp
1               5                   10

<210> SEQ ID NO 78
<211> LENGTH: 9
```

```
<212> TYPE: PRT
<213> ORGANISM: Homo sapiens

<400> SEQUENCE: 78

Ile Tyr Thr Arg Val Thr Tyr Tyr Leu
1               5

<210> SEQ ID NO 79
<211> LENGTH: 9
<212> TYPE: PRT
<213> ORGANISM: Homo sapiens

<400> SEQUENCE: 79

Arg Tyr Gly Gly Ser Phe Ala Glu Leu
1               5

<210> SEQ ID NO 80
<211> LENGTH: 9
<212> TYPE: PRT
<213> ORGANISM: Homo sapiens

<400> SEQUENCE: 80

Ala Tyr Leu Lys Glu Val Glu Gln Leu
1               5

<210> SEQ ID NO 81
<211> LENGTH: 9
<212> TYPE: PRT
<213> ORGANISM: Homo sapiens

<400> SEQUENCE: 81

Lys Tyr Ile Glu Ala Ile Gln Trp Ile
1               5

<210> SEQ ID NO 82
<211> LENGTH: 9
<212> TYPE: PRT
<213> ORGANISM: Homo sapiens

<400> SEQUENCE: 82

Phe Tyr Gln Gly Ile Val Gln Gln Phe
1               5

<210> SEQ ID NO 83
<211> LENGTH: 11
<212> TYPE: PRT
<213> ORGANISM: Homo sapiens

<400> SEQUENCE: 83

Glu Tyr Ser Asp Val Leu Ala Lys Leu Ala Phe
1               5                   10

<210> SEQ ID NO 84
<211> LENGTH: 11
<212> TYPE: PRT
<213> ORGANISM: Homo sapiens

<400> SEQUENCE: 84

Thr Phe Asp Val Ala Pro Ser Arg Leu Asp Phe
1               5                   10

<210> SEQ ID NO 85
<211> LENGTH: 9
<212> TYPE: PRT
<213> ORGANISM: Homo sapiens
```

<400> SEQUENCE: 85

Pro Phe Leu Gln Ala Ser Pro His Phe
1               5

<210> SEQ ID NO 86
<211> LENGTH: 17
<212> TYPE: PRT
<213> ORGANISM: Homo sapiens

<400> SEQUENCE: 86

Leu Ser Ala Asp Asp Ile Arg Gly Ile Gln Ser Leu Tyr Gly Asp Pro
1               5                   10                  15

Lys

<210> SEQ ID NO 87
<211> LENGTH: 19
<212> TYPE: PRT
<213> ORGANISM: Homo sapiens

<400> SEQUENCE: 87

Glu Gly Asp Ile Gln Gln Phe Leu Ile Thr Gly Asp Pro Lys Ala Ala
1               5                   10                  15

Tyr Asp Tyr

<210> SEQ ID NO 88
<211> LENGTH: 17
<212> TYPE: PRT
<213> ORGANISM: Homo sapiens

<400> SEQUENCE: 88

Asn Pro Val Ser Gln Val Glu Ile Leu Lys Asn Lys Pro Leu Ser Val
1               5                   10                  15

Gly

<210> SEQ ID NO 89
<211> LENGTH: 14
<212> TYPE: PRT
<213> ORGANISM: Homo sapiens

<400> SEQUENCE: 89

Lys Leu Tyr Ile Gly Asn Leu Ser Glu Asn Ala Ala Pro Ser
1               5                   10

<210> SEQ ID NO 90
<211> LENGTH: 16
<212> TYPE: PRT
<213> ORGANISM: Homo sapiens

<400> SEQUENCE: 90

Asp Ala Val Gln Met Val Ile Thr Glu Ala Gln Lys Val Asp Thr Arg
1               5                   10                  15

<210> SEQ ID NO 91
<211> LENGTH: 18
<212> TYPE: PRT
<213> ORGANISM: Homo sapiens

<400> SEQUENCE: 91

Val Ala Arg Leu Pro Ile Ile Asp Leu Ala Pro Val Asp Val Gly Gly
1               5                   10                  15

Thr Asp

<210> SEQ ID NO 92
<211> LENGTH: 20
<212> TYPE: PRT
<213> ORGANISM: Homo sapiens

<400> SEQUENCE: 92

Asn Lys Pro Ser Arg Leu Pro Phe Leu Asp Ile Ala Pro Leu Asp Ile
1               5                   10                  15

Gly Gly Ala Asp
            20

<210> SEQ ID NO 93
<211> LENGTH: 18
<212> TYPE: PRT
<213> ORGANISM: Homo sapiens

<400> SEQUENCE: 93

Ser Arg Pro Gln Ala Pro Ile Thr Gly Tyr Arg Ile Val Tyr Ser Pro
1               5                   10                  15

Ser Val

<210> SEQ ID NO 94
<211> LENGTH: 9
<212> TYPE: PRT
<213> ORGANISM: Homo sapiens

<400> SEQUENCE: 94

Ile Leu Val Asp Trp Leu Val Gln Val
1               5

<210> SEQ ID NO 95
<211> LENGTH: 9
<212> TYPE: PRT
<213> ORGANISM: Homo sapiens

<400> SEQUENCE: 95

Lys Ile Ile Gly Ile Met Glu Glu Val
1               5

<210> SEQ ID NO 96
<211> LENGTH: 9
<212> TYPE: PRT
<213> ORGANISM: Homo sapiens

<400> SEQUENCE: 96

Ala Met Gly Ile Ala Pro Pro Lys Val
1               5

<210> SEQ ID NO 97
<211> LENGTH: 9
<212> TYPE: PRT
<213> ORGANISM: Homo sapiens

<400> SEQUENCE: 97

Thr Leu Phe Pro Val Arg Leu Leu Val
1               5

<210> SEQ ID NO 98
<211> LENGTH: 10
<212> TYPE: PRT
<213> ORGANISM: Homo sapiens

<400> SEQUENCE: 98

```
Val Leu Tyr Pro His Glu Pro Thr Ala Val
1               5                   10

<210> SEQ ID NO 99
<211> LENGTH: 9
<212> TYPE: PRT
<213> ORGANISM: Homo sapiens

<400> SEQUENCE: 99

Ala Leu Phe Gln Arg Pro Pro Leu Ile
1               5

<210> SEQ ID NO 100
<211> LENGTH: 9
<212> TYPE: PRT
<213> ORGANISM: Homo sapiens

<400> SEQUENCE: 100

Lys Ile Val Asp Phe Ser Tyr Ser Val
1               5

<210> SEQ ID NO 101
<211> LENGTH: 9
<212> TYPE: PRT
<213> ORGANISM: Homo sapiens

<400> SEQUENCE: 101

Leu Leu Leu Glu Ile Leu His Glu Ile
1               5

<210> SEQ ID NO 102
<211> LENGTH: 9
<212> TYPE: PRT
<213> ORGANISM: Homo sapiens

<400> SEQUENCE: 102

Ser Leu Leu Ser Glu Leu Gln His Ala
1               5

<210> SEQ ID NO 103
<211> LENGTH: 10
<212> TYPE: PRT
<213> ORGANISM: Homo sapiens

<400> SEQUENCE: 103

Lys Leu Leu Ser Asp Pro Asn Tyr Gly Val
1               5                   10

<210> SEQ ID NO 104
<211> LENGTH: 10
<212> TYPE: PRT
<213> ORGANISM: Homo sapiens

<400> SEQUENCE: 104

Ser Leu Val Ala Val Glu Leu Glu Lys Val
1               5                   10

<210> SEQ ID NO 105
<211> LENGTH: 9
<212> TYPE: PRT
<213> ORGANISM: Homo sapiens

<400> SEQUENCE: 105

Ile Val Ala Glu Ser Leu Gln Gln Val
```

```
1               5
```

<210> SEQ ID NO 106
<211> LENGTH: 9
<212> TYPE: PRT
<213> ORGANISM: Homo sapiens

<400> SEQUENCE: 106

```
Ser Ile Leu Glu His Gln Ile Gln Val
1               5
```

<210> SEQ ID NO 107
<211> LENGTH: 9
<212> TYPE: PRT
<213> ORGANISM: Homo sapiens

<400> SEQUENCE: 107

```
Ala Leu Ser Glu Arg Ala Val Ala Val
1               5
```

<210> SEQ ID NO 108
<211> LENGTH: 9
<212> TYPE: PRT
<213> ORGANISM: Homo sapiens

<400> SEQUENCE: 108

```
Thr Leu Leu Asp Phe Ile Asn Ala Val
1               5
```

<210> SEQ ID NO 109
<211> LENGTH: 9
<212> TYPE: PRT
<213> ORGANISM: Homo sapiens

<400> SEQUENCE: 109

```
Asn Leu Ile Glu Val Asn Glu Glu Val
1               5
```

<210> SEQ ID NO 110
<211> LENGTH: 15
<212> TYPE: PRT
<213> ORGANISM: Homo sapiens

<400> SEQUENCE: 110

```
Ile Gln Leu Ile Val Gln Asp Lys Glu Ser Val Phe Ser Pro Arg
1               5                   10                  15
```

<210> SEQ ID NO 111
<211> LENGTH: 9
<212> TYPE: PRT
<213> ORGANISM: Homo sapiens

<400> SEQUENCE: 111

```
Ser Leu Tyr Lys Gly Leu Leu Ser Val
1               5
```

<210> SEQ ID NO 112
<211> LENGTH: 9
<212> TYPE: PRT
<213> ORGANISM: Homo sapiens

<400> SEQUENCE: 112

```
Val Leu Ala Pro Leu Phe Val Tyr Leu
1               5
```

<210> SEQ ID NO 113
<211> LENGTH: 9
<212> TYPE: PRT
<213> ORGANISM: Homo sapiens

<400> SEQUENCE: 113

Phe Leu Leu Asp Gly Ser Ala Asn Val
1               5

<210> SEQ ID NO 114
<211> LENGTH: 9
<212> TYPE: PRT
<213> ORGANISM: Homo sapiens

<400> SEQUENCE: 114

Ala Met Ser Ser Lys Phe Phe Leu Val
1               5

<210> SEQ ID NO 115
<211> LENGTH: 9
<212> TYPE: PRT
<213> ORGANISM: Homo sapiens

<400> SEQUENCE: 115

Tyr Val Tyr Gln Asn Asn Ile Tyr Leu
1               5

<210> SEQ ID NO 116
<211> LENGTH: 9
<212> TYPE: PRT
<213> ORGANISM: Homo sapiens

<400> SEQUENCE: 116

Lys Ile Gln Glu Met Gln His Phe Leu
1               5

<210> SEQ ID NO 117
<211> LENGTH: 9
<212> TYPE: PRT
<213> ORGANISM: Homo sapiens

<400> SEQUENCE: 117

Ile Leu Ile Asp Trp Leu Val Gln Val
1               5

<210> SEQ ID NO 118
<211> LENGTH: 9
<212> TYPE: PRT
<213> ORGANISM: Homo sapiens

<400> SEQUENCE: 118

Ser Leu His Phe Leu Ile Leu Tyr Val
1               5

<210> SEQ ID NO 119
<211> LENGTH: 9
<212> TYPE: PRT
<213> ORGANISM: Homo sapiens

<400> SEQUENCE: 119

Ile Val Asp Asp Ile Thr Tyr Asn Val
1               5

<210> SEQ ID NO 120

```
<211> LENGTH: 9
<212> TYPE: PRT
<213> ORGANISM: Homo sapiens

<400> SEQUENCE: 120

Lys Ile Gln Glu Ile Leu Thr Gln Val
1               5

<210> SEQ ID NO 121
<211> LENGTH: 9
<212> TYPE: PRT
<213> ORGANISM: Homo sapiens

<400> SEQUENCE: 121

Arg Leu Leu Asp Ser Val Ser Arg Leu
1               5

<210> SEQ ID NO 122
<211> LENGTH: 9
<212> TYPE: PRT
<213> ORGANISM: Homo sapiens

<400> SEQUENCE: 122

Lys Leu Ser Trp Asp Leu Ile Tyr Leu
1               5

<210> SEQ ID NO 123
<211> LENGTH: 9
<212> TYPE: PRT
<213> ORGANISM: Homo sapiens

<400> SEQUENCE: 123

Gly Leu Thr Asp Asn Ile His Leu Val
1               5

<210> SEQ ID NO 124
<211> LENGTH: 9
<212> TYPE: PRT
<213> ORGANISM: Homo sapiens

<400> SEQUENCE: 124

Asn Leu Leu Asp Leu Asp Tyr Glu Leu
1               5

<210> SEQ ID NO 125
<211> LENGTH: 9
<212> TYPE: PRT
<213> ORGANISM: Homo sapiens

<400> SEQUENCE: 125

Arg Leu Asp Asp Leu Lys Met Thr Val
1               5

<210> SEQ ID NO 126
<211> LENGTH: 9
<212> TYPE: PRT
<213> ORGANISM: Homo sapiens

<400> SEQUENCE: 126

Lys Leu Leu Thr Glu Val His Ala Ala
1               5

<210> SEQ ID NO 127
<211> LENGTH: 10
<212> TYPE: PRT
```

<213> ORGANISM: Homo sapiens

<400> SEQUENCE: 127

Ile Leu Phe Pro Asp Ile Ile Ala Arg Ala
1               5                   10

<210> SEQ ID NO 128
<211> LENGTH: 9
<212> TYPE: PRT
<213> ORGANISM: Homo sapiens

<400> SEQUENCE: 128

Thr Leu Ser Ser Ile Lys Val Glu Val
1               5

<210> SEQ ID NO 129
<211> LENGTH: 9
<212> TYPE: PRT
<213> ORGANISM: Homo sapiens

<400> SEQUENCE: 129

Gly Leu Ile Glu Ile Ile Ser Asn Ala
1               5

<210> SEQ ID NO 130
<211> LENGTH: 9
<212> TYPE: PRT
<213> ORGANISM: Homo sapiens

<400> SEQUENCE: 130

Lys Ile Leu Glu Asp Val Val Gly Val
1               5

<210> SEQ ID NO 131
<211> LENGTH: 9
<212> TYPE: PRT
<213> ORGANISM: Homo sapiens

<400> SEQUENCE: 131

Ala Leu Val Gln Asp Leu Ala Lys Ala
1               5

<210> SEQ ID NO 132
<211> LENGTH: 10
<212> TYPE: PRT
<213> ORGANISM: Homo sapiens

<400> SEQUENCE: 132

Ala Leu Phe Val Arg Leu Leu Ala Leu Ala
1               5                   10

<210> SEQ ID NO 133
<211> LENGTH: 9
<212> TYPE: PRT
<213> ORGANISM: Homo sapiens

<400> SEQUENCE: 133

Arg Leu Ala Ser Tyr Leu Asp Lys Val
1               5

<210> SEQ ID NO 134
<211> LENGTH: 9
<212> TYPE: PRT
<213> ORGANISM: Homo sapiens -continued

```
<400> SEQUENCE: 134

Thr Leu Trp Tyr Arg Ala Pro Glu Val
1               5

<210> SEQ ID NO 135
<211> LENGTH: 9
<212> TYPE: PRT
<213> ORGANISM: Homo sapiens

<400> SEQUENCE: 135

Ala Ile Asp Gly Asn Asn His Glu Val
1               5

<210> SEQ ID NO 136
<211> LENGTH: 9
<212> TYPE: PRT
<213> ORGANISM: Homo sapiens

<400> SEQUENCE: 136

Ala Leu Val Asp His Thr Pro Tyr Leu
1               5

<210> SEQ ID NO 137
<211> LENGTH: 9
<212> TYPE: PRT
<213> ORGANISM: Homo sapiens

<400> SEQUENCE: 137

Phe Leu Val Asp Gly Ser Trp Ser Val
1               5

<210> SEQ ID NO 138
<211> LENGTH: 11
<212> TYPE: PRT
<213> ORGANISM: Homo sapiens

<400> SEQUENCE: 138

Ala Leu Asn Glu Glu Ala Gly Arg Leu Leu Leu
1               5                   10

<210> SEQ ID NO 139
<211> LENGTH: 9
<212> TYPE: PRT
<213> ORGANISM: Homo sapiens

<400> SEQUENCE: 139

Ser Leu Ile Glu Asp Leu Ile Leu Leu
1               5

<210> SEQ ID NO 140
<211> LENGTH: 9
<212> TYPE: PRT
<213> ORGANISM: Homo sapiens

<400> SEQUENCE: 140

Thr Leu Tyr Pro His Thr Ser Gln Val
1               5

<210> SEQ ID NO 141
<211> LENGTH: 9
<212> TYPE: PRT
<213> ORGANISM: Homo sapiens

<400> SEQUENCE: 141
```

```
Asn Leu Ile Glu Lys Ser Ile Tyr Leu
1               5
```

<210> SEQ ID NO 142
<211> LENGTH: 12
<212> TYPE: PRT
<213> ORGANISM: Homo sapiens

<400> SEQUENCE: 142

```
Val Leu Leu Pro Val Glu Val Ala Thr His Tyr Leu
1               5                   10
```

<210> SEQ ID NO 143
<211> LENGTH: 9
<212> TYPE: PRT
<213> ORGANISM: Homo sapiens

<400> SEQUENCE: 143

```
Ala Ile Val Asp Lys Val Pro Ser Val
1               5
```

<210> SEQ ID NO 144
<211> LENGTH: 10
<212> TYPE: PRT
<213> ORGANISM: Homo sapiens

<400> SEQUENCE: 144

```
Lys Ile Phe Asp Glu Ile Leu Val Asn Ala
1               5                   10
```

<210> SEQ ID NO 145
<211> LENGTH: 9
<212> TYPE: PRT
<213> ORGANISM: Homo sapiens

<400> SEQUENCE: 145

```
Ala Met Thr Gln Leu Leu Ala Gly Val
1               5
```

<210> SEQ ID NO 146
<211> LENGTH: 9
<212> TYPE: PRT
<213> ORGANISM: Homo sapiens

<400> SEQUENCE: 146

```
Phe Gln Tyr Asp His Glu Ala Phe Leu
1               5
```

<210> SEQ ID NO 147
<211> LENGTH: 9
<212> TYPE: PRT
<213> ORGANISM: Homo sapiens

<400> SEQUENCE: 147

```
Val Leu Phe Pro Asn Leu Lys Thr Val
1               5
```

<210> SEQ ID NO 148
<211> LENGTH: 9
<212> TYPE: PRT
<213> ORGANISM: Homo sapiens

<400> SEQUENCE: 148

```
Ala Leu Phe Gly Ala Leu Phe Leu Ala
1               5
```

```
<210> SEQ ID NO 149
<211> LENGTH: 10
<212> TYPE: PRT
<213> ORGANISM: Homo sapiens

<400> SEQUENCE: 149

Lys Leu Val Glu Phe Asp Phe Leu Gly Ala
1               5                   10

<210> SEQ ID NO 150
<211> LENGTH: 9
<212> TYPE: PRT
<213> ORGANISM: Homo sapiens

<400> SEQUENCE: 150

Gly Val Leu Glu Asn Ile Phe Gly Val
1               5

<210> SEQ ID NO 151
<211> LENGTH: 9
<212> TYPE: PRT
<213> ORGANISM: Homo sapiens

<400> SEQUENCE: 151

Ala Val Val Glu Phe Leu Thr Ser Val
1               5

<210> SEQ ID NO 152
<211> LENGTH: 9
<212> TYPE: PRT
<213> ORGANISM: Homo sapiens

<400> SEQUENCE: 152

Ile Leu Gln Asp Arg Leu Asn Gln Val
1               5

<210> SEQ ID NO 153
<211> LENGTH: 9
<212> TYPE: PRT
<213> ORGANISM: Homo sapiens

<400> SEQUENCE: 153

Ala Leu Tyr Asp Ser Val Ile Leu Leu
1               5

<210> SEQ ID NO 154
<211> LENGTH: 9
<212> TYPE: PRT
<213> ORGANISM: Homo sapiens

<400> SEQUENCE: 154

Ile Leu Phe Glu Ile Asn Pro Lys Leu
1               5

<210> SEQ ID NO 155
<211> LENGTH: 9
<212> TYPE: PRT
<213> ORGANISM: Homo sapiens

<400> SEQUENCE: 155

Ala Leu Asp Glu Asn Leu His Gln Leu
1               5
```

```
<210> SEQ ID NO 156
<211> LENGTH: 9
<212> TYPE: PRT
<213> ORGANISM: Homo sapiens

<400> SEQUENCE: 156

Thr Val Ala Glu Val Ile Gln Ser Val
1               5

<210> SEQ ID NO 157
<211> LENGTH: 9
<212> TYPE: PRT
<213> ORGANISM: Homo sapiens

<400> SEQUENCE: 157

Lys Leu Phe Gly Glu Lys Thr Tyr Leu
1               5

<210> SEQ ID NO 158
<211> LENGTH: 9
<212> TYPE: PRT
<213> ORGANISM: Homo sapiens

<400> SEQUENCE: 158

Lys Leu Asp Glu Thr Asn Asn Thr Leu
1               5

<210> SEQ ID NO 159
<211> LENGTH: 10
<212> TYPE: PRT
<213> ORGANISM: Homo sapiens

<400> SEQUENCE: 159

Thr Tyr Lys Tyr Val Asp Ile Asn Thr Phe
1               5                   10

<210> SEQ ID NO 160
<211> LENGTH: 9
<212> TYPE: PRT
<213> ORGANISM: Homo sapiens

<400> SEQUENCE: 160

Ser Tyr Leu Gln Ala Ala Asn Ala Leu
1               5

<210> SEQ ID NO 161
<211> LENGTH: 10
<212> TYPE: PRT
<213> ORGANISM: Homo sapiens

<400> SEQUENCE: 161

Leu Tyr Gln Ile Leu Gln Gly Ile Val Phe
1               5                   10

<210> SEQ ID NO 162
<211> LENGTH: 17
<212> TYPE: PRT
<213> ORGANISM: Homo sapiens

<400> SEQUENCE: 162

Thr Asn Gly Val Ile His Val Val Asp Lys Leu Leu Tyr Pro Ala Asp
1               5                   10                  15

Thr
```

```
<210> SEQ ID NO 163
<211> LENGTH: 10
<212> TYPE: PRT
<213> ORGANISM: Homo sapiens

<400> SEQUENCE: 163

Glu Leu Ala Gly Ile Gly Ile Leu Thr Val
1               5                   10

<210> SEQ ID NO 164
<211> LENGTH: 9
<212> TYPE: PRT
<213> ORGANISM: Homo sapiens

<400> SEQUENCE: 164

Tyr Leu Leu Pro Ala Ile Val His Ile
1               5

<210> SEQ ID NO 165
<211> LENGTH: 15
<212> TYPE: PRT
<213> ORGANISM: Homo sapiens

<400> SEQUENCE: 165

Thr Leu Gly Glu Phe Leu Lys Leu Asp Arg Glu Arg Ala Lys Asn
1               5                   10                  15

<210> SEQ ID NO 166
<211> LENGTH: 17
<212> TYPE: PRT
<213> ORGANISM: Homo sapiens

<400> SEQUENCE: 166

Thr Phe Ser Tyr Val Asp Pro Val Ile Thr Ser Ile Ser Pro Lys Tyr
1               5                   10                  15

Gly

<210> SEQ ID NO 167
<211> LENGTH: 16
<212> TYPE: PRT
<213> ORGANISM: Homo sapiens

<400> SEQUENCE: 167

Ser Gln Asp Asp Ile Lys Gly Ile Gln Lys Leu Tyr Gly Lys Arg Ser
1               5                   10                  15

<210> SEQ ID NO 168
<211> LENGTH: 16
<212> TYPE: PRT
<213> ORGANISM: Homo sapiens

<400> SEQUENCE: 168

Ser Pro Gln Tyr Ser Trp Arg Ile Asn Gly Ile Pro Gln Gln His Thr
1               5                   10                  15

<210> SEQ ID NO 169
<211> LENGTH: 15
<212> TYPE: PRT
<213> ORGANISM: Homo sapiens

<400> SEQUENCE: 169

Thr Pro Pro Ile Asp Ala His Thr Arg Asn Leu Leu Arg Asn His
1               5                   10                  15
```

-continued

```
<210> SEQ ID NO 170
<211> LENGTH: 15
<212> TYPE: PRT
<213> ORGANISM: Homo sapiens

<400> SEQUENCE: 170

Lys Ile Phe Tyr Val Tyr Met Lys Arg Lys Tyr Glu Ala Met Thr
1               5                   10                  15

<210> SEQ ID NO 171
<211> LENGTH: 15
<212> TYPE: PRT
<213> ORGANISM: Homo sapiens

<400> SEQUENCE: 171

Arg Lys Val Ala Glu Leu Val His Phe Leu Leu Leu Lys Tyr Arg
1               5                   10                  15

<210> SEQ ID NO 172
<211> LENGTH: 15
<212> TYPE: PRT
<213> ORGANISM: Homo sapiens

<400> SEQUENCE: 172

Phe Phe Pro Val Ile Phe Ser Lys Ala Ser Ser Ser Leu Gln Leu
1               5                   10                  15

<210> SEQ ID NO 173
<211> LENGTH: 15
<212> TYPE: PRT
<213> ORGANISM: Homo sapiens

<400> SEQUENCE: 173

Gly Asp Asn Gln Ile Met Pro Lys Ala Gly Leu Leu Ile Ile Val
1               5                   10                  15

<210> SEQ ID NO 174
<211> LENGTH: 15
<212> TYPE: PRT
<213> ORGANISM: Homo sapiens

<400> SEQUENCE: 174

Thr Ser Tyr Val Lys Val Leu His His Met Val Lys Ile Ser Gly
1               5                   10                  15

<210> SEQ ID NO 175
<211> LENGTH: 18
<212> TYPE: PRT
<213> ORGANISM: Homo sapiens

<400> SEQUENCE: 175

Val Leu Leu Lys Glu Phe Thr Val Ser Gly Asn Ile Leu Thr Ile Arg
1               5                   10                  15

Leu Thr

<210> SEQ ID NO 176
<211> LENGTH: 17
<212> TYPE: PRT
<213> ORGANISM: Homo sapiens

<400> SEQUENCE: 176

Lys Val Pro Ile Lys Trp Met Ala Leu Glu Ser Ile Leu Arg Arg Arg
1               5                   10                  15

Phe
```

```
<210> SEQ ID NO 177
<211> LENGTH: 13
<212> TYPE: PRT
<213> ORGANISM: Homo sapiens

<400> SEQUENCE: 177

Ala Lys Ala Val Ala Ala Trp Thr Leu Lys Ala Ala Ala
1               5                   10
```